United States Patent
Greaves et al.

(10) Patent No.: US 8,034,125 B2
(45) Date of Patent: Oct. 11, 2011

(54) DYE COMPOSITION COMPRISING AT LEAST ONE COLORLESS DISULFIDE/THIOL PRECURSOR, AND DYEING PROCESS USING THE COMPOSITION

(75) Inventors: Andrew Greaves, Magny-le-Hongre (FR); Nicolas Daubresse, La Celle St Cloud (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 12/679,665

(22) PCT Filed: Sep. 23, 2008

(86) PCT No.: PCT/EP2008/062710
§ 371 (c)(1),
(2), (4) Date: Aug. 10, 2010

(87) PCT Pub. No.: WO2009/040354
PCT Pub. Date: Apr. 2, 2009

(65) Prior Publication Data
US 2011/0016642 A1 Jan. 27, 2011

Related U.S. Application Data

(60) Provisional application No. 60/960,742, filed on Oct. 11, 2007.

(30) Foreign Application Priority Data

Sep. 24, 2007 (FR) ...................................... 07 57808

(51) Int. Cl.
*A61Q 5/10* (2006.01)
*C07C 321/00* (2006.01)

(52) U.S. Cl. ............. 8/405; 8/409; 8/426; 8/432; 8/435; 8/565; 8/568; 8/608; 8/616; 8/642; 132/202; 132/208; 562/426

(58) Field of Classification Search ............... 8/405, 409, 8/426, 432, 435, 565, 568, 608, 616, 642; 132/202, 208; 562/426
See application file for complete search history.

(56) References Cited

U.S. PATENT DOCUMENTS

| | | | |
|---|---|---|---|
| 2,864,813 A | 12/1958 | Bossard et al. | |
| 2,904,385 A | 9/1959 | Roger et al. | |
| 5,034,014 A | 7/1991 | Wenke | |
| 7,247,713 B2 | 7/2007 | David et al. | |
| 7,488,354 B2 | 2/2009 | Daubress et al. | |
| 2006/0080791 A1* | 4/2006 | Daubresse et al. | 8/405 |
| 2007/0130702 A1 | 6/2007 | Andrean et al. | |

FOREIGN PATENT DOCUMENTS

| | | |
|---|---|---|
| DE | 1 544 506 | 4/1970 |
| DE | 198 42 071 A1 | 3/2000 |
| DE | 101 48 844 A1 | 10/2003 |
| EP | 1 133 975 B1 | 9/2001 |
| EP | 1 407 756 B1 | 4/2004 |
| EP | 1 647 580 A1 | 4/2006 |
| EP | 1 672 033 A2 | 6/2006 |
| FR | 2 787 708 A1 | 6/2000 |
| GB | 1 094 309 | 12/1967 |
| GB | 2 183 237 A | 6/1987 |
| JP | 54-008626 | 1/1979 |
| WO | WO 2005/097051 A2 | 10/2005 |
| WO | WO 2006/131163 Z1 | 12/2006 |
| WO | WO 2006/134043 A2 | 12/2006 |

OTHER PUBLICATIONS

STIC Search Report dated May 19, 2011.*
Notice of Allowance mailed Mar. 1, 2011, in U.S. Appl. No. 12/677,450.
STIC Search Report dated Nov. 9, 2010, for U.S. Appl. No. 12/677,450.
Copending U.S. Appl. No. 12/677,450, filed Mar. 10, 2010.
Copending U.S. Appl. No. 12/679,246, filed Mar. 19, 2010.
English language Abstract of DE 198 42 071 A1, dated Mar. 16, 2000.
English language Abstract of DE 101 48 844 A1, dated Apr. 10, 2003.
English language Abstract for JP 54-008626, dated Dec. 23, 1979.
English language Abstract of WO 2006/131163 A1, dated Dec. 14, 2006.
International Search Report for PCT/EP2008/061885, dated Oct. 22, 2009.
International Search Report for PCT/EP2008/062478, dated Dec. 3, 2009.
International Search Report for PCT/EP2008/062710, dated Dec. 12, 2009.
Imahori, H. et al., "Photoinduced Electron Transfer at a Gold Electrode Modified with a Self-Assembled Monolayer of Fullerene," Chem. Commun. vol. 6, pp. 557-558 (1999).
Klepp, J. et al., "Nature of Coenzyme Binding by Glyceraldehyde-3-phophate Dehydrogenase: C NMR Studies with Oxidized [4-13C]Nicotinamide Adenine Dinucleotide," J. Am. Chem. Soc., vol. 111, No. 12, pp. 4440-4447 (1989).
Knies, T. et al., "Nicotinamide-Substituted Complexes as Redox Markers," J. Labelled. CPD. Radiopharm., vol. XLI, pp. 605-614 (1998).

* cited by examiner

*Primary Examiner* — Eisa Elhilo
(74) *Attorney, Agent, or Firm* — Finnegan, Henderson, Farabow, Garrett & Dunner

(57) ABSTRACT

The present invention relates to the dyeing of keratin materials using two colorless dye precursors, at least one of which contains a disulfide/thiol unit, said precursors reacting together chemically to form the color in situ. The process according to the invention makes it possible in the context of certain variants to solve the problems caused by the color generated during the process, while at the same time not degrading the efficacy of the coloration, and especially of the lightening effect. The colorations obtained are moreover powerful, chromatic, sparingly selective, and fast with respect to external agents such as sunlight, perspiration and especially shampoo.

17 Claims, No Drawings

DYE COMPOSITION COMPRISING AT LEAST ONE COLORLESS DISULFIDE/THIOL PRECURSOR, AND DYEING PROCESS USING THE COMPOSITION

CROSS REFERENCE TO RELATED APPLICATIONS

This application is a national phase application based on PCT/EP2008/062710, filed Sep. 23, 2008, which claims the priority of French Application No. 0757808, filed Sep. 24, 2007, and claims the benefit of U.S. Provisional Application No. 60/960,742, filed Oct. 11, 2007, the content of all of which is incorporated herein by reference in their entirety.

The present invention relates to the dyeing of keratin materials using two colorless dye precursors, at least one of which contains a disulfide/thiol unit, said precursors reacting together chemically to form the color in situ.

Essentially two types of dyeing are used for coloring human keratin fibers.

The first is semi-permanent dyeing or direct dyeing, which uses dyes that are capable of giving to the natural color of the hair a more or less pronounced change. The process conventionally used in direct dyeing consists in applying to the keratin fibers direct dyes, which are colored and coloring molecules that have affinity for the fibers, leaving them to diffuse and then rinsing the fibers.

The dyes used are colored and coloring substances that have a certain affinity for keratin fibers. The direct dyes that are conventionally used are, for example, dyes of the nitrobenzene type, anthraquinone dyes, nitropyridines and dyes of the azo, xanthene, acridine, azine or triarylmethane type.

The dyeing of keratin fibers using these standard direct dyes does not make it possible to appreciably lighten the keratin fibers and does not have satisfactory fastness especially with respect to shampoos.

When lightening of keratin fibers is desired, a chemical bleaching process is conventionally performed. This process consists in treating the keratin fibers with a strong oxidizing system, generally constituted by hydrogen peroxide optionally combined with persalts, usually in an alkaline medium. If a lighter coloration than the original color of the fibers is desired to be obtained, while at the same time coloring the fibers, this technique being known as lightening dyeing, it is necessary to combine the direct dyes with at least one oxidizing agent in alkaline medium.

The drawback of lightening dyeing is, specifically, due to the fastness of the dyes, which remains limited and which leads to fading of the color, or even to a color change over time, via loss of the dye(s).

Furthermore, the chemical bleaching system has the drawback of degrading keratin fibers and of impairing their cosmetic properties. Specifically, the fibers have a tendency to become coarse, more difficult to disentangle and more brittle. Finally, the lightening or bleaching of keratin fibers with oxidizing agents is incompatible with treatments for changing the shape of said fibers, particularly relaxing treatments.

Another lightening technique consists in applying to dark hair fluorescent direct dyes. This technique, described especially in documents WO 03/028 685 and WO 2004/091 473, makes it possible to respect the quality of the keratin fiber during the treatment. However, these fluorescent direct dyes do not have sufficient fastness with respect to external agents. To increase the fastness of direct dyes, it is known practise to use disulfide dyes, especially dyes containing an azo-imidazolium chromophore, in patent applications WO 2005/097 051 or EP 1 647 580, and dyes containing pyridinium/indolinium-styryl chromophores in patent applications WO 2006/134 043 and WO 2006/136 617.

The second type of dyeing is permanent dyeing or oxidation dyeing. It is performed in the presence of oxidation dye precursors, more particularly one or more oxidation bases optionally combined with one or more couplers. These precursors are uncolored or sparingly colored compounds, which, once mixed at the time of use with oxidizing agents under alkaline conditions, lead to colored and coloring compounds via a mechanism of oxidative condensation.

This type of dyeing gives access to colorations that are longerlasting than those obtained with direct dyes. However, the use requires an oxidizing agent under alkaline conditions, which may, in the long term, result in degradation of the keratin fiber.

The two types of process using direct dyes or oxidation dyeing of the hair have the drawback of being soiling. Specifically, with direct dyeing, for which the composition applied to the fibers is already colored, and with oxidation dyeing, which rapidly becomes highly colored during the process, the risks of staining clothing, dyeing tools, rinsing basins or towels are great, during the application and the leave-on time of the dye composition.

Furthermore, the initial color of the composition applied to the fibers, or the color that appears during the process, masks the final coloration of the fibers, and may cause certain difficulties. The first being that the color of the composition, although often highly chromatic, or even aggressive to the eye, may worry the person on whom the dye composition is applied, and all the more so if this person is not in the habit of undertaking such hair treatments.

Another drawback is that there is not at the present time any way for the person on whom the treatment is performed to exert any control of the coloration, in the sense that she might request that the process be stopped at a point at which she finds the color obtained satisfactory.

Using standard dyeing processes, it is also not possible to perform "progressive dyeing" or "dyeing with a progressive lightening effect" by applying a reagent contained, for example, in a shampoo that would generate gradually as it is used, after several days or even weeks, color on the hair, without denaturing the keratin fibers.

Moreover, it is known practise to apply to keratin fibers, instead of direct dyes, dye precursors that form the color in situ via a chemical reaction. For example, aromatic aldehyde/ketone precursors and a precursor with an activated CH, which form the direct dye in situ, have been described in patents U.S. Pat. Nos. 6,790,239 and 6,770,102. These precursors do not bear any disulfide or thiol functions.

(Hetero)aryl disulfide compounds have been widely used in fields other than that of dyeing of the hair, for example, in the study of the reactivity of isochroman and isothiochroman [*Justus Liebigs Annalen der Chemie* (1978), (7), 1123-8; ibid (1974), (5), 734-40]; in models of molecular recognition by interaction of hydrogen bonds [*Chemical Communications* (1996), (10), 1193-1194]; in the formation of gold-affinity multilayer materials [*Organic Letters* (2000), 2(26), 4141-4144, *Chemistry Letters* (2006), 35(8), 870-871]; in controlling the electron transfer between cytochrome C and gold electrons [*Langmuir* (2003), 19(6), 2378-2387, *Journal of the American Chemical Society* (2003), 125(25), 7704-7714]; in liquid crystals [*Molecular Crystals and Liquid Crystals Science and Technology*, Section A: (2002), 377, 137-140]; or in the synthesis of modified nanoparticles [*Journal of the American Chemical Society* (2004), 126(10), 3026-3027]. However, the prior art does not mention the use of disulfide or thiol precursors for dyeing keratin fibers.

The object of the present invention is to propose a process for dyeing keratin fibers, especially with a lightening effect, particularly on dark hair, which does not have the drawbacks mentioned above, and which makes it possible in the case of certain variants to solve the problems due to the color generated during the process, while at the same time not degrading the efficacy of the coloration, and especially of the lightening effect.

The colorations obtained are moreover powerful, chromatic, sparingly selective, and fast with respect to external agents such as sunlight, perspiration and especially shampoo.

Thus, one subject of the present invention is a process for dyeing keratin fibers, especially the hair, more particularly dark hair, which consists in applying to said fibers, which have optionally been pretreated with a reducing agent:

i) a cosmetically acceptable composition comprising at least one colorless thiol/disulfide dye precursor of formula (I):

[Z-A-L-S]$_x$—(Y)$_y$    formula (I):

ii) and a cosmetically acceptable composition comprising at least one colorless dye precursor of formula (II):

B—X    formula (II):

in which the portion B of the precursor of formula (II) reacts chemically with portion A of the precursor of formula (I) to form a colored or colored and fluorescent chromophore B—X'-A-; in which formulae (I) and (II):

y represents 0 or 1;

x represents 1 or 2;

L represents an optionally substituted divalent $C_1$-$C_{20}$ hydrocarbon-based chain, optionally interrupted and/or optionally ending at one or other of its ends i) with one or more divalent groups or combinations thereof chosen from: —N($R_a$)—; —N$^+$($R_a$)($R_b$)—, An$^-$, —O—; —S—; —CO— and —SO$_2$— with $R_a$ and $R_b$, which may be identical or different, chosen from a hydrogen and a ($C_1$-$C_6$)alkyl, hydroxy($C_1$-$C_6$)alkyl or (di) ($C_1$-$C_6$)(alkyl)amino($C_1$-$C_6$)alkyl radical and An$^-$ representing an anionic counterion, or ii) with a cationic heterocycle or cationic heteroaryl Het$^+$, An$^-$, with An$^-$ as defined above and Het$^+$ representing a saturated or unsaturated 5- to 10-membered heterocycle, or a 5- to 10-membered heteroaryl such as imidazolium, pyridinium, piperazinium, piperidinium, pyrrolidinium or benzimidazolium; L especially represents a ($C_1$-$C_6$) alkylene chain connected to A via a bond NR, —NRC(O)— or —C(O)NR—;

A and B, which may be identical or different, represent a colorless chromophore;

A and B especially represent cationic or noncationic aryl or heteroaryl groups;

the optionally substituted aryl radical especially represents a phenyl, biphenyl, naphthyl, indenyl, anthracenyl or tetrahydronaphthyl, more particularly an optionally substituted phenyl;

the optionally substituted heteroaryl radical especially represents a group chosen from the following cationic or noncationic heteroaryl radicals comprising from 1 to 4 heteroatoms:

i) 5-, 6- or 7-membered monocyclic radicals such as furanyl or furyl, pyrrolyl or pyrryl, thiophenyl or thienyl, pyrazolyl, oxazolyl, oxazolium, isoxazolyl, isoxazolyl, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;

ii) 8- to 11-membered bicyclic radicals such as indolyl, indolinium, benzimidazolyl, benzimidazolium, benzoxazolyl, benzoxazolium, dihydrobenzoxazolinyl, benzothiazolyl, benzothiazolium, pyridoimidazolyl, pyridoimidazolium, thienocycloheptadienyl, said radicals possibly being substituted with a ($C_1$-$C_3$) alkenyl group bearing a function —C=(G)-R° in which the double bond(s) of the ($C_1$-$C_3$) alkenyl group is (are) conjugated with the double bond —C=G; with R° representing a hydrogen atom or a ($C_1$-$C_4$)alkyl group and G representing an oxygen or sulfur atom or a group NR', and R and R' may be identical or different;

in particular, said radicals may be substituted with a group =CR—C(G)R° with the double bond directly connected to the nonaromatic part of the bicycle;

more particularly, A or B represents a group as defined below:

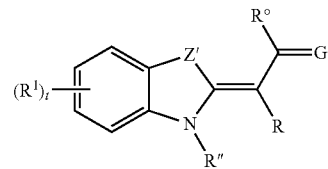

with:

R$^1$, which may be identical or different, represents a halogen atom or a ($C_1$-$C_6$)alkyl, ($C_1$-$C_6$)alkoxy, ($C_1$-$C_6$)alkylthio, (di) ($C_1$-$C_6$)(alkyl)amino, ($C_1$-$C_6$)polyhaloalkyl, hydroxyl, ($C_1$-$C_6$)polyhydroxy-alkyl, polyhydroxy($C_1$-$C_6$)alkoxy, cyano, R-G-C(G')-, R—C(G')-G-, R'S(O)$_2$—N(R)—, RR'N—S(O)$_2$— group with G or G', which may be identical or different, representing an oxygen or sulfur atom or a group NR', and R and R', which may be identical or different, representing a hydrogen atom or a ($C_1$-$C_6$)alkyl group;

R$^1$ is particularly in position 5 and more particularly R$^1$ represents a halogen such as chlorine or a ($C_1$-$C_6$)alkoxy group such as methoxy, RR'N—S(O)$_2$— such as Me-S(O)$_2$, or RR'N—C(O)— such as H$_2$N—C(O)—;

or two contiguous groups R$^1$ form with the two carbon atoms that bear them an optionally substituted benzo group;

t represents an integer between 0 and 4 inclusive;

G and R° are as defined previously;

R representing a hydrogen atom or a ($C_1$-$C_4$)alkyl group;

R" represents a hydrogen atom or a (polyhydroxy)($C_1$-$C_4$)alkyl group;

Z' represents an oxygen or sulfur atom or a methylene group —C(R$^2$)(R$^3$)— with R$^2$ and R$^3$, which may be identical or different, representing a hydrogen atom or a ($C_1$-$C_6$)alkyl group;

preferably, the heteroaryl radical represents a pyridyl, pyridinium, triazinium, imidazolyl, imidazolium, pyrazolyl, thiazolium, oxazolium, benzothiazolium, benzoxazolium, quinolinium, indolyl, indolinium or a group:

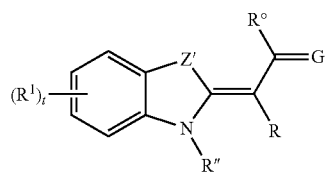

as defined previously;

X and Z represent a chemical function capable of reacting together to form a group X';

X' representing a chain allowing the electron transfer between chromophore A and chromophore B; X' is particularly a divalent $C_2$-$C_8$alkenylene group comprising from 1 to 4 conjugated double bonds such as =CH—CH=CH—, a $C_1$-$C_7$ (poly)methine chain, a divalent ($C_1$-$C_7$)alkenyleneimino group, comprising from 1 to 3 conjugated double bonds such as —CR=N—, —N=CR—, —CR=CR—N=CR—, —N=CR—CR=CR—, =CR—N=CH—, an aza group —N=N—, a triaza group —N=N—N—, a hydrazono group —CH=N—NR—, NR—N=CH—, =CR—, =CR—CR=CR—; with R, which may be identical or different, representing a hydrogen atom or a ($C_1$-$C_4$) alkyl group;

Y represents: i) a hydrogen atom; ii) an alkali metal; iii) an alkaline-earth metal; iv) an ammonium group: $N^+R^\alpha R^\beta R^\gamma R^\delta$, $An''^-$ or a phosphonium group: $P^+R^\alpha R^\beta R^\gamma R^\delta$, $An''^-$ with $R^\alpha$, $R^\beta$, $R^\gamma$ and $R^\delta$, which may be identical or different, representing a hydrogen atom or a ($C_1$-$C_4$) alkyl group, and $An''^-$ being an anionic counterion; or v) a protecting group for a thiol function;

it being understood that when x is 2, then y is zero, and when x is 1, then y is 1.

A subject of the invention is furthermore a cosmetic composition comprising at least one colorless disulfide dye precursor of formula ($I_1$), ($I_2$), or a colorless thiol or thiol-protected dye precursor of formula ($I_3$), ($I_4$) or ($I_5$):

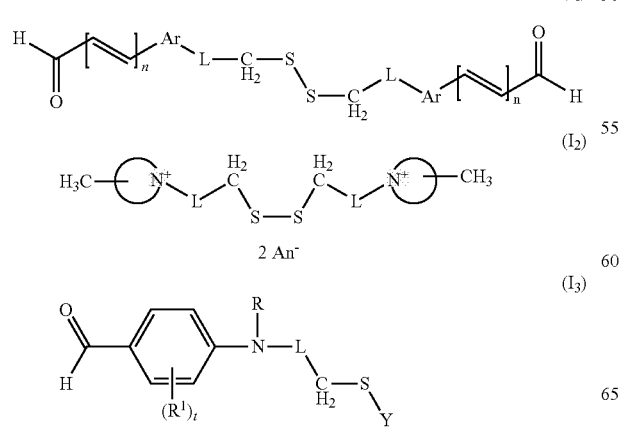

the organic or mineral acid salts, optical isomers, geometrical isomers, and solvates such as hydrates thereof;

in which formulae ($I_1$), ($I_2$), ($I_3$), ($I_4$) or ($I_5$):

Ar represents an optionally substituted arylene or heteroarylene group such as phenylene, naphthylene, pyridinylene or pyrazolene and more particularly phenylene;

R represents a hydrogen atom or a ($C_1$-$C_6$)alkyl group;

Y represents: i) a hydrogen atom; ii) an alkali metal; iii) an alkaline-earth metal; iv) an ammonium group: $N^+R^\alpha R^\beta R^\gamma R^\delta$, $An^-$ or a phosphonium group: $P^+R^\alpha R^\beta R^\gamma R^\delta$, $An^-$ with $R^\alpha$, $R^\beta$, $R^\gamma$ and $R^\delta$, which may be identical or different, representing a hydrogen atom or a ($C_1$-$C_4$) alkyl group and $An^-$ representing an anionic counterion, or v) a protecting group for a thiol function;

L is as defined previously;

n is 0 or 1; advantageously, n is 0,

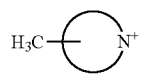

represents a 5- to 13-membered cationic heteroaryl group which may comprise, besides the cationic nitrogen atom, from 1 to 3 heteroatoms chosen from nitrogen, oxygen and sulfur, and which bears on a carbon atom a methyl group; in particular, the heteroaryl group represents a pyridinium group substituted in the ortho or para position with a methyl group;

$Het^+$ represents a cationic heteroarylene group bearing at least one methyl group, chosen from:

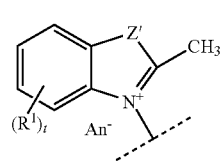

(A)

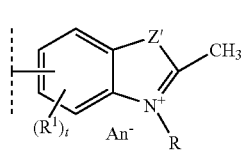

(B)

-continued

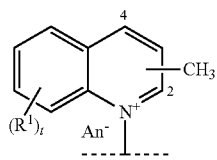 (C)

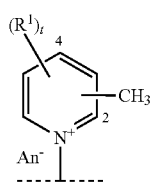 (D)

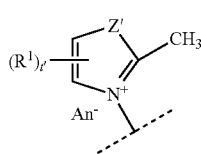 (E)

in which radicals (A) to (E):
the methyl group of the Het+ groups (C) and (D) is in position 2 or 4;

$R^1$ represents a halogen atom or a $(C_1$-$C_6)$alkyl, $(C_1$-$C_6)$alkoxy, $(C_1$-$C_6)$alkylthio, (di) $(C_1$-$C_6)$(alkyl)amino, $(C_1$-$C_6)$polyhaloalkyl, hydroxyl, $(C_1$-$C_6)$polyhydroxyalkyl, polyhydroxy$(C_1$-$C_6)$alkoxy, cyano, R-G-C(G')-, R—C(G')-G-, R'S(O)$_2$—N(R)—, RR'N—S(O)$_2$— group with G or G', which may be identical or different, representing an oxygen or sulfur atom or a group NR', and R and R', which may be identical or different, representing a hydrogen atom or a $(C_1$-$C_6)$ alkyl group; in particular, $R^1$ is in position 5 and $R^1$ more particularly represents a halogen such as chlorine or a $(C_1$-$C_6)$alkoxy group such as methoxy, RR'N—S(O)$_2$— such as Me-S(O)$_2$ or RR'N—C(O)— such as $H_2N$—C(O)—;

R represents a hydrogen atom or a (polyhydroxy)$(C_1$-$C_4)$alkyl group;

or alternatively two contiguous groups $R^1$ form with the two carbon atoms that bear them an optionally substituted benzo group;

t represents an integer between 0 and 4 inclusive;

t' represents an integer between 0 and 2 inclusive;

Z' represents an oxygen or sulfur atom or a methylene group —C($R^2$) ($R^3$)— with $R^2$ and $R^3$, which may be identical or different, representing a hydrogen atom or a $(C_1$-$C_6)$alkyl group;

An⁻ represents an anionic counterion; it being understood that the compounds of formula ($I_1$), ($I_2$), ($I_3$), ($I_4$) or ($I_5$) cannot represent the following compounds (I) to (xxxiv):

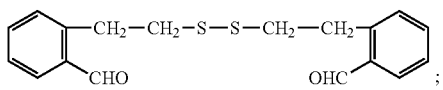 (i)

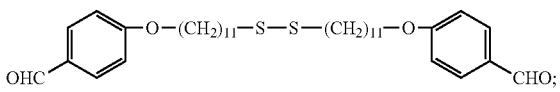 (ii)

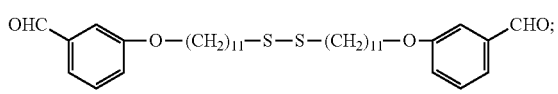 (iii)

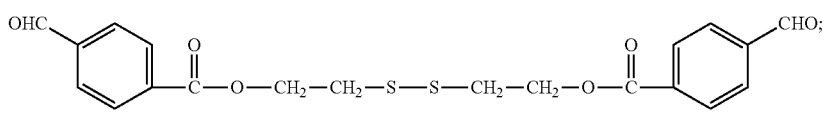 (iv)

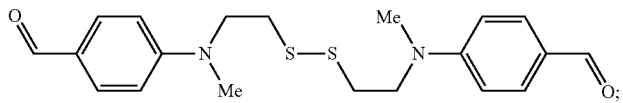 (v)

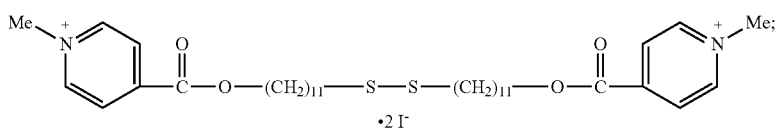 (vi)

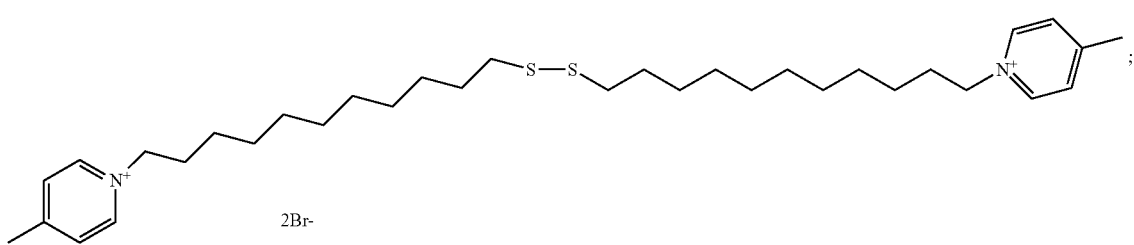

(vii)

(viii)

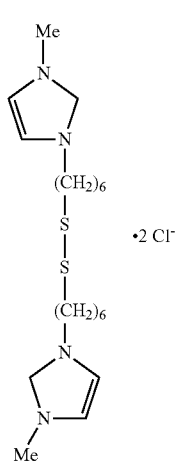
(ix)
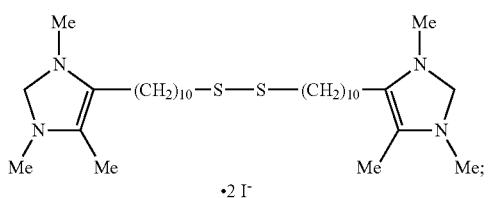
(x)
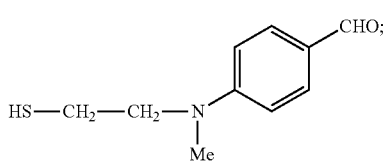
(xi)
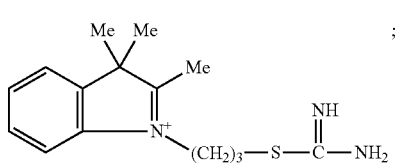
(xii)
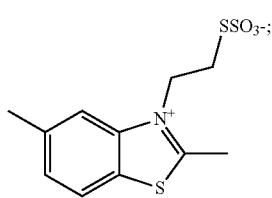
(xiii)
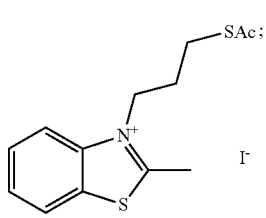
(xiv)
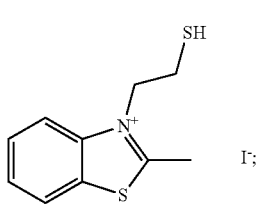
(xv)
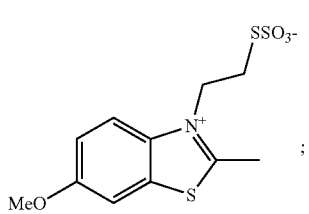
(xvi)
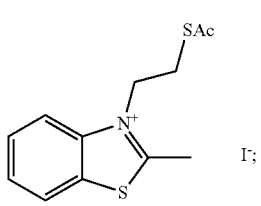
(xvii)
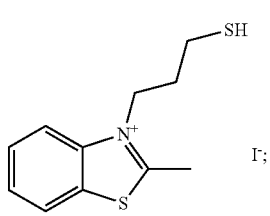
(xviii)
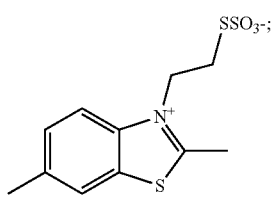
(xix)
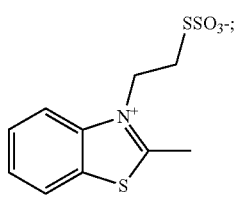
(xx)

-continued
(xxi) 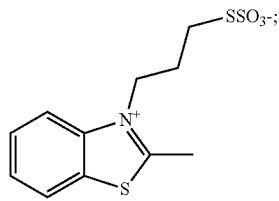 
(xxii) 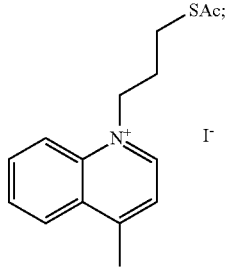
with Ac representing an acetyl group
(xxiii) 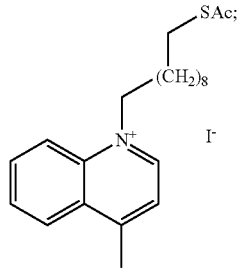
(xxiv)
(xxv)
(xxvi)
An = MeSO$_4^-$ or NO$_3^-$ or pTSA$^-$
(xxvii) 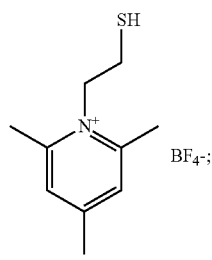
(xxviii)
(xxix) 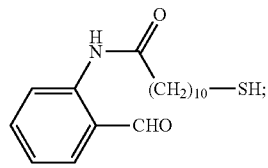
(xxx)
(xxxi)

-continued

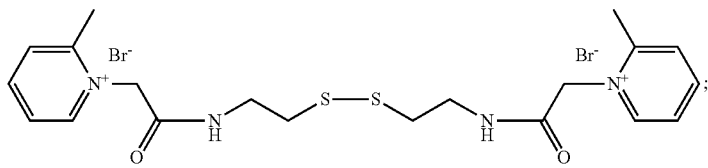
(xxxii)

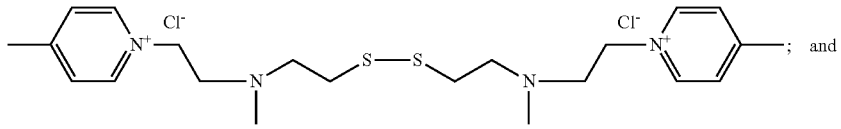
(xxxiii) ; and

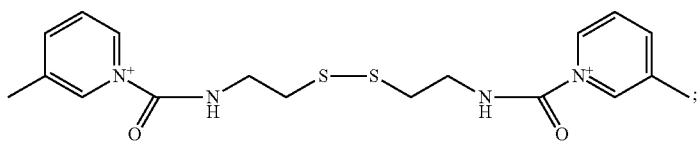
(xxxiv)

it being understood that the aldehyde functions of formulae ($I_1$), ($I_3$) and ($I_4$) may be protected, for example with acetals.

Another subject of the invention concerns a disulfide compound of formula ($I_1$) or ($I_2$), or a thiol or thiol-protected compound of formula ($I_3$), ($I_4$) or ($I_5$) as defined previously, said compound being different from the compounds (i) to (xxxiv) as defined previously.

A subject of the invention is also a multi-compartment device comprising, in a first compartment, a cosmetic composition containing at least one colorless thiol/disulfide precursor of formula (I) as defined previously; a second compartment comprising a cosmetic composition containing at least one colorless precursor of formula (II) as defined previously; optionally, another compartment comprising a reducing agent capable of reducing keratin fibers and the disulfide precursor of formula (I); and/or optionally another compartment containing an oxidizing agent capable of fixing the precursor of formula (I) to the keratin fibers.

The dyeing process according to the invention allows the dyeing of keratin fibers, especially of dark hair, cleanly since the rinsing liquors are not colored. The compositions comprising the dye precursors according to the invention have, in the context of certain variants thereof, the advantage of being colorless and of remaining so during the leave-on time of the composition.

Moreover, and this represents another particular advantage of the process according to the invention, during the process the fibers can be seen to be colored or lightened under the effect of the composition comprising the colorless precursor of formula (II), this color being the real coloration, not masked by the color of the composition applied to the fibers. Thus, the person on whom the treatment is performed can ask for the process to be stopped when the desired level of coloration is reached.

A contrario, the colorations obtained using the composition also make it possible to achieve progressive colorations. Specifically, it is possible to react a precursor of formula (I) with the keratin fibers and then, after a few days or even a few weeks, to "reveal" the color or "intensify it". Revealing the color by adding a precursor of formula (II) capable of reacting with the first of formula (I) to generate the color. Intensifying the color or modifying the color by adding a precursor of formula (II) capable of reacting with the precursor of formula (I) or by adding another colorless precursor of formula (II), different from the one which was added during the revelation.

The dyeing process according to the invention makes it possible to visibly dye dark human keratin fibers, especially dark hair.

The dyeing process according to the invention also has the advantage of not requiring the use of a standard lightening agent, while at the same time giving access to powerful colorations, of the order of those achieved by using an oxidation dye. Specifically, it is possible to dye with lightening using colorless precursors of formula (I) or (II) taken separately, without having to use oxidizing agents, which thus avoids degrading the keratin fibers.

The composition according to the invention also makes it possible to dye keratin fibers in natural colors, such as golden, coppery, brown, mahogany and black colors, without, however, coloring the dye formulation. Moreover, the dyes and colors derived from the dye precursors of formulae ($I_1$) to ($I_5$) broaden the color range from yellows to greens. This also makes it possible to achieve strong and chromatic dyeing of bleached keratin fibers.

The process of the invention makes it possible to obtain a coloration on the hair, without degrading it, which is remnant with respect to shampooing, common attacking factors (sunlight and perspiration), and hair treatments.

However, other characteristics and advantages of the invention will emerge more clearly on reading the description and the examples that follow.

For the purposes of the invention, the term "dark keratin material" means keratin material whose lightness $L^*$ measured in the CIEL $L^*a^*b^*$ system is less than or equal to 45 and preferably less than or equal to 40, given that $L^*=0$ is equivalent to black and $L^*=100$ is equivalent to white.

For the purposes of the invention, the expression "naturally or artificially dark hair" means hair whose tone depth is less than or equal to 6 (dark blond) and preferably less than or equal to 4 (chestnut-brown).

The lightening of the hair is evaluated by the "tone depth" before and after application of the precursors of formula (II). The notion of "tone" is based on the classification of natural shades, one tone separating each shade from the shade immediately following or preceding it. This definition and the classification of natural shades are well known to hairstyling professionals and are published in the book "Sciences des traitements capillaires [Hair treatment sciences]" by Charles Zviak, 1988, published by Masson, pp. 215 and 278.

The tone depths range from 1 (black) to 10 (very light blond), one unit corresponding to one tone; the higher the figure, the lighter the shade.

Artificially dyed hair is hair whose color has been modified by a coloration treatment, for example a coloration with direct dyes or oxidation dyes.

For the purposes of the invention, the term "bleached hair" means hair whose tone depth is greater than 6 and preferably greater than 7.

One means for measuring the lightening effect given to the hair after application of the fluorescent dyes of the invention is to use the phenomenon of reflectance of the hair.

Preferably, the composition should, after application to dark hair, lead to the results below.

What is concerned is the reflectance performance of the hair when it is irradiated with visible light in the wavelength range from 400 to 700 nanometers.

The curves of reflectance as a function of the wavelength, for hair treated with the composition of the invention and for untreated hair, are then compared.

The curve corresponding to the treated hair should show a reflectance in the wavelength range from 500 to 700 nanometers higher than the curve corresponding to the untreated hair.

This means that, in the wavelength range from 540 to 700 nanometers, there is at least one region in which the reflectance curve corresponding to the treated hair is higher than the reflectance curve corresponding to the untreated hair. The term "higher" means a difference in reflectance of at least 0.05% and preferably of at least 0.1%. This does not prevent there from being in the wavelength range from 540 to 700 nanometers at least one region in which the reflectance curve corresponding to the treated hair is superposable, or lower than the reflectance curve corresponding to the untreated hair.

Preferably, the wavelength at which the difference is maximal between the reflectance curve for the treated hair and that for the untreated hair is in the wavelength range from 500 to 650 nanometers and preferably in the wavelength range from 550 to 620 nanometers.

For the purposes of the present invention, and unless otherwise indicated:
the term "colorless compound or chromophore" means a compound or chromophore that does not absorb light in the visible spectrum, i.e. in the spectrum at a wavelength of between 250 and 800 nm; particularly between 400 and 700 nm (Ullmann's Encyclopedia, 2005, Wiley-VcH, Verlag "Dyes, General Survey", §2.1 Basic Principle of Color);
the term "colored compound or chromophore" means a compound or chromophore that absorbs light in the visible spectrum at an absorption wavelength of between 250 and 800 nm as defined previously, particularly between 400 and 800 nm;
the term "fluorescent compound or chromophore" means a compound or chromophore that absorbs light at a maximum wavelength that is in the visible spectrum and that re-emits the light in the visible spectrum at a wavelength longer than the maximum absorption wavelength, the difference between the maximum absorption wavelength and the emission or fluorescence wavelength being commonly referred to as the Stoke's shift: the Stoke's shift is particularly between 1 and 100 nm;
the "aryl" or "heteroaryl" radicals or the aryl or heteroaryl portion of a radical may be substituted with at least one substituent chosen from:
a $C_1$-$C_{16}$ and preferably $C_1$-$C_8$alkyl radical, optionally substituted with one or more radicals chosen from the following radicals: hydroxyl, $C_1$-$C_2$ alkoxy, $C_2$-$C_4$ (poly)hydroxyalkoxy, acylamino, amino substituted with two identical or different $C_1$-$C_4$alkyl radicals, optionally bearing at least one hydroxyl group, or both radicals possibly forming with the nitrogen atom to which they are attached a saturated or unsaturated, optionally substituted 5- to 7-membered and preferably 5- or 6-membered heterocycle, optionally comprising another heteroatom identical to or different from nitrogen;
a halogen atom such as chlorine, fluorine or bromine;
a hydroxyl group;
a $C_1$-$C_2$ alkoxy radical;
a $C_1$-$C_2$ alkylthio radical;
a $C_2$-$C_4$ (poly)hydroxyalkoxy radical;
an amino radical;
a 5- or 6-membered heterocycloalkyl radical;
an optionally cationic 5- or 6-membered heteroaryl radical, preferentially imidazolium, optionally substituted with a ($C_1$-$C_4$)alkyl radical, preferentially methyl;
an amino radical substituted with one or two identical or different $C_1$-$C_6$alkyl radicals, optionally bearing at least:
i) one hydroxyl group,
ii) one amino group optionally substituted with one or two optionally substituted $C_1$-$C_3$alkyl radicals, said alkyl radicals possibly forming with the nitrogen atom to which they are attached a saturated or unsaturated, optionally substituted 5- to 7-membered heterocycle, optionally comprising at least one other heteroatom identical to or different from nitrogen,
—N(R)—C(O)—R' in which the radical R is a hydrogen atom or a $C_1$-$C_4$ alkyl radical optionally bearing at least one hydroxyl group and the radical R' is a $C_1$-$C_2$alkyl radical;
(R)$_2$N—C(O)— in which the radicals R, which may be identical or different, represent a hydrogen atom or a $C_1$-$C_4$ alkyl radical optionally bearing at least one hydroxyl group;
R'S(O)$_2$—N(R)— in which the radical R represents a hydrogen atom or a $C_1$-$C_4$ alkyl radical optionally bearing at least one hydroxyl group and the radical R' represents a $C_1$-$C_4$ alkyl radical, or a phenyl radical;
(R)$_2$N—S(O)$_2$— in which the radicals R, which may be identical or different, represent a hydrogen atom or a $C_1$-$C_4$ alkyl radical optionally bearing at least one hydroxyl group,
a carboxylic radical in acid or salified form (preferably with an alkali metal or a substituted or unsubstituted ammonium);
a cyano group;
a polyhaloalkyl group containing from 1 to 6 carbon atoms and comprising from 1 to 6 identical or different halogen atoms, the polyhaloalkyl group is, for example, trifluoromethyl;
the cyclic or heterocyclic part of a nonaromatic radical may be substituted with at least one substituent borne by a carbon atom, chosen from the groups:
hydroxyl,
$C_1$-$C_4$ alkoxy,
$C_2$-$C_4$ (poly)hydroxyalkoxy,
a $C_1$-$C_2$ alkylthio radical;

RC(O)—N(R')— in which the radical R' is a hydrogen atom or a $C_1$-$C_4$ alkyl radical optionally bearing at least one hydroxyl group and the radical R is a $C_1$-$C_2$alkyl radical or an amino radical substituted with two identical or different $C_1$-$C_4$ alkyl groups, optionally bearing at least one hydroxyl group;

RC(O)—O— in which the radical R is a $C_1$-$C_4$ alkyl radical or an amino radical substituted with one or two identical or different $C_1$-$C_4$ alkyl groups optionally bearing at least one hydroxyl group, said alkyl radicals possibly forming with the nitrogen atom to which they are attached a saturated or unsaturated, optionally substituted 5- to 7-membered heterocycle, optionally comprising at least one other heteroatom identical to or different from nitrogen;

RO—C(O)— in which the radical R is a $C_1$-$C_4$ alkyl radical optionally bearing at least one hydroxyl group;

a cyclic or heterocyclic radical, or a nonaromatic portion of an aryl or heteroaryl radical, may also be substituted with one or more oxo or thioxo groups;

an "aryl" radical represents a fused or nonfused monocyclic or polycyclic carbon-based group containing from 6 to 22 carbon atoms, and in which at least one ring is aromatic; preferentially, the aryl radical is a phenyl, biphenyl, naphthyl, indenyl, anthracenyl or tetrahydronaphthyl;

a "diarylalkyl" radical represents a group comprising on the same carbon atom of an alkyl group two identical or different aryl groups such as diphenylmethyl or 1,1-diphenylethyl;

a "heteroaryl radical" represents a fused or nonfused, optionally cationic, 5- to 22-membered monocyclic or polycyclic group, comprising from 1 to heteroatoms chosen from nitrogen, oxygen, sulfur and selenium, and at least one ring of which is aromatic; preferentially, a heteroaryl radical is chosen from acridinyl, benzimidazolyl, benzobistriazolyl, benzopyrazolyl, benzopyridazinyl, benzoquinolyl, benzothiazolyl, benzotriazolyl, benzoxazolyl, pyridyl, tetrazolyl, dihydrothiazolyl, imidazopyridyl, imidazolyl, indolyl, isoquinolyl, naphthoimidazolyl, naphthooxazolyl, naphthopyrazolyl, oxadiazolyl, oxazolyl, oxazolopyridyl, phenazinyl, phenoxazolyl, pyrazinyl, pyrazolyl, pyrylyl, pyrazoyltriazyl, pyridyl, pyridinoimidazolyl, pyrrolyl, quinolyl, tetrazolyl, thiadiazolyl, thiazolyl, thiazolopyridyl, thiazoylimidazolyl, thiopyrylyl, triazolyl, xanthylyl and the ammonium salt thereof;

a "diheteroarylalkyl" radical represents a group comprising on the same carbon atom of an alkyl group two identical or different heteroaryl groups, such as difurylmethyl, 1,1-difurylethyl, dipyrrolylmethyl or dithienylmethyl;

a "cyclic radical" is a fused or nonfused monocyclic or polycyclic nonaromatic cycloalkyl radical containing from 5 to 22 carbon atoms, which may comprise one or more unsaturations; the cyclic radical is particularly a cyclohexyl;

a "sterically hindered cyclic" radical is an aromatic or nonaromatic, substituted or unsubstituted, 6- to 14-membered cyclic radical, which may be bridged, hindered by a steric effect or constraint: sterically hindered radicals that may be mentioned include bicyclo [1.1.0] butane, mesityls such as 1,3,5-trimethylphenyl, 1,3,5-tri-tert-butylphenyl, 1,3,5-isobutylphenyl and 1,3,5-trimethylsilylphenyl, and adamantyl;

a "heterocyclic radical or heterocycle" is a fused or nonfused, 5- to 22-membered monocyclic or polycyclic nonaromatic radical, comprising from 1 to 6 heteroatoms chosen from nitrogen, oxygen, sulfur and selenium;

an "alkyl radical" is a linear or branched $C_1$-$C_{16}$, preferably $C_1$-$C_8$ hydrocarbon-based radical;

the term "optionally substituted" attributed to the alkyl radical implies that said alkyl radical may be substituted with one or more radicals chosen from the following radicals: i) hydroxyl, ii) $C_1$-$C_4$ alkoxy, iii) acylamino, iv) amino optionally substituted with one or two identical or different $C_1$-$C_4$ alkyl radicals, said alkyl radicals possibly forming with the nitrogen atom that bears them a 5- to 7-membered heterocycle optionally comprising another heteroatom identical to or different from nitrogen; v) or a quaternary ammonium group —$N^+R'R''R'''$, $M^-$ for which R', R'' and R''', which may be identical or different, represent a hydrogen atom or a $C_1$-$C_4$ alkyl group, or alternatively —$N^+R'R''R'''$ forms a heteroaryl such as imidazolium optionally substituted with a $C_1$-$C_4$ alkyl group, and $M^-$ represents the counterion of the organic or mineral acid or of the corresponding halide, an "alkoxy radical" is an alkyl-oxy or alkyl-O-radical for which the alkyl radical is a linear or branched $C_1$-$C_{16}$ and preferentially $C_1$-$C_8$ hydrocarbon-based radical;

an "alkylthio radical" is an alkyl-S— radical for which the alkyl radical is a linear or branched $C_1$-$C_{16}$ and preferentially $C_1$-$C_8$ hydrocarbon-based radical, when the alkylthio group is optionally substituted, this implies that the alkyl group is optionally substituted as defined previously;

an "alkylene chain" represents a divalent $C_1$-$C_{18}$, particularly $C_1$-$C_6$ and more particularly $C_1$-$C_2$ chain when the chain is linear; optionally substituted with one or more identical or different halogen atoms or groups chosen from hydroxyl, alkoxy, (di) ($C_1$-$C_4$)(alkyl)amino, $R^a$—$Z^a$—$C(Z^b)$— with $Z^a$ and $Z^b$, which may be identical or different, representing an oxygen or sulfur atom or a group $NR^a$, and $R^a$ representing an alkali metal, a hydrogen atom or an alkyl group and $R^{a'}$ representing a hydrogen atom or an alkyl group;

an "optionally substituted, saturated or unsaturated $C_1$-$C_{20}$ hydrocarbon-based chain" represents a hydrocarbon-based chain, particularly a $C_1$-$C_8$ chain, optionally comprising one or more conjugated or unconjugated π double bonds, the hydrocarbon-based chain particularly being saturated; said chain is optionally substituted with one or more identical or different halogen atoms or groups chosen from hydroxyl, alkoxy, (di)($C_1$-$C_4$) (alkyl)amino and $R^b$—$Z^b$—$C(Z^c)$— with $Z^b$ and $Z^c$, which may be identical or different, representing an oxygen or sulfur atom or a group $NR^{b'}$, and $R^b$ representing an alkali metal, a hydrogen atom or an alkyl group and $R^{b'}$ representing a hydrogen atom or an alkyl group;

the limit values delimiting the extent of a range of values are included in this range of values;

an "organic or mineral acid salt" is more particularly chosen from a salt derived from i) hydrochloric acid HCl, ii) hydrobromic acid HBr, iii) sulfuric acid $H_2SO_4$, iv) alkylsulfonic acids: Alk-$S(O)_2$OH such as methanesulfonic acid and ethanesulfonic acid; v) arylsulfonic acids: Ar—$S(O)_2$OH such as benzenesulfonic acid and toluenesulfonic acid; vi) citric acid; vii) succinic acid; viii) tartaric acid; ix) lactic acid, x) alkoxysulfinic acids: Alk-O—S(O)OH such as methoxysulfinic acid and ethoxysulfinic acid; xi) aryloxysulfinic acids such as tolueneoxysulfinic acid and phenoxysulfinic acid; xii) phosphoric acid $H_3PO_4$; xiii) acetic acid $CH_3C(O)OH$; xiv) triflic acid $CF_3SO_3H$; and xv) tetrafluoroboric acid $HBF_4$;

an "anionic counterion" is an anion or an anionic group associated with the cationic charge of the dye; more particularly, the anionic counterion is chosen from: i) halides such as chloride and bromide; ii) nitrates; iii) sulfonates, including $C_1$-$C_6$ alkylsulfonates: Alk-S(O)$_2$O$^-$ such as methanesulfonate or mesylate, and ethanesulfonate; iv) arylsulfonates: Ar—S(O)$_2$O$^-$ such as benzenesulfonate and toluenesulfonate or tosylate; v) citrate; vi) succinate; vii) tartrate; viii) lactate; ix) alkyl sulfates: Alk-O—S(O)O$^-$ such as methane sulfate and ethane sulfate; x) aryl sulfates: Ar—O—S(O)O$^-$ such as benzene sulfate and toluene sulfate; xi) alkoxy sulfates: Alk-O—S(O)$_2$O$^-$ such as methoxy sulfate and ethoxy sulfate; xii) aryloxy sulfates: Ar—O—S(O)$_2$O$^-$, xiii) phosphate; xiv) acetate; xv) triflate; and xvi) borates such as tetrafluoroborate;

the "solvates" represent hydrates and also the combination with linear or branched $C_1$-$C_4$ alcohols such as ethanol, isopropanol or n-propanol.

The fluorescent dyes derived from the precursors (I) and (II), or the chromophores derived from precursors (I) and (II) as defined above are fluorescent dyes or chromophores, i.e. they are capable of absorbing UV or visible radiation at a wavelength $\lambda_{abs}$ of between 250 and 800 nm and capable of re-emitting in the visible region at an emission wavelength $\lambda_{em}$ of between 400 and 800 nm.

Preferably, the fluorescent compounds or chromophores derived from the precursors of formulae (I) and (II) are dyes or chromophores capable of absorbing in the visible region $\lambda_{abs}$ between 400 and 800 nm and re-emitting in the visible region $\lambda_{em}$ between 400 and 800 nm. More preferentially, the dyes or chromophores derived from the precursors of formulae (I) and (II) are dyes capable of absorbing at a $\lambda_{abs}$ of between 420 nm and 550 nm and of re-emitting in the visible region at a $\lambda_{em}$ of between 470 and 600 nm.

The nonfluorescent dyes derived from precursors (I) and (II), or the chromophores derived from precursors (I) and (II) as defined above are dyes or chromophores capable of absorbing UV or visible radiation at a wavelength $\lambda_{abs}$ of between 400 and 800 nm but of not re-emitting visible light.

The dye precursors of the invention of formula (I) when x and y are 1, contain a function SY, which may be in covalent form —S—Y or ionic form —S$^-$Y$^+$ depending on the nature of Y and of the pH of the medium.

One subject of the invention concerns a process for dyeing keratin fibers, which consists in applying to said fibers, optionally pretreated with a reducing agent:
i) a cosmetically acceptable composition comprising at least one colorless thiol/disulfide dye precursor of formula (I); and
ii) a cosmetically acceptable composition comprising at least one colorless dye precursor of formula (II), part B of which reacts chemically with part A to form a colored or colored and fluorescent chromophore B—X'-A-;
with the compounds of formulae (I) and (II) which are as defined previously.

One particular mode concerns a dyeing process using a colorless dye precursor (I) with x and y equal to 1, and comprising a radical Y representing a hydrogen atom or an alkali metal. Advantageously, Y represents a hydrogen atom.

In accordance with another particular embodiment of the invention, in the abovementioned formula (I), Y is a protecting group known to those skilled in the art, for instance those described in the publications *"Protective Groups in Organic Synthesis"*, T. W. Greene, published by John Wiley & Sons, NY, 1981, pp. 193-217; *"Protecting Groups"*, P. Kocienski, Thieme, 3rd edition, 2005, chapter 5. It being understood that Y as protective group cannot constitute with the sulphur atom on which it is linked a disulfide reagent i.e. a compound of formula (I) where x=2 and y=0 or for example cannot constitute a formula (I$_1$) or (I$_2$) as defined herein after. Y as protective group cannot represent a group directly linked to the sulphur atom of reagent via another non oxidized sulphur atom.

In particular, when Y represents a protecting group for the thiol function, Y is chosen from the following radicals:
($C_1$-$C_4$)alkylcarbonyl;
($C_1$-$C_4$)alkylthiocarbonyl;
($C_1$-$C_4$)alkoxycarbonyl;
($C_1$-$C_4$)alkoxythiocarbonyl;
($C_1$-$C_4$)alkylthiothiocarbonyl;
(di)($C_1$-$C_4$)(alkyl)aminocarbonyl;
(di)($C_1$-$C_4$)(alkyl)aminothiocarbonyl;
arylcarbonyl, for instance phenylcarbonyl;
aryloxycarbonyl;
aryl($C_1$-$C_4$)alkoxycarbonyl;
(di)($C_1$-$C_4$)(alkyl)aminocarbonyl, for instance dimethylaminocarbonyl;
($C_1$-$C_4$)(alkyl)arylaminocarbonyl;
SO$_3^-$; M$^+$ with M$^+$ representing an alkali metal such as sodium or potassium, or alternatively An or An'$^-$ of formula (I) or (II) and M$^+$ are absent;
optionally substituted aryl such as phenyl, dibenzosuberyl or 1,3,5-cycloheptatrienyl,
optionally substituted heteroaryl; especially including the following cationic or noncationic heteroaryl radicals comprising from 1 to 4 heteroatoms:
i) 5-, 6- or 7-membered monocyclic radicals such as furanyl or furyl, pyrrolyl or pyrryl, thiophenyl or thienyl, pyrazolyl, oxazolyl, oxazolium, isoxazolyl, isoxazolium, thiazolyl, thiazolium, isothiazolyl, isothiazolium, 1,2,4-triazolyl, 1,2,4-triazolium, 1,2,3-triazolyl, 1,2,3-triazolium, 1,2,4-oxazolyl, 1,2,4-oxazolium, 1,2,4-thiadiazolyl, 1,2,4-thiadiazolium, pyrylium, thiopyridyl, pyridinium, pyrimidinyl, pyrimidinium, pyrazinyl, pyrazinium, pyridazinyl, pyridazinium, triazinyl, triazinium, tetrazinyl, tetrazinium, azepine, azepinium, oxazepinyl, oxazepinium, thiepinyl, thiepinium, imidazolyl, imidazolium;
ii) 8- to 11-membered bicyclic radicals such as indolyl, indolinium, benzoimidazolyl, benzoimidazolium, benzoxazolyl, benzoxazolium, dihydrobenzoxazolinyl, benzothiazolyl, benzothiazolium, pyridoimidazolyl, pyridoimidazolium, thienocycloheptadienyl, these monocyclic or bicyclic groups being optionally substituted with one or more groups such as ($C_1$-$C_4$) alkyl, for instance methyl, or polyhalo($C_1$-$C_4$)alkyl, for instance trifluoromethyl;
optionally cationic, optionally substituted heterocycloalkyl, the heterocycloalkyl group especially represents a saturated or partially saturated 5-, 6- or 7-membered monocyclic group comprising from 1 to 4 heteroatoms chosen from oxygen, sulfur and nitrogen, such as di/tetrahydrofuranyl, di/tetrahydrothiophenyl, di/tetrahydropyrrolyl, di/tetrahydropyranyl, di/tetra/hexahydrothiopyranyl, dihydropyridyl, piperazinyl, piperidinyl, tetramethylpiperidyl, morpholinyl, di/tetra/hexahydroazepinyl, di/tetrahydropyrimidinyl, these groups being optionally substituted with one or more groups such as (C₁-C₄)alkyl, oxo or thioxo; or the heterocycle represents the following group:

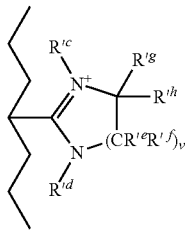

in which R'ᶜ, R'ᵈ, R'ᵉ, R'ᶠ, R'ᵍ and R'ʰ, which may be identical or different, represent a hydrogen atom or a (C₁-C₄)alkyl group, or alternatively two groups R'ᵍ with R'ʰ, and/or R'ᵉ with R'ᶠ, form an oxo or thioxo group, or alternatively R'ᵍ with R'ᵉ together form a cycloalkyl; and v represents an integer between 1 and 3 inclusive; preferentially, R'ᶜ to R'ʰ represent a hydrogen atom; and An'''⁻ represents a counterion;

isothiouronium;

—C(NR'ᶜR'ᵈ)=N⁺R'ᵉR'ᶠ; An''''⁻ with R'ᶜ, R'ᵈ, R'ᵉ and R'ᶠ, which may be identical or different, representing a hydrogen atom or a (C₁-C₄)alkyl group; preferentially, R'ᶜ to R'ᶠ represent a hydrogen atom; and An''''⁻ represents a counterion;

isothiourea;

—C(NR'ᶜR'ᵈ)=NR'ᵉ; with R'ᶜ, R'ᵈ and R'ᵉ as defined previously;

optionally substituted (di)aryl(C₁-C₄)alkyl such as 9-anthracenylmethyl, phenylmethyl or diphenylmethyl optionally substituted with one or more groups especially chosen from (C₁-C₄)alkyl, (C₁-C₄)alkoxy such as methoxy, hydroxyl, alkylcarbonyl or (di) (C₁-C₄)(alkyl) amino such as dimethylamino;

optionally substituted (di)heteroaryl(C₁-C₄)alkyl, the heteroaryl group especially being a cationic or noncationic, 5- or 6-membered monocyclic radical comprising from 1 to 4 heteroatoms chosen from nitrogen, oxygen and sulfur, such as pyrrolyl, furanyl, thiophenyl, pyridyl, pyridyl N-oxide such as 4-pyridyl or 2-pyridyl-N-oxide, pyrylium, pyridinium or triazinyl groups, optionally substituted with one or more groups such as alkyl, particularly methyl; advantageously, the (di)heteroaryl(C₁-C₄)alkyl is (di)heteroarylmethyl or (di)heteroarylethyl;

CR¹R²R³ with R¹, R² and R³, which may be identical or different, representing a halogen atom or a group chosen from:

(C₁-C₄)alkyl;

(C₁-C₄)alkoxy;

optionally substituted aryl such as phenyl optionally substituted with one or more groups, for instance (C₁-C₄)alkyl, (C₁-C₄)alkoxy or hydroxyl;

optionally substituted heteroaryl such as thiophenyl, furanyl, pyrrolyl, pyranyl or pyridyl, optionally substituted with a (C₁-C₄)alkyl group;

P(Z¹)R'¹R'²R'³ with R'¹ and R'², which may be identical or different, representing a hydroxyl, (C₁-C₄)alkoxy or alkyl group, R'³ representing a hydroxyl or (C₁-C₄) alkoxy group, and Z¹ representing an oxygen or sulfur atom;

a sterically hindered ring; and optionally substituted alkoxyalkyl, such as methoxymethyl (MOM), ethoxyethyl (EOM) and isobutoxymethyl.

One particular mode of the invention concerns the dyeing process in which the chromophore of the final product B—X'-A- derived from the precursors of formulae (I) and (II) contains a group X' that represents an imine, (poly)methine, styryl, azomethine or azo group; more particularly styryl.

The colorless dye precursors are chosen, for example, from:

the precursor (I) which represents [H₂N-A-L-S]ₓ—(Y)ᵧ, and the dye precursor (II) of formula B—C(G)-H to give the chromophore B—X'-A- which represents B—CH=N-A-, with G representing an oxygen or sulfur atom; this reaction is described, for example, in the literature: *J. Heterocyclic Chem.*, 44(3), 617-626, 2007;

the precursor (I) which represents [H—C(G)-A-L-S]ₓ—(Y)ᵧ, and the dye precursor (II) of formula B—NH₂ to give the chromophore B—X'-A- which represents B—N=CH-A-, with G as defined above; this reaction is described, for example, in the literature: *Huaxue shijie* 46(6), 352-3, 357, 2005;

the precursor (I) which represents [H₃C-A-L-S]ₓ—(Y)ᵧ, and the dye precursor (II) of formula B—C(G')- to give the chromophore B—X'-A- which represents B—CH=CH-A-, with G' representing an oxygen or sulfur atom or NH;

this reaction is known to those skilled in the art as the Knoevenagel reaction, which is detailed hereinbelow;

the precursor (I) which represents [H—C(G')-A-L-S]ₓ—(Y)ᵧ, and the dye precursor (II) of formula B—CH₃ to give the chromophore B—X'-A- which represents B—CH=CH-A-, with G' as defined above;

this reaction is described, for example, in the literature: *Chemische Berichte* 113(2), 457-70,1980; *J. Heterocyclic Chem.*, 16(8), 1583-7, 1979;

the precursor (I) which represents [G''-A-L-S]ₓ—(Y)ᵧ, and the nitroso-derived dye precursor (II) of formula B—NO to give the chromophore B—X'-A- which represents B—N=A'-, with A' representing an aryl or heteroaryl group derived from A, comprising an oxo function if G'' represents a hydroxyl group, or alternatively an imino group if G'' represents a (C₁-C₆)(alkyl)amino group;

this reaction is described, for example, in the literature: *J. Amer. Chem. Soc.*, 68, 2641-3, 1946; ibid 71, 3260-2, 1949; *Heterocycles* 12(3), 323-7, 1979;

the precursor (I) which represents a nitroso derivative [ON-A-L-S]ₓ—(Y)ᵧ, and the dye precursor (II) of formula B-G'' to give the chromophore B—X'-A-which represents B'=N-A-, with B' representing an aryl or heteroaryl group derived from B, comprising an oxo function if G'' represents a hydroxyl group, or alternatively an imino group if G'' represents a (C₁-C₆)(alkyl)amino group;

this reaction is described, for example, in the literature: *J. Amer. Chem. Soc.*, 68, 2641-3, 1946; ibid 71, 3260-2, 1949; *Heterocycles* 12(3), 323-7, 1979;

the precursor (I) which represents [G''-A-L-S]ₓ—(Y)ᵧ, and the dye precursor (II) of formula B—N₂⁺ to give the chromophore B—X'-A- which represents B—N=N-A with G'' representing a hydrogen atom;

this reaction is described, for example, in the literature: *Color Chemistry*, Ed. H. Zollinger ISBN 3-906390-23-3 pages 172-186;

the precursor (I) which represents [N₂⁺-A-L-S]ₓ—(Y)ᵧ, and the dye precursor (II) of formula B-G'' to give the chromophore B—X'-A- which represents B—N=N-A. G" represents a hydrogen atom;

this reaction is described in the literature: *Color Chemistry*, Ed. H. Zollinger ISBN 3-906390-23-3 pages 172-186;

the precursor (I) which represents [H—C(G)-A-L-S]$_x$—(Y)$_y$, and the dye precursor (II) of formula B—N(R)—NH$_2$ to give the chromophore B—X'-A- which represents B—N(R)—N=CH-A-, with G as defined above and R representing a hydrogen atom or a (polyhydroxy)(C$_1$-C$_4$)alkyl group;

this reaction is described in the literature: *J. Amer. Chem. Soc.*, 62,3522,1940; *Chemische Berichte* 95,562-70, 1962;

the precursor (I) which represents [H$_3$C-A-L-S]$_x$—(Y)$_y$, and the dye precursor (II) of formula B—N$_2^+$ to give the chromophore B—X'-A- which represents B—N(R)—N=CH-A-, with G' representing an oxygen or sulfur atom or NH and R as defined above;

this reaction is described in the literature: *Jpn Kokai TOKKYO Koho* 2001019866 23/01/2001; *Zhurnal Obshchei Khimii* 48(8), 1793-8, 1978; *Khimiko-farmatseuticheskii Zhurnal* 12(11), 48-53, 1978.

According to one particular embodiment of the invention, the dye precursors of formula (I) that are useful for the dyeing process according to the invention comprise:

either a group A representing an aryl group such as phenyl, naphthyl, indolyl or pyridyl, optionally substituted with a (C$_1$-C$_6$)alkyl, (C$_1$-C$_6$)alkoxy, (C$_1$-C$_6$)alkylthio, (di)(C$_1$-C$_6$)(alkyl)amino, (C$_1$-C$_6$)polyhaloalkyl, hydroxyl, (C$_1$-C$_6$)polyhydroxyalkyl, polyhydroxy(C$_1$-C$_6$)alkoxy, cyano, R-G-C(G')-, R—C(G')-G-, R'S(O)$_2$—N(R)—, RR'N—S(O)$_2$— group, with G or G', which may be identical or different, representing an oxygen or sulfur atom or a group NR', and R and R', which may be identical or different, representing a hydrogen atom or a (C$_1$-C$_6$)alkyl group, and in this case the group B of the precursor of formula (II) represents a cationic heteroaryl group such as imidazolium, pyridinium, quinolinium or indolinium optionally substituted with a (C$_1$-C$_6$)alkyl, (C$_1$-C$_6$)alkoxy, (C$_1$-C$_6$)alkylthio, (di) (C$_1$-C$_6$)(alkyl)amino, (C$_1$-C$_6$)polyhaloalkyl, hydroxyl, (C$_1$-C$_6$)polyhydroxyalkyl, polyhydroxy(C$_1$-C$_6$)alkoxy, cyano, R-G-C(G')-, R—C(G')-G-, R'S(O)$_2$—N(R)—, RR'N—S(O)$_2$— group with G or G', which may be identical or different, representing an oxygen or sulfur atom or a group NR', and R and R', which may be identical or different, representing a hydrogen atom or a (C$_1$-C$_6$)alkyl group;

or a group A representing a cationic heteroaryl group such as imidazolium, pyridinium, quinolinium or indolinium optionally substituted with a (C$_1$-C$_6$)alkyl, (C$_1$-C$_6$)alkoxy, (C$_1$-C$_6$)alkylthio, (di) (C$_1$-C$_6$)(alkyl)amino, (C$_1$-C$_6$)polyhaloalkyl, hydroxyl, (C$_1$-C$_6$)polyhydroxyalkyl, polyhydroxy(C$_1$-C$_6$)alkoxy, cyano, R-G-C(G')-, R—C(G')-G-, R'S(O)$_2$—N(R)—, RR'N—S(O)$_2$— group with G or G', which may be identical or different, representing an oxygen or sulfur atom or a group NR', and R and R', which may be identical or different, representing a hydrogen atom or a (C$_1$-C$_6$)alkyl group and in this case the group B of the precursor of formula (II) represents an aryl group such as phenyl, naphthyl, indolyl or pyridyl optionally substituted with a (C$_1$-C$_6$)alkyl, (C$_1$-C$_6$)alkoxy, (C$_1$-C$_6$)alkylthio, (di) (C$_1$-C$_6$)(alkyl)amino, (C$_1$-C$_6$)polyhaloalkyl, hydroxyl, (C$_1$-C$_6$)polyhydroxyalkyl, polyhydroxy(C$_1$-C$_6$)alkoxy, cyano, R-G-C(G')-, R—C(G')-G-, R'S(O)$_2$—N(R)—, RR'N—S(O)$_2$— group with G or G', which may be identical or different, representing an oxygen or sulfur atom or a group NR', and R and R', which may be identical or different, representing a hydrogen atom or a (C$_1$-C$_6$) alkyl group.

One particular embodiment concerns a dyeing process that consists in applying to keratin fibers, which have optionally been reduced beforehand, a colorless disulfide precursor containing activated methylene of formula (I$_2$) as defined previously; it being understood that the term "activated methylene" is considered as being a methylene group that is sufficiently nucleophilic to react with an electrophilic group and thus to form a bond allowing electron transfer from A to B and vice-versa;

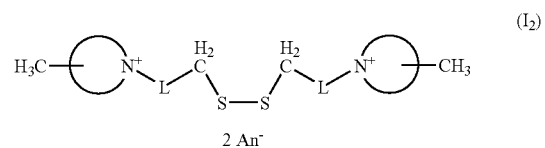

(I$_2$)

and a colorless aldehyde-based precursor of formula (II$_1$) below:

(II$_1$)

In which formula (II$_1$):

n represents 0 or 1;

Ar represents an optionally substituted aryl or heteroaryl group, particularly aryl such as phenyl optionally substituted with:

a C$_1$-C$_4$ alkyl group;

a hydroxyl group, a C$_1$-C$_4$ alkoxy group, a C$_2$-C$_4$ (poly)hydroxyalkoxy group;

an alkoxycarbonyl group (R$_a$O—C(O)—) in which R$_a$ represents a C$_1$-C$_4$ alkyl radical;

an alkylcarbonyloxy group (R$_a$C(O)—O—) in which R$_a$ represents a C$_1$-C$_4$ alkyl radical;

an amino group optionally substituted with one or more C$_1$-C$_4$ alkyl radicals, which may be identical or different, optionally bearing at least one hydroxyl group, the two alkyl radicals possibly forming with the nitrogen atom to which they are attached a substituted or unsubstituted 5- or 6-membered heterocycle optionally bearing another heteroatom identical to or different from nitrogen, for example oxygen;

an alkylcarbonylamino group (R$_a$C(O)—NR'$_a$—) in which R$_a$ represents a C$_1$-C$_4$ alkyl radical and R'$_a$ represents a hydrogen atom or a C$_1$-C$_4$ alkyl radical;

a (di-) (alkyl)aminocarbonyl group ((R$_a$)$_2$N—C(O)) in which the radicals R$_a$, independently of each other, which may be identical or different, represent a hydrogen atom or a C$_1$-C$_4$ alkyl radical;

a ureido group ((R$_a$)$_2$N—CO—NR$_b$—) in which the radicals R$_a$ and R$_b$, independently of each other, represent a hydrogen atom or a C$_1$-C$_4$ alkyl radical;

a halogen atom, preferably chlorine, fluorine or bromine.

Another particular embodiment of the invention concerns a process that consists in applying to keratin fibers, which have optionally been reduced beforehand, a colorless disulfide precursor containing an aldehyde function of formula ($I_1$)

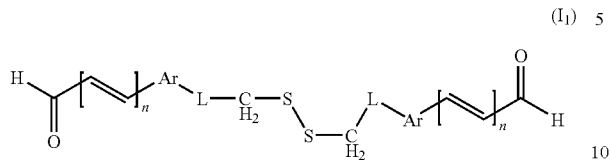

in which formula ($I_1$):
  Ar represents an optionally substituted arylene or heteroarylene group such as phenylene, naphthylene, pyridinylene or pyrazolene, and particularly phenylene;
  L is as defined previously; and a colorless precursor containing an activated methyl of formula ($II_2$) below:

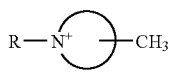

in which formula ($II_2$):
  R represents an optionally substituted ($C_1$-$C_6$)alkyl group;

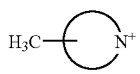

represents a 5- to 13-membered cationic heteroaryl group, possibly comprising, besides the cationic nitrogen atom, from 1 to 3 heteroatoms chosen from nitrogen, oxygen and sulfur, and which bears on a carbon atom a methyl group, such as pyridinium or quinolinium, the methyl group particularly being in position 2 or 4 of the pyridinium or of the quinolinium.

For example, the dyeing process may consist:
i) in a first stage, in applying a cosmetic composition comprising an aromatic dialdehyde disulfide compound belonging to the general formulae (I) and (II), of the following structure:

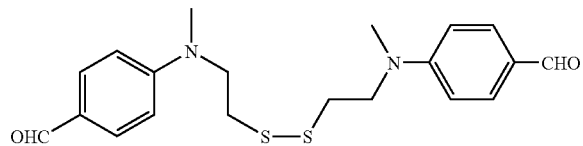

optionally of adding a fixing agent such as an oxidizing agent, to improve the fixing of the disulfide precursor to the keratin fibers which have optionally been reduced beforehand; and then
ii) of applying a composition comprising a precursor containing activated methylene belonging to formulae (II) and ($II_2$), such as 1,4-dimethyl pyridinium. This process may be represented schematically as follows:

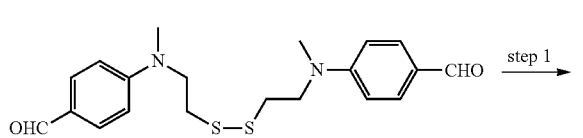

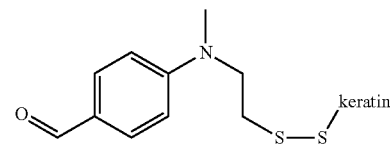

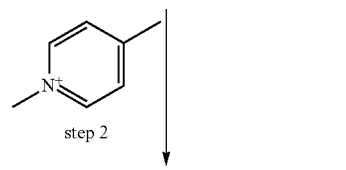

step 2

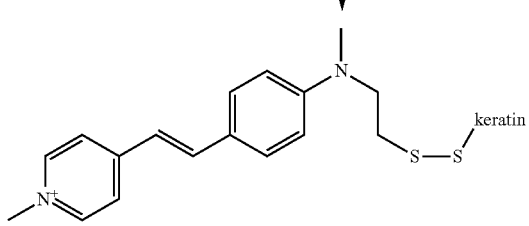

During the first step, the cosmetic composition comprising the colorless precursor belonging to formulae (I) and ($I_2$) is applied to keratin fibers, which are advantageously pre-reduced, and during step 2 the cosmetic composition comprising the colorless precursor belonging to formulae (II) and ($II_2$) is applied to the keratin fibers.

Another particular embodiment concerns a dyeing process that consists in applying to keratin fibers, which have optionally been reduced beforehand, a colorless heterocyclic disulfide precursor containing activated methylene of formula (I) with a colorless aldehyde-based precursor of formula (II).

For example, the dyeing process may consist:
i) in a first stage, in applying a cosmetic composition comprising a bispyridinium disulfide compound containing activated methylene belonging to the general formulae (I) and ($I_2$) of the following formula:

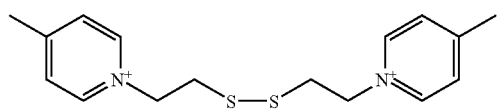

optionally of adding a fixing agent such as an oxidizing agent, to improve the fixing of the disulfide precursor to the keratin fibers which have optionally been reduced beforehand; and then
ii) of applying a composition comprising a precursor containing an aldehyde function belonging to formulae (II) and ($II_1$), such as 4-(N,N-dimethylamino)benzaldehyde. This process may be represented schematically as follows:

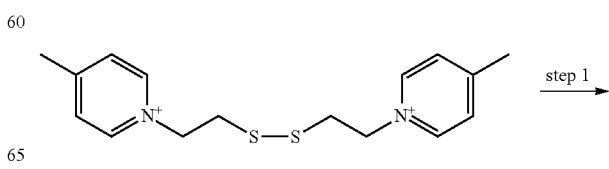

During the first step, the cosmetic composition comprising the colorless precursor belonging to formulae (I) and (I$_2$) is applied to keratin fibers, which are advantageously pre-reduced, and during step 2 the cosmetic composition comprising the colorless precursor belonging to formulae (II) and (II$_1$) is applied to the keratin fibers.

According to one particular embodiment in the process of the invention, a reducing agent may be applied to the keratin fibers as a pretreatment before application of the dye precursor of formula (I). This reducing agent may be chosen from thiols, for instance cysteine, homocysteine, thiolactic acid, salts of these thiols, phosphines, bisulfite, sulfites, thioglycolic acid, and also esters thereof, especially glyceryl monothioglycolate, and thioglycerol. This reducing agent may also be chosen from borohydrides and derivatives thereof, for instance salts of borohydride, of cyanoborohydride, of triacetoxyborohydride or of trimethoxyborohydride: sodium, lithium, potassium, calcium or quaternary ammonium (tetramethylammonium, tetraethylammonium, tetra-n-butylammonium or benzyltriethylammonium) salts; catecholborane.

This pretreatment may be of short duration, especially from 1 second to 30 minutes and preferably from 1 minute to 15 minutes, with a reducing agent as mentioned previously.

According to one variant, the reducing agent is added to the dye composition containing at least the colorless precursor of formula (I) at the time of use.

According to another variant, the reducing agent is applied as a post-treatment, after applying the dye composition containing at least the colorless precursor of formula (I). The duration of the post-treatment with the reducing agent may be short, for example from 0.1 second to 30 minutes and preferably from 1 minute to 15 minutes, with a reducing agent as described previously. According to one particular embodiment, the reducing agent is an agent of thiol or borohydride type as described previously.

When the dye precursor of formula (I) for which x and y are 1 comprises a protecting group Y for the thiol function, the process of the invention may be preceded by a deprotection step for restoring in-situ the SH function.

By way of example, it is possible to deprotect the function S—Y of the dyes of the invention with Y being a protecting group, by adjusting the pH as follows:

| Y: protecting group | deprotection |
|---|---|
| alkylcarbonyl, | pH > 9 |
| arylcarbonyl, | pH > 9 |
| alkoxycarbonyl, | pH > 9 |
| aryloxycarbonyl, | pH > 9 |
| arylalkoxycarbonyl | pH > 9 |
| (di) (alkyl) aminocarbonyl, | pH > 9 |
| (alkyl) arylaminocarbonyl | pH > 9 |
| optionally substituted aryl such as phenyl, | pH > 9 |
| 5-, 6- or 7-membered monocyclic heteroaryl such as oxazolium, | pH > 9 |
| 8- to 11-membered bicyclic heteroaryl such as benzoimidazolium or benzoxazolium | pH > 9 |

The deprotection step may also be performed during a step of pretreatment of the hair, for instance the hair reducing pretreatment.

One particular embodiment of the invention concerns a process in which the colorless thiol or thiol-protected precursor of formula (I) may be applied directly to the hair without reducing agents, free of pretreatment or post-treatment reducing agents.

A treatment with an oxidizing agent may optionally be combined. One particular embodiment of the invention concerns the process of dyeing keratin fibers according to the invention without the use of oxidizing agent. Any type of oxidizing agent that is conventional in the field may be used. Thus, it may be chosen from hydrogen peroxide, urea peroxide, alkali metal bromates, persalts such as perborates and persulfates, and also enzymes, among which mention may be made of peroxidases, 2-electron oxidoreductases such as uricases, and 4-electron oxygenases such as laccases. The use of hydrogen peroxide is particularly preferred. The leave-on time of the oxidizing agent may be between 1 second and 10 minutes.

The dye composition according to the invention is generally applied at room temperature. However, it may be applied at temperatures ranging from 20 to 180° C.

As indicated previously, another subject of the invention is the colorless disulfide dye precursor of formula (I$_1$) or (I$_2$), or a colorless thiol or thiol-protected dye precursor of formula (I$_3$), (I$_4$) or (I$_5$), with the exception of compounds (i) to (xxxiv) as defined previously.

According to one preferred variant of the invention, the precursors of formula (I) for which x=y=1, the radical Y represents a hydrogen atom or a group chosen from (C$_1$-C$_6$) alkylcarbonyl, particularly acetyl, optionally substituted arylcarbonyl, isothiourea or isothiouronium, the group is particularly a group C(NH$_2$)=NH or —C(=N$^+$H$_2$)NH$_2$; and SO$_3^-$.

One particular embodiment of the invention concerns the precursors of formula (I$_1$) for which Ar represents a phenylene group.

More particularly, these dye precursors are of formula (I$_6$):

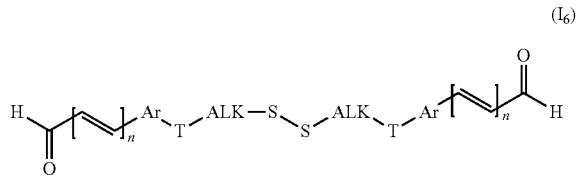

in which formula ($I_6$):

Ar represents a phenylene group such as: 1, 4 or 1,2-phenylene;

T represents an amino group NR or amido group —NR—C(O)— or —C(O)—NR— with R representing a hydrogen atom or a ($C_1$-$C_6$)alkyl group;

ALK represents a divalent $C_1$-$C_{10}$ alkylene chain, optionally interrupted with one or more divalent groups or combinations thereof chosen from: —N($R_a$)—; —N$^+$($R_a$)($R_b$)—, An$^-$; —CO— and with $R_a$ and $R_b$, which may be identical or different, chosen from a hydrogen and a ($C_1$-$C_6$)alkyl radical, and An$^-$ representing an anionic counterion, or ii) with a cationic heterocycle or cationic heteroaryl Het$^+$, An$^-$, with An$^-$ representing an anionic counterion and Het$^+$ representing a saturated or unsaturated 5- to 10-membered heterocycle, or a 5- to 10-membered heteroaryl such as imidazolium, piperazinium or piperidinium, with An$^-$ representing an anionic counterion, and n is 0.

One particular embodiment of the invention also concerns the precursors of formula ($I_2$) for which L represents a $C_1$-$C_{10}$ alkylene chain, particularly ethylene; optionally interrupted with a sulfonamide group.

More particularly, the compounds of formula ($I_2$) contain a group bearing an activated methylene

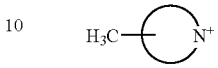

which represents a cationic heteroaryl group chosen from pyridinium, particularly 2- or 4-pyridinium, benzoxazolium, benzimidazolium, benzothiazolium, thiazolium, indolinium, indolyl and quinolinium, particularly 2- or 4-quinolinium.

Examples that may be mentioned include the precursors of formula (I), ($I_1$) or ($I_6$) below:

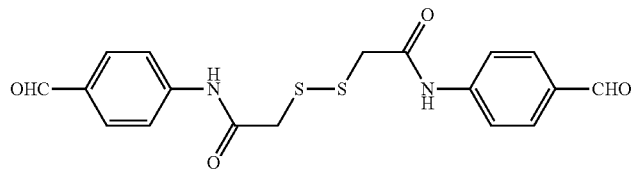

1

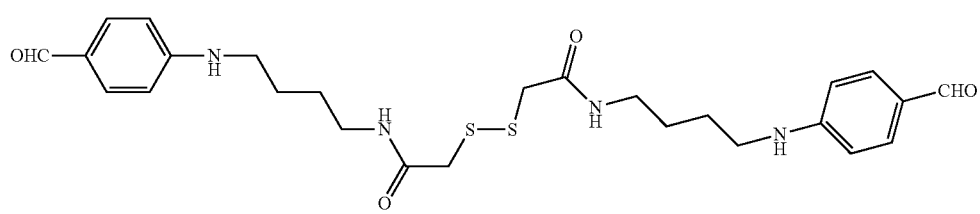

2

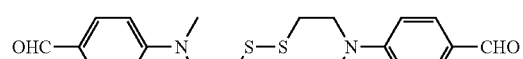

4

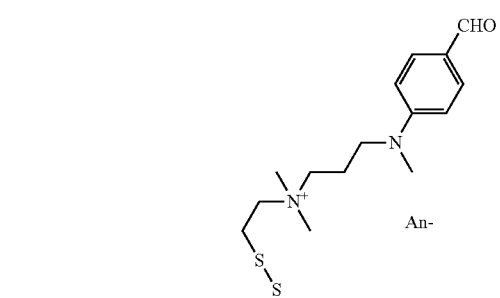

3

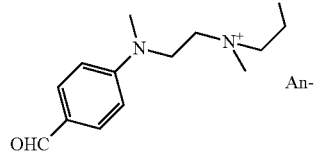

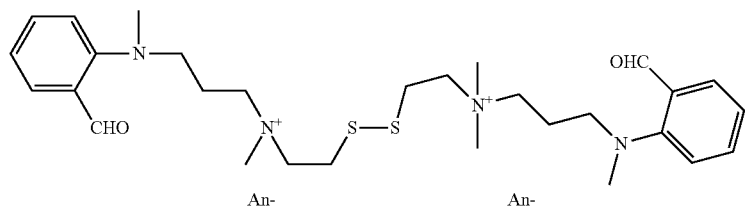

5

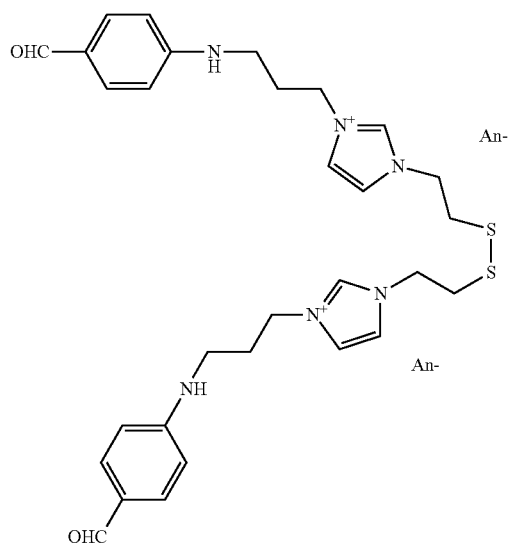
6
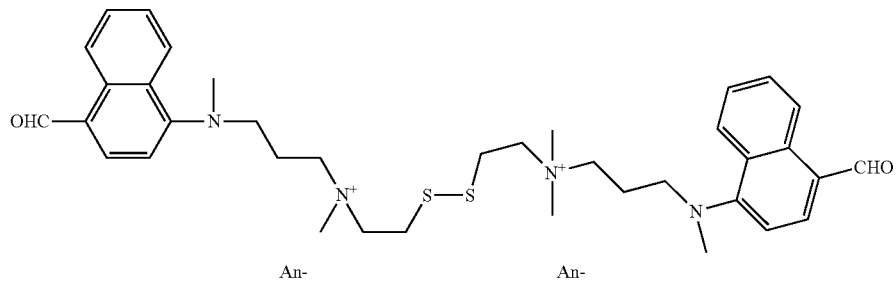
7
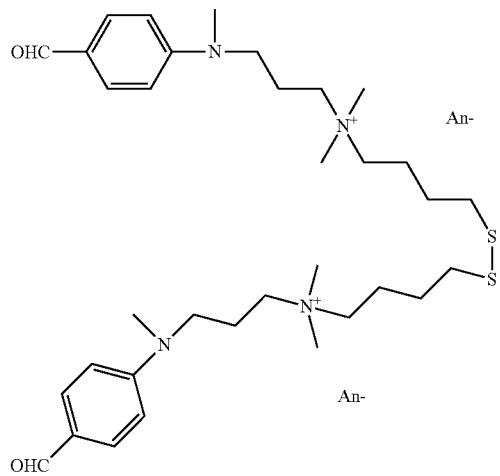
8
Examples that may be mentioned include the precursors of formula (I) or (I₂) below:
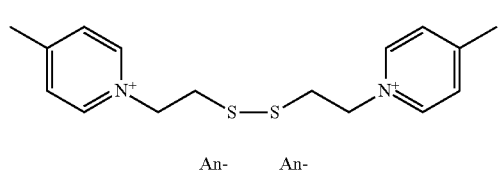
9
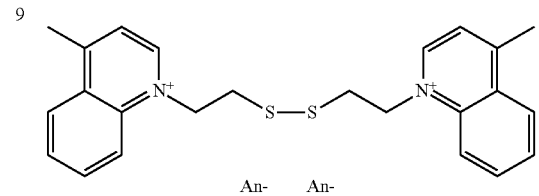
10

-continued
11
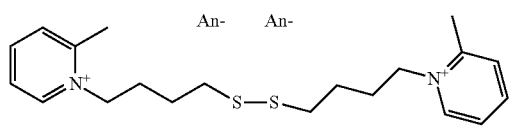
12
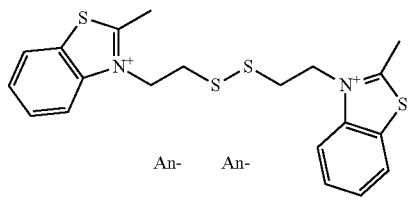
13
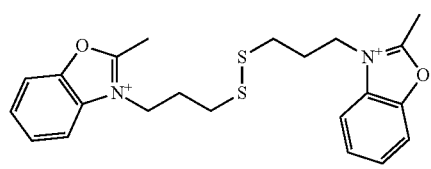
14
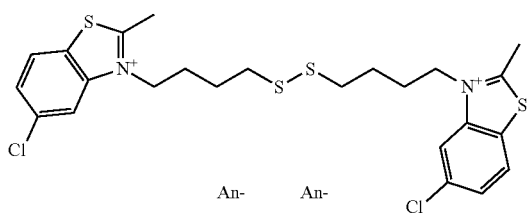
15
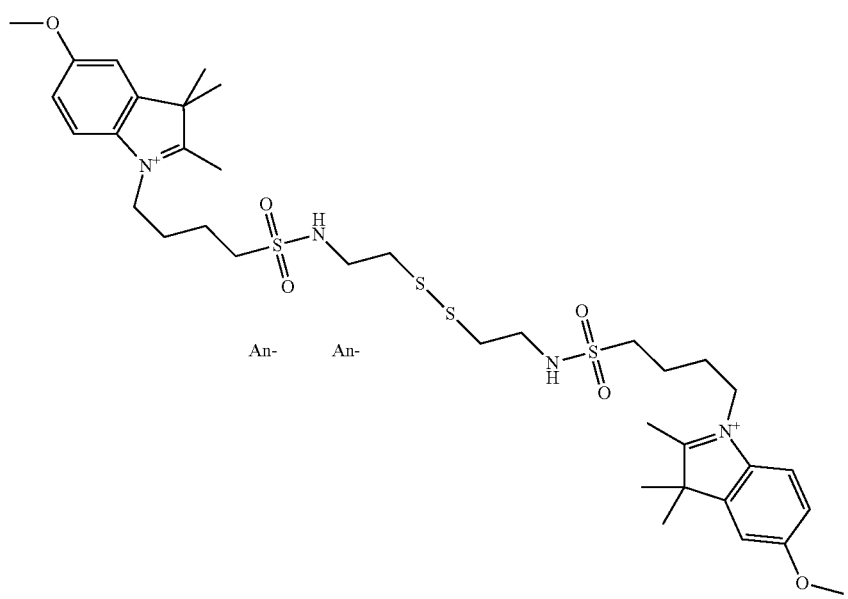
16
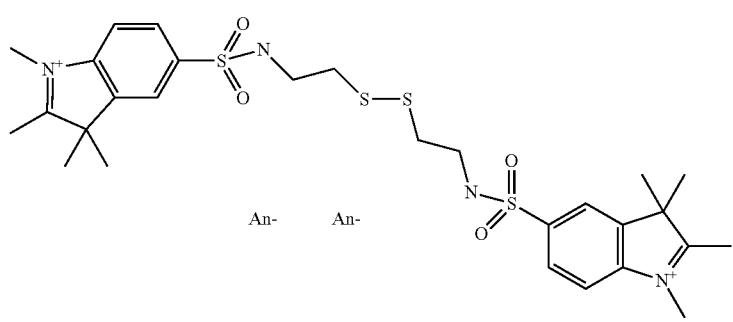
Examples that may be mentioned include the precursors of formula ($I_3$) or ($I_4$) below:
17
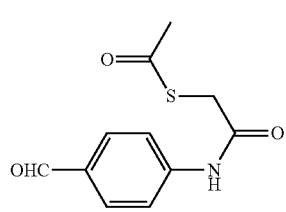
-continued
18
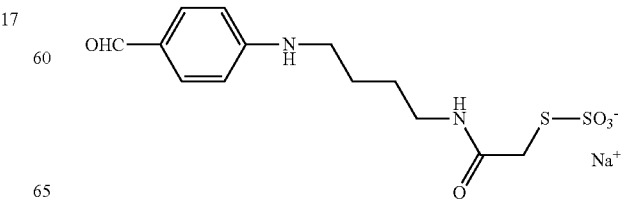

-continued

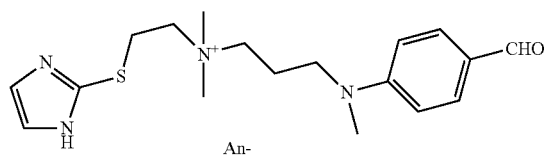

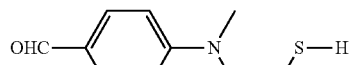

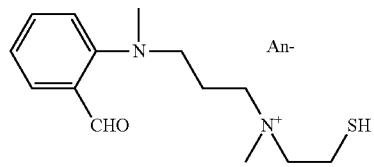

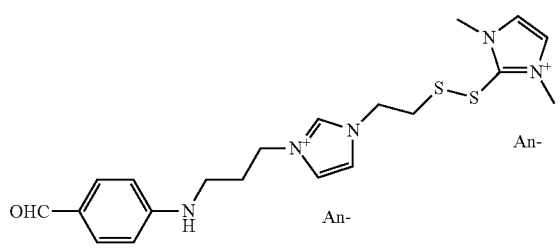

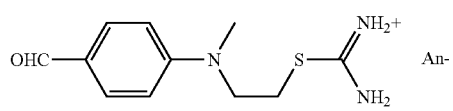

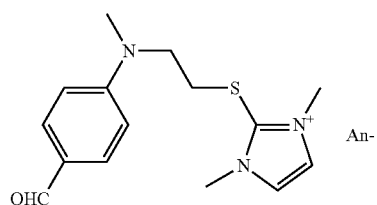

Examples that may be mentioned include the precursors of formula (I₅) below:

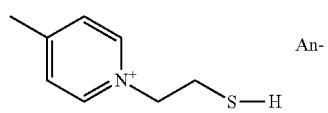

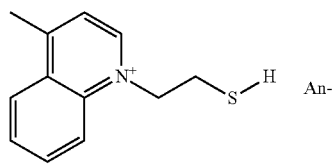

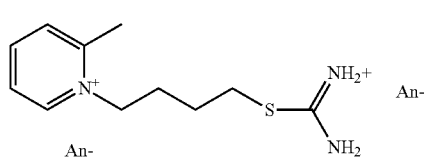

-continued

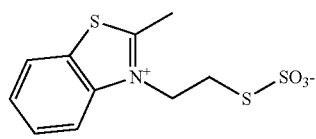

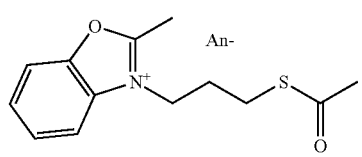

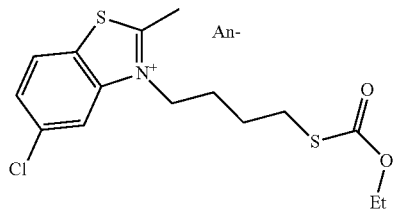

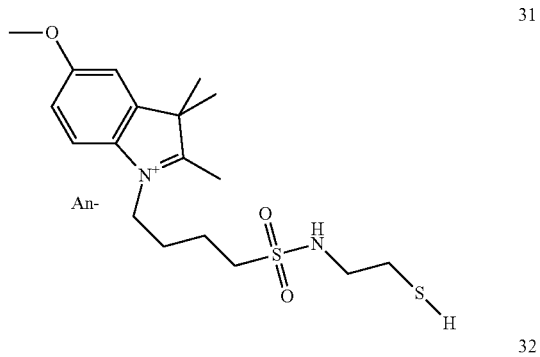

With An⁻ representing an anionic counterion.

Examples that may be mentioned include the precursors of formula (II), containing an electrophilic group, below:

Vanillin (4-hydroxy-3-methoxybenzaldehyde), isovanillin (3-hydroxy-4-methoxybenzaldehyde), 3,4-dihydroxy-benzaldehyde, 4-hydroxybenzaldehyde, 3,5-dimethoxy-4-hydroxybenzaldehyde, 4-hydroxybenzaldehyde, 4-dimethylaminobenzaldehyde, 4-methyl-5-imidazolecarboxaldehyde, 4-dimethyl-aminocinnamaldehyde, 4-hydroxy-2-methoxybenzaldehyde, 3,5-dimethyl-4-hydroxy-benzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxybiphenyl-1-carboxaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, indole-3-carboxaldehyde, benzene-1,4-dicarboxaldehyde, 4-ethoxybenzaldehyde, 2-methyl-1,4-naphthoquinone, 4-carboxybenzaldehyde, 4-hydroxy-3-methoxycinnamaldehyde, 3,5-dimethoxy-4-hydroxycinnamaldehyde, 3-methoxy-4-(1-pyrrolidinyl)benzaldehyde, 4-dimethylamino-3-methoxy-benzaldehyde, 1,2,-phthalaldehyde, pyrrole-2-aldehyde, thiophene-2-aldehyde, thiophene-3-aldehyde, chromone-3-carboxaldehyde, 6-methyl-4-oxo-1(4H)-benzopyran-3-carboxaldehyde, N-methylpyrrole-2-aldehyde, 5-methylfurfural, 6-hydroxychromene-3-carboxyaldehyde, 6-methylindole-3-carboxaldehyde, 4-dibutylamino-benzaldehyde, N-ethylcarbazole-3-aldehyde, 4-diethylamino-2-hydroxybenzaldehyde, 3,4-dimethoxy-5-hydroxybenzaldehyde, 5-[4-(dimethylamino)phenyl]-2,4-pentadienal, 2,3-thiophenecarboxaldehyde, 2,5-thiophenedicarboxaldehyde, 2-methoxy-1-naphthaldehyde, 3-ethoxy-4-hydroxybenzaldehyde.

These compounds react with the compounds of formula ($I_2$) or ($I_5$).

Examples that may be mentioned include the precursors of formula (II), containing a nucleophilic group, below:
1,4-dimethylquinolinium, 1,2-dimethylquinolinium, 1,4-dimethylpyridinium, 1,2-dimethylpyridinium, 2,4,6-trimethylpyrilium, 2-methyl-1-ethylquinolinium, 2,3-dimethylisoquinolinium, 1,2,3,3-tetramethyl-3H-indolium, 2,3-dimethylbenzothiazolium, 3-benzyl-2-benzothiazolium, 2-methyl-3-propylbenzothiazolium, 2,4-dimethyl-3-ethylthiazolium, 3-(2-carboxyethyl)-2,5-dimethylbenzothiazolium, 1,2,3-trimethyl-benz-imid-azolium, 5,6-dichloro-1,3-diethyl-2-methylbenz-imidazolium, 3-ethyl-2-methyl-benzothiazolium, 5-chloro-3-ethyl-2-methyl-benzothiazolium, 3-ethyl-2-methylbenzoxazolium salts, rhodanine; 2-methyl-3-(3-sulfopropyl)benzothiazolium hydroxide (inner salt), 4-methyl-1-(3-sulfopropyl)pyridinium hydroxide (inner salt), 4-methyl-1-(3-sulfo-propyl)-quinolinium hydroxide (inner salt), 5-methoxy-2-methyl-3-(3-sulfopropyl)benzothiazolium hydroxide (inner salt);

These compounds reacting with the compounds of formula ($I_1$) ($I_3$), ($I_4$) or ($I_6$).

The compounds of formula ($I_1$) may be especially obtained from similar preparation processes described, for example, in the documents *Justus Liebigs Annalen der Chemie* (1978), (7), 1123-8; ibid (1974), (5), 734-40; *Chemical Communications* (Cambridge) (1996), (10), 1193-1194 or *Organic Letters* (2000), 2(26), 4141-4144.

According to a first embodiment, the process for synthesizing the compounds of formula (IA used in the invention consists in performing the following step:

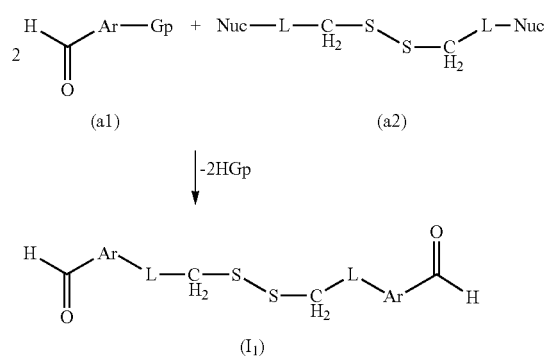

with Gp representing a leaving group such as halide, for instance bromide or chloride, a mesylate or a tosylate, L and Ar are as defined previously and Nuc representing a group of primary or secondary amine type or of alcohol type.

According to this process, a step of nucleophilic substitution (SNAr) of an arylaldehyde (a1) with a compound (a2) is performed in a manner known to those skilled in the art.

Certain reagents of type (a1) are commercial reagents. As a guide, mention may be made of 4-fluorobenzaldehyde, isonicotinaldehyde and 6-fluoronicotinic acid.

Certain reagents of type (a2) are commercial reagents. As a guide, mention may be made of cysteamine, N,N'-dimethylcysteamine and N,N,N',N'-tetramethylcystine.

This reaction usually takes place at a temperature of between 20° C. and 120° C. and preferably between 50° C. and 100° C. in the presence of a suitable solvent, among which mention may be made of water, alcohols, especially aliphatic alcohols containing up to 4 carbon atoms, dimethylformamide or N-methylpyrrolidinone.

The product may be isolated via the techniques known to those skilled in the art (precipitation, evaporation, chromatography, etc.).

Reference may be made to the book *Advanced Organic Chemistry*: Reactions, Mechanisms and Structures, J. March, 4th edition, John Wiley & Sons, 1992, for further details regarding the operating conditions used for the process mentioned above.

The compounds of formula ($I_2$) may especially be obtained via preparation processes similar to those described, for example, in the documents *Molecular Crystals and Liquid Crystals Science and Technology*, Section A: ibid (2002), 377, 137-140; *Journal of the American Chemical Society* (2004), 126(10), 3026-3027; *Chemistry Letters* (2006), 35(8), 870-871.

The process for synthesizing the compounds of formula ($I_2$) consists in performing the following step:

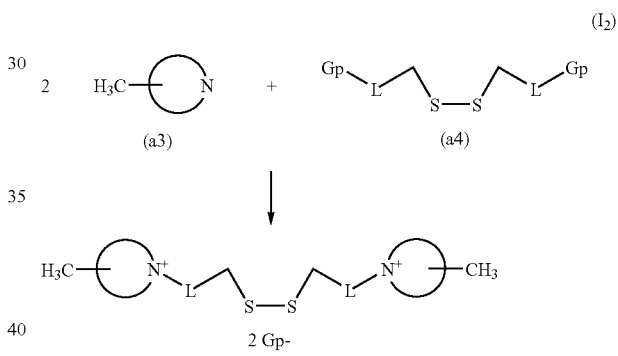

with Gp representing a leaving group such as a halide, for instance bromide or chloride, a mesylate or a tosylate. L, Ar and

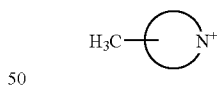

are as defined previously and Nuc represents a group of primary or secondary amine type or of alcohol type.

According to this process, a step of quaternization of a heterocycle (a3) is performed with a disulfide compound (a4) in a manner known to those skilled in the art.

Certain reagents of the type (a3) are commercial reagents. As a guide, mention may be made of 4-methylquinoline, 2-methylquinoline, 4-methylpyridine, 2-methylpyridine, 2-methylquinoline, 3-methylisoquinoline, 2,3,3-tetramethyl-3H-indole, 2-methyl-benzo-thiazole, 2,4-dimethylthiazole, 2,5-dimethylbenzothiazole, 1,2-dimethylbenzimidazole, 5,6-dichloro-1-ethyl-2-methylbenzimidazole, 5-chloro-2-methylbenzothiazole, 2-methylbenzoxazole salts, rhodanine; 5-methoxy-2-methylbenzothiazole.

The product may be isolated via techniques known to those skilled in the art (precipitation, evaporation, chromatography, etc.).

Usually, this reaction takes place at a temperature of between 20° C. and 120° C. and preferably between 50° C. and 100° C. in the presence of a suitable solvent, among which mention may be made of water, alcohols, especially aliphatic alcohols containing up to 4 carbon atoms, N,N-dimethylformamide or N-methylpyrrolidinone.

The disulfide compounds (a4) may be synchronized via the methods known to those skilled in the art. According to a first embodiment, the process for synthesizing the disulfide compounds (a4) may consist in performing a step of halogenation of a diol compound (a5) with reagents known to those skilled in the art, as follows:

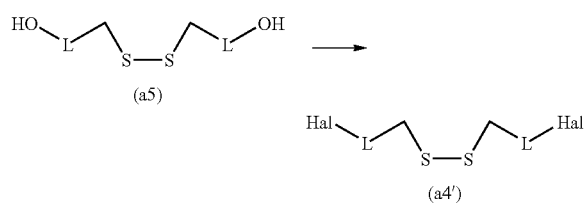

with L as defined previously; Hal representing a halide, for instance bromide or chloride.

The halogenating reagents may be chosen from thionyl chloride ($SOCl_2$) and phosphorus trichloride ($PCl_3$) as follows below:

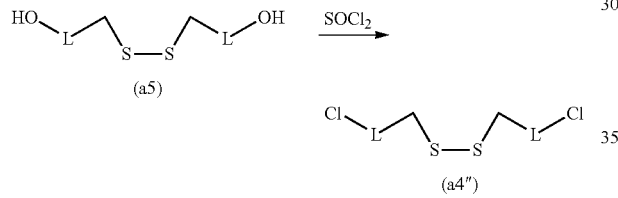

Usually, this reaction takes place at a temperature of between 20° C. and 120° C. and preferably between 50° C. and 100° C. in the presence of a suitable solvent, among which mention may be made of water, alcohols, especially aliphatic alcohols containing up to 4 carbon atoms, dimethylformamide or N-methylpyrrolidinone.

The products may be isolated via techniques known to those skilled in the art (precipitation, evaporation, chromatography, etc.).

According to another variant, the process for synthesizing the disulfide compounds (a4) may consist in performing a step of mesylation or tosylation of a diol compound (a5) with reagents known to those skilled in the art, as follows:

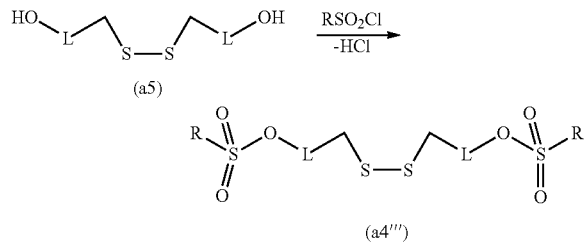

with R representing an alkyl or aryl radical such as methyl or 4-methylphenyl and L is as defined previously.

The thiol-protected compounds of formulae ($I_3$) and ($I_4$) for which x and y are 1 may be synthesized in two steps. The first step consists in preparing the unthiol-protected dye ($I_3'$) according to the methods known to those skilled in the art, for instance "*Thiols and organic Sulfides*", "*Thiocyanates and Isothiocyanates, organic*", Ullmann's Encyclopedia, Wiley-VCH, Weinheim, 2005. The second step consists in protecting the thiol function according to the standard methods known to those skilled in the art to give the thiol-protected dyes of formula ($I_3''$). As an example for protecting the thiol function —SH of the thiol dye, it is possible to use the methods in the books "*Protective Groups in Organic Synthesis*", T. W. Greene, published by John Wiley & Sons, NY, 1981, pp. 193-217; "*Protective Groups*", P. Kocienski, Thieme, 3rd edition, 2005, chapter 5. This method may be illustrated by the method consisting in i) generating the thiol dyes of formula ($I_3'$) via reduction of a dye containing two chromophores, bearing a disulfide function —S—S— such as ($I_1$) and ii) protecting according to the standard methods said thiol function of ($I_3'$) with the reagent 7 Y'R to gain access to the thiol-protected dyes of formula ($I_3''$). The thiol compound ($I_3'$) may also be metallated with an alkali metal or alkaline-earth metal Met* to give the thiolate dye of formula (($I_3'$-Met).

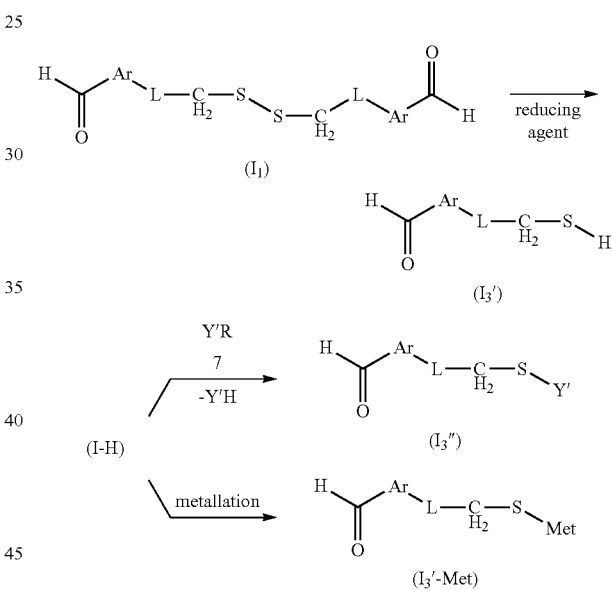

with Y' representing a protecting group for a thiol function; Met representing an alkali metal or alkaline-earth metal, particularly sodium or potassium, it being understood that when the metal is an alkaline-earth metal, 2 chromophores containing a thiolate function —S⁻ may be combined with 1 $Metal^{2+}$; L is as defined previously; and R represents a nucleofugal leaving group, for instance mesylate, tosylate, triflate or halide.

According to another possibility, a thiol-protected compound (a6) may be reacted with a protecting group Y' as defined previously prepared according to one of the procedures described in the books mentioned previously, said thiol-protected compound comprising at least one nucleophilic function with a sufficient amount, preferentially an equimolar amount, of a compound (a), the aldehyde function of which is protected, and which comprises an electrophilic function to form a covalent Σ bond; see below the preparation of dyes of formula ($I_3'''$):

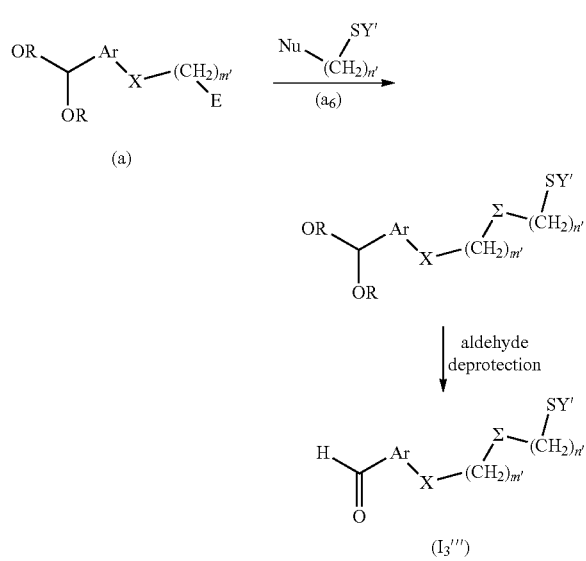

(a)

with Nu representing a nucleophilic group; E representing an electrophilic group; Σ the bond generated after attack of the nucleophile on the electrophile; m' and n' representing an integer between 1 and 6 inclusive with m'+n' between 2 and 10; R representing a $C_1$-$C_2$alkyl group, and together may form a 5-membered heterocycle.

By way of example, the covalent bonds or Σ bonding group that may be generated are listed in the table below, from condensation of electrophiles with nucleophiles:

| Electrophiles E | Nucleophiles Nu | Covalent bonds E |
|---|---|---|
| Activated esters* | Amines | Carboxamides |
| Acyl azides** | Amines | Carboxamides |
| Acyl halides | Amines | Carboxamides |
| Acyl halides | Alcohols | Esters |
| Acyl cyanides | Alcohols | Esters |
| Acyl cyanides | Amines | Carboxamides |
| Alkyl halides | Amines | Alkylamines |
| Alkyl halides | Carboxylic acids | Esters |
| Alkyl halides | Thiols | Thioesters |
| Alkyl halides | Alcohols | Ethers |
| Sulfonic acids and salts thereof | Thiols | Thioethers |
| Sulfonic acids and salts thereof | Carboxylic acids | Esters |
| Sulfonic acids and salts thereof | Alcohols | Ethers |
| Anhydrides | Alcohols | Esters |
| Anhydrides | Amines | Carboxamides |
| Aryl halides | Thiols | Thioethers |
| Aryl halides | Amines | Arylamines |
| Aziridines | Thiols | Thioethers |
| Carboxylic acids | Amines | Carboxamides |
| Carboxylic acids | Alcohols | Esters |
| Carbodiimides | Carboxylic acids | N-acylureas |
| Diazoalkanes | Carboxylic acids | Esters |
| Epoxides | Thiols | Thioethers |
| Haloacetamides | Thiols | Thioethers |
| Imide esters | Amines | Amidines |
| Isocyanates | Amines | Ureas |
| Isocyanates | Alcohols | Urethanes |
| Isothiocyanates | Amines | Thioureas |
| Maleimides | Thiols | Thioethers |
| Sulfonic esters | Amines | Alkylamines |
| Sulfonic esters | Thiols | Thioethers |

| Electrophiles E | Nucleophiles Nu | Covalent bonds E |
|---|---|---|
| Sulfonic esters | Carboxylic acids | Esters |
| Sulfonic esters | Alcohols | Ethers |
| Sulfonyl halides | Amines | Sulfonamides |

*the activated esters of general formula —CO-LG with LG representing a leaving group such as oxysuccinimidyl, oxybenzotriazolyl or aryloxy, optionally substituted;
**the acyl azides can rearrange to give isocyanates.

One variant to this process is to use a chromophore containing an electrophilic acrylate function (—OCO—C=C—) on which is performed an addition reaction that will generate a Σ bond.

It is also possible to use a thiol reagent (a7): Y'—SH comprising a group Y' as defined previously, the SH nucleophilic function of which can react on the carbon atom of the radical L alpha to the halogen atom borne by an arylaldehyde compound, to give the thiol-protected dye of formula ($I_3''$):

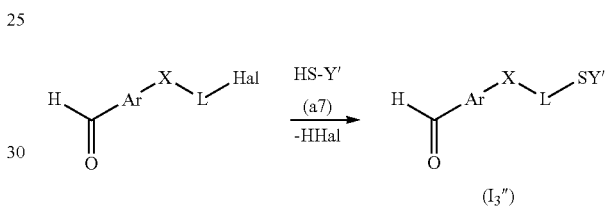

with Hal representing a nucleofugal halogen atom such as bromine, iodine or chlorine.

More particularly, a nucleofugal leaving group may be replaced with a thiourea group (S═C(NRR)NRR) to generate isothiouroniums. For example, if the thiourea group is a thioimidazolinium (a8), to give the dye S— protected with an imidazolium group ($I_3'''$):

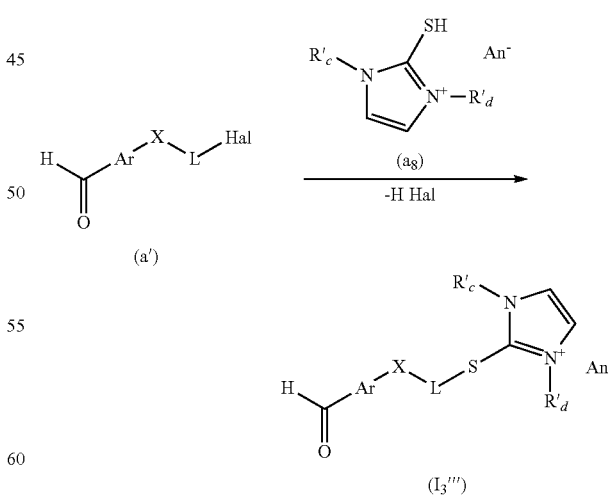

Another variant may allow access to compound ($I_3'''$): from a thioimidazole (a9), followed by alkylation of said thioimidazole using R'$_d$-Gp with Gp being a leaving group such as chloride, bromide or tosylate:

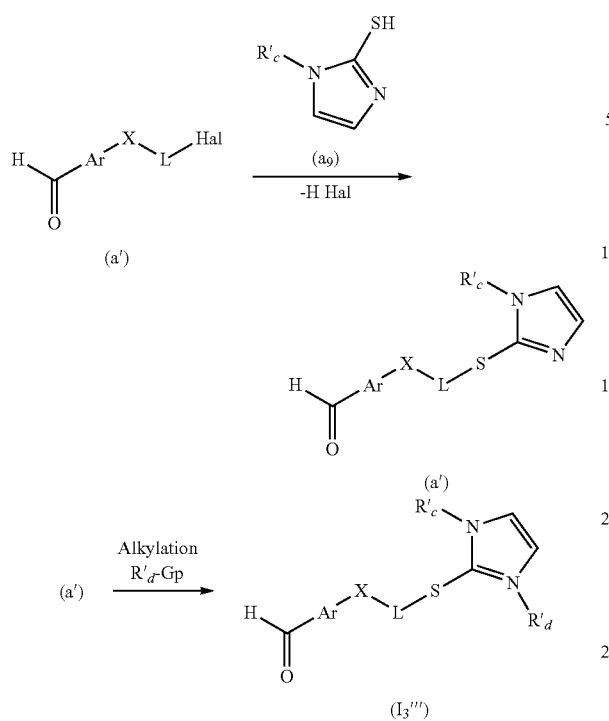

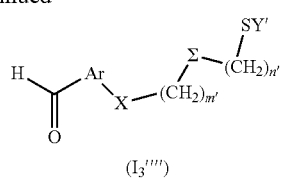

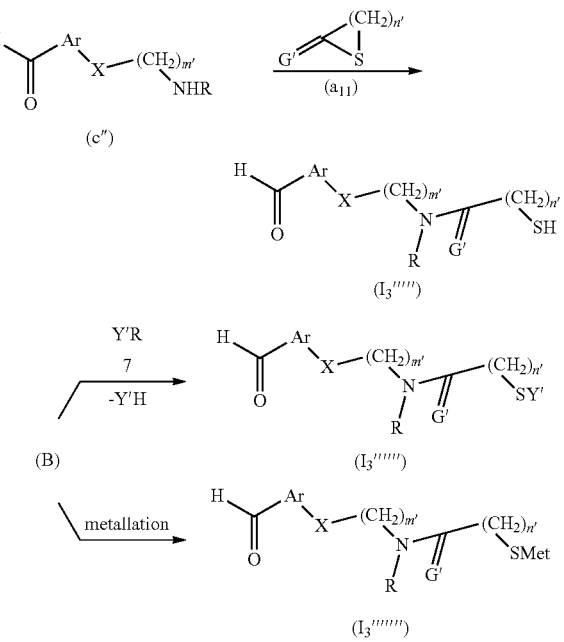

One variant is to use, instead of the halide comprising compound (a'), a compound comprising another type of nucleofuge such as tosylate or mesylate.

In accordance with another possibility, certain thiol-protected compounds ($I_3''''$) may be obtained by reacting a thiol-protected compound with a compound bearing two carboxylic acid functions activated according to the standard methods (for example reaction with a carbodiimide or with thionyl chloride). The resulting product (a10) is then reacted with a compound (c) bearing a nucleophilic function, for example of primary or secondary amine type, or of aliphatic alcohol type. Next, the aldehyde is regenerated by deprotection using the methods known to those skilled in the art.

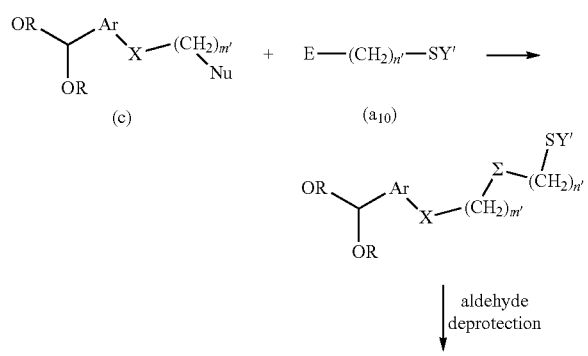

Another variant is to use a thiolactone derivative as represented by the scheme below:

with G' representing an oxygen or sulfur atom or a group NR' with R' representing a hydrogen atom or an alkyl radical, and R representing a hydrogen atom or a $C_1$-$C_4$ alkyl, $C_1$-$C_4$ hydroxyalkyl or aryl($C_1$-$C_4$)alkyl radical. The thiolactone derivative is preferentially chosen with n'=3 and G' represents an oxygen atom.

One synthetic variant is to react two equivalents of the nucleophilic reagent (c''') with a disulfide dielectrophilic reagent (j) it is possible to generate after condensation the disulfide compound (I'—S). After deprotection of the aldehydes, this compound may undergo a reduction to form the thiol compound (I'—H), which may be protected to form the thiol-protected dye (I''—Y) or may be metallated with an alkali metal to give the metallated compound ($II'''_{Metal}$)

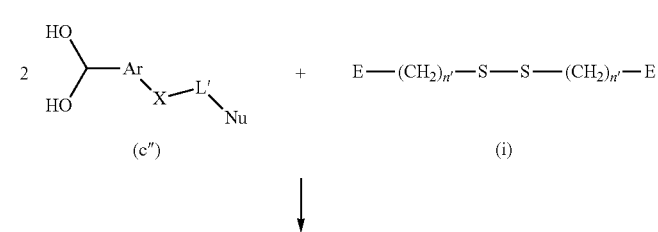

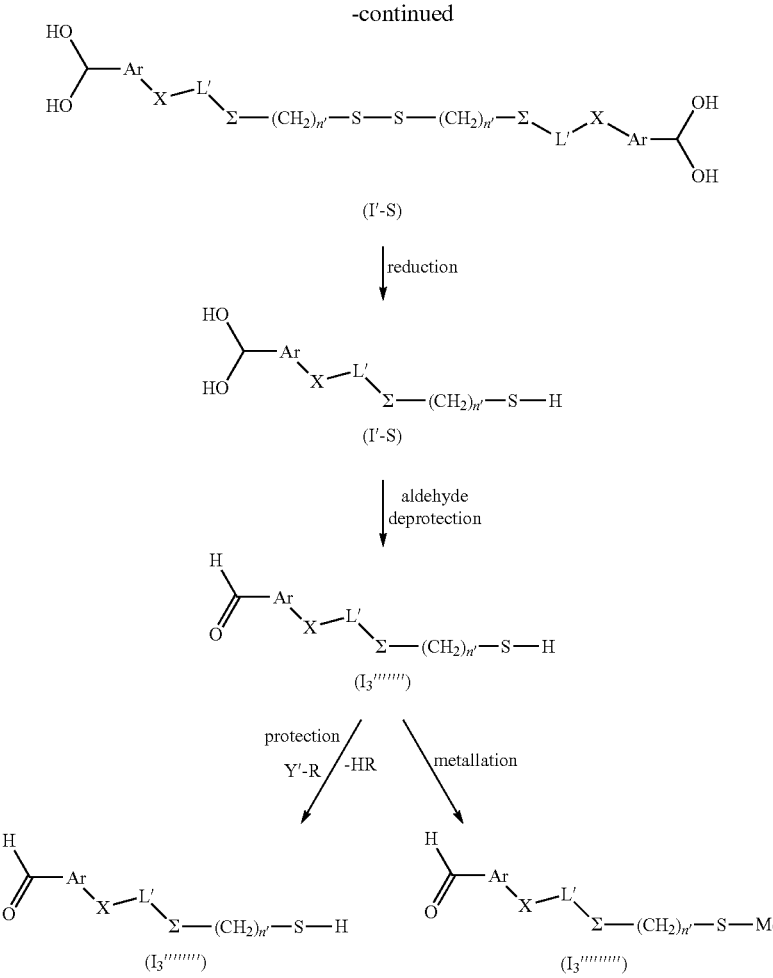

The thiol-protected disulfide compounds of formulae ($I_1$), ($I_3$) and ($I_4$) may be synthesized in two steps. The first steps consist in preparing disulfide ($I_{1\text{-}ald}$) or thiol-protected ($I_{4\text{-}ald}$) compounds via methods described above and according to the methods known to those skilled in the art, for instance "*Thiols and Organic Sulfides*", "*Thiocyanates and Isothiocyanates, Organic*", Ullmann's Encyclopedia, Wiley-VCH, Weinheim, 2005. The second step consists of a step of formylation of the aryl ring:

The step of formylation of the aryl ring is known to those skilled in the art as the Vilsmeier-Haak reaction. This process avoids the steps of protection and then deprotection of the aldehyde group in the processes described above.

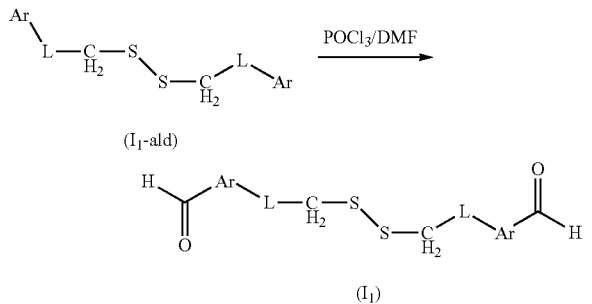

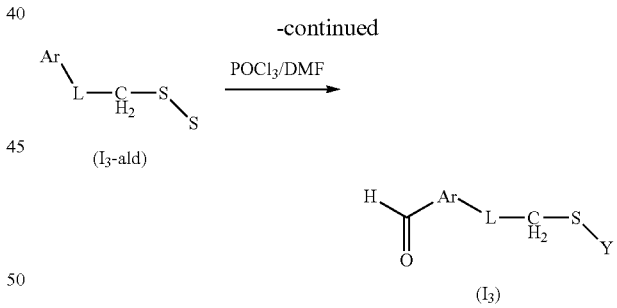

The compounds of formulae ($I_{1\text{-}ald}$) and ($I_{3\text{-}ald}$) may be obtained via the processes described above and known to those skilled in the art.

The compounds of formula ($I_5$) may especially be obtained by reduction of the disulfide group of compounds of the type ($I_2$)

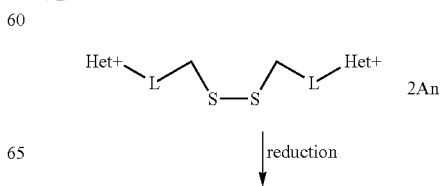

-continued

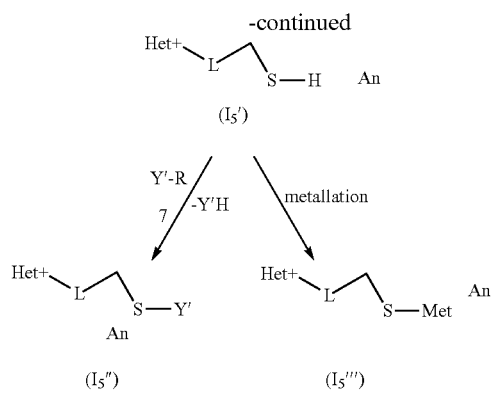

These synthetic processes have been described above.

One synthetic variant is to react one equivalent of a compound comprising a thiol-protected group and a leaving group (a12) with a heterocycle (a13) to give the compounds (I$_5$″)

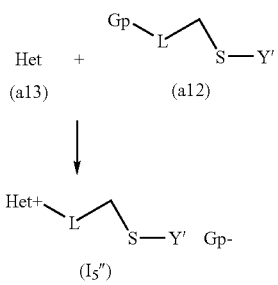

According to this process, a step of quaternization of a heterocycle (a13) with a thiol-protected compound (a12) is performed in a manner known to those skilled in the art.

Usually, this reaction takes place at a temperature of between 20° C. and 120° C. and preferably between 50° C. and 100° C. in the presence of a suitable solvent, among which mention may be made of water, alcohols, especially aliphatic alcohols containing up to 4 carbon atoms, dimethylformamide or N-methylpyrrolidinone.

The products may be isolated via the techniques known to those skilled in the art (precipitation, evaporation, chromatography, etc.).

Certain reagents of the type (a13) are commercial reagents. As a guide, mention may be made of 4-methylquinoline, 2-methylquinoline, 4-methylpyridine, 2-methylpyridine, 2-methylquinoline, 3-methylisoquinoline, 2,3,3-tetramethyl-3H-indole, 2-methylbenzothiazole, 2,4-dimethylthiazole, 2,5-dimethylbenzothiazole, 1,2-dimethylbenzimidazole, 5,6-dichloro-1-ethyl-2-methylbenzimidazole, 5-chloro-2-methylbenzothiazole, 2-methylbenzoxazole salts, rhodanine; 5-methoxy-2-methylbenzothiazole.

Another subject of the present invention is a cosmetic composition comprising at least one thiol or thiol-protected disulfide compound of formula (I$_1$), (I$_2$), (I$_3$), (I$_4$) or (I$_5$) as defined previously, said compound being different from compounds (i) to (xxviii) as defined previously.

The cosmetic compositions that are useful in the invention generally contain an amount of thiol or thiol-protected disulfide precursor of formula (I$_1$), (I$_2$), (I$_3$), (I$_4$) or (I$_5$) of between 0.001% and 50% relative to the total weight of the composition and preferably between 0.01% and 5% relative to the total weight of the composition.

The cosmetic medium that is suitable for dyeing, also known as the dye support, is a cosmetic medium generally containing water or a mixture of water and of at least one organic solvent. Examples or organic solvents that may be mentioned include C$_1$-C$_4$ lower alkanols, such as ethanol and isopropanol; polyols and polyol ethers, for instance 2-butoxyethanol, propyleneglycol, propyleneglycol monomethyl ether and diethyleneglycol monoethyl ether and monomethyl ether, and also aromatic alcohols, for instance benzyl alcohol or phenoxyethanol, and mixtures thereof.

When they are present, the solvents are preferably present in proportions preferably of between 1% and 99% by weight approximately and even more preferentially between 5% and 95% by weight approximately relative to the total weight of the dye composition.

The dye composition may also contain various adjuvants conventionally used in hair dye compositions, such as anionic, cationic, nonionic, amphoteric or zwitterionic surfactants or mixtures thereof, anionic, cationic, nonionic, amphoteric or zwitterionic polymers or mixtures thereof, mineral or organic thickeners, and in particular anionic, cationic, nonionic and amphoteric polymeric associative thickeners, antioxidants, penetrants, sequestrants, fragrances, buffers, dispersants, conditioning agents, for instance volatile or nonvolatile, modified or unmodified silicones such as amino silicones, film-forming agents, ceramides, preserving agents, opacifiers and conductive polymers.

The above adjuvants are generally present in an amount for each of them of between 0.01% and 20% by weight relative to the weight of the composition.

Needless to say, a person skilled in the art will take care to select this or these optional additional compound(s) such that the advantageous properties intrinsically associated with the dye composition in accordance with the invention are not, or are not substantially, adversely affected by the envisaged addition(s).

The pH of the dye composition is generally between 3 and 14 approximately and preferably between 5 and 11 approximately. It may be adjusted to the desired value by means of acidifying or basifying agents usually used in the dyeing of keratin fibers, or alternatively using standard buffer systems.

Among the acidifying agents that may be mentioned, for example, are mineral or organic acids, for instance hydrochloric acid, orthophosphoric acid or sulfuric acid, carboxylic acids, for instance acetic acid, tartaric acid, citric acid and lactic acid, and sulfonic acids.

Among the basifying agents that may be mentioned, for example, are aqueous ammonia, alkali metal carbonates, alkanolamines such as monoethanolamine, diethanolamine and triethanolamine, and also derivatives thereof, sodium hydroxide, potassium hydroxide and the compounds of formula (γ) below:

in which W$_a$ is a propylene residue optionally substituted with a hydroxyl group or a C$_1$-C$_4$ alkyl radical; R$_{a1}$, R$_{a2}$, R$_{a3}$ and R$_{a4}$, which may be identical or different, represent a hydrogen atom or a C$_1$-C$_4$ alkyl or C$_1$-C$_4$ hydroxyalkyl radical.

The dye compositions may be in various forms, such as in the form of a liquid, cream or gel, or in any other form that is suitable for dyeing keratin fibers, and especially the hair.

A subject of the invention is also a multi-compartment device or dyeing "kit" in which a first compartment contains a dye composition comprising at least one colorless disulfide/thiol precursor of formula (I) as defined previously and a second compartment contains a colorless precursor of formula (II) as defined previously. Optionally, the device also contains a compartment comprising a reducing agent capable of reducing the disulfide bridges of keratin fibers and/or capable of reducing the disulfide functions of the dye precursor (I) bearing a disulfide group when x=2 and y=0.

The invention also relates to a multi-compartment device in which a first compartment contains a colorless disulfide/thiol precursor of formula (I) as defined previously; a second compartment contains a colorless precursor of formula (II) as defined previously; a third compartment contains a reducing agent capable of reducing the disulfide bond of keratin materials and/or of the dye precursor (I) bearing a disulfide group when x=2 and y=0; and a fourth compartment contains an oxidizing agent.

Alternatively, the dyeing device contains a first compartment containing a dye composition which comprises at least one dye precursor (I) bearing a thiol-protected group with x=1 and y=1, a second compartment containing a colorless precursor of formula (II) as defined previously; a third compartment containing an agent capable of deprotecting the thiol-protected of formula (I) to release the thiol, and optionally a fourth compartment comprising an oxidizing agent.

Each of the devices mentioned above may be equipped with a means for applying the desired mixture to the hair, for instance the devices described in patent FR 2 586 913.

The examples that follow serve to illustrate the invention without, however, being limiting in nature. The dyes in the examples hereinbelow were fully characterized by the standard spectroscopic and spectrometric methods.

The examples that follow illustrate the invention without, however, limiting its scope.

EXAMPLE OF SYNTHESIS

Example 1

Synthesis of 1,1'-(Disulfanediyldiethane-2,1-diyl)bis(4-methylpyridinium) dimethanesulfonate

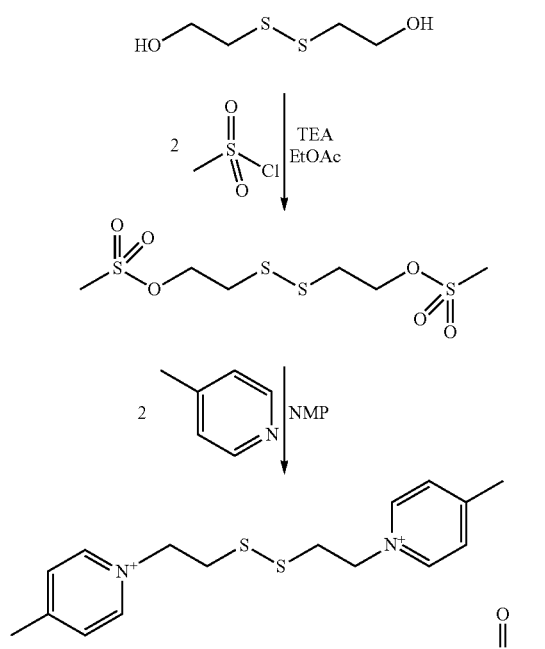

Procedure

Step 1: Synthesis of Disulfanediyldiethane-2,1-Diyl Dimethanesulfonate 10 g of 2,2'-dithiodiethanol and 14.44 g of triethylamine (TEA) are diluted in 100 mL of ethyl acetate (EtOAc). At 0° C., 16.35 g of methanesulfonyl chloride diluted in 35 mL of EtOAc are added dropwise to the reaction medium with rapid stirring. 7.22 g of TEA are introduced and stirring is continued at room temperature for 4 hours 30 minutes. 8.2 g of methanesulfonyl chloride are added dropwise at 15° C. and stirring is continued at room temperature for 17 hours. The precipitate is filtered off and washed with three times 50 mL of EtOAc. The organic phases are extracted with 100 mL of ice-water, 100 mL of water, three times 50 mL of saturated sodium hydrogen carbonate solution ($NaHCO_3$), twice 20 mL of saturated sodium chloride solution (NaCl), and then dried over anhydrous sodium sulfate ($Na_2SO_4$). The EtOAc is evaporated off, and 17.49 g of a clear pale yellow oil are collected and stored at −25° C. The analyses indicate that the product is in accordance and pure.

Step 2: Synthesis of 1,1'-(Disulfanediyldiethane-2,1-Diyl)Bis(4-Methylpyridinium) Dimethanesulfonate 3.51 g of 4-picoline and 5 g of disulfanediyldiethane-2,1-diyl dimethanesulfonate are diluted in 5 mL of N-methylpyrrolidinone (NMP) and then heated at 80° C. with stirring for 2 hours. Stirring is continued at room temperature for 17 hours. The reaction medium is made up with 50 mL of ethyl acetate and then filtered, washed with three times 100 mL of EtOAC and dried under vacuum over $P_2O_5$. 7.29 g of brown powder are collected. The analyses indicate that the product is in accordance and pure.

Example 2

Synthesis of 2-[(4-Formylphenyl)(Methyl)-Amino]Ethyl Imidothiocarbamate

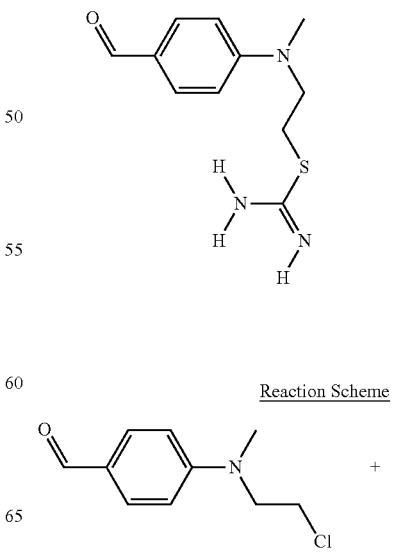

Reaction Scheme

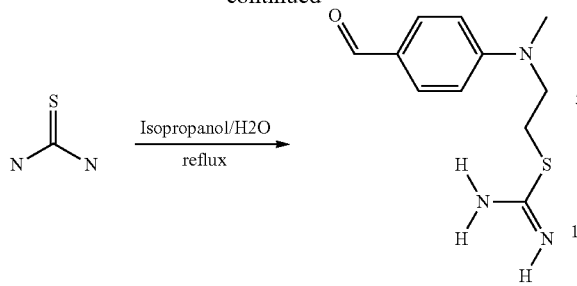

Procedure

In a three necked reaction flask was introduced 4-[(2-chloroethyl)(methyl)amino]benzaldehyde (2 g-commercial product), thiourea (770 mg), 2-Propanol (12 mL) and water (0.1 mL). The mixture was refluxed for 18 h then allowed to cool to ambient. Ethanol (10 mL) was added then the reaction mix was added to acetone (100 mL). The precipitate was collected by filtration then dried under vacuum (905 mg). The analyses indicate that the product is in accordance.

LC-MS analysis: $\lambda_{max}$ at 346 nm and m/z of 238.

EXAMPLES OF DYEING

I) Compositions 1 to 4 Comprising the Dye Precursors of Formulae (I) and (II) Versus the Comparative

| Compositions | 1 | 2 | 3 | 4 |
|---|---|---|---|---|
| Reducing agent Dolce vital DV2 ®- L'Oréal | 10 g | | | |
| 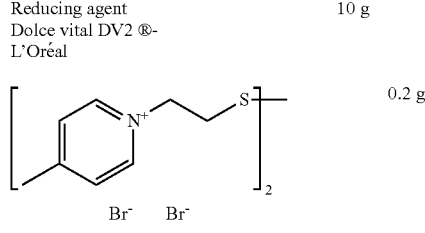 INVENTION | | 0.2 g | | |
| 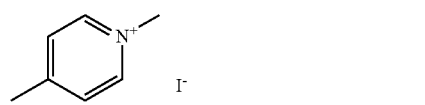 N-methyl-4-picolinium iodide COMPARATIVE | | | 0.4 g | |
| 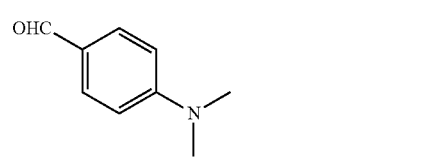 4-(N,N-dimethylamino)benzaldehyde | | | | 1.0 g |
| Ethanol | | | | 30g |
| Pyrrolidine | | | | 10g |
| Demineralized water qs | 100 g | 100 g | 100 g | 100 g |

Example 1

Dyeing of the Invention

Composition 1 was applied to a lock of grey hair containing 90% natural grey (NG) hairs and permanent-waved grey (PWG) hairs, at room temperature (about 20° C.). The leave-on time after application is 15 minutes. The lock is rinsed with water. Composition 2 is then applied to this lock, comprising the colorless disulfide precursor according to the invention, with a leave-on time after application of 30 minutes. The lock is then rinsed with water and rinsed water is uncolored. A composition 4 is then applied to this lock, comprising the other colorless precursor according to the invention. The leave-on time after application is 30 minutes. The lock is rinsed with water and then air-dried.

We observed that the dyeing and rinsing liquors are not colored.

Example 2

Dyeing with the Comparative

Composition 1 was applied to a lock of grey hair at room temperature (about 20° C.). The leave-on time after application is 15 minutes. The lock is rinsed with water. Composition 3 is then applied to this lock, comprising the non-disulfide precursor of the comparative, with a leave-on time after application of 30 minutes. The lock is then rinsed with water, and a composition 4 is then applied to this lock, comprising the other colorless precursor according to the invention. The leave-on time after application is 30 minutes. The lock is rinsed with water and then air-dried.

It is observed that the dyeing and rinsing liquors are colored.

Shampooing

The locks thus dyed are subjected to a wash-fastness test, which consists in performing five shampoo washes (with a standard shampoo) and in evaluating the color after these five shampoo washes.

It is found that, for Example 1, the rinsing liquors are not colored. On the other hand, for the comparative, the liquors are always colored after the fifth shampoo wash.

After dyeing, the color of the locks is measured with a Minolta CM2600d spectrocolorimeter (specular components included, 10° angle, illuminant D65) in the CIEL*a*b* system. In this system, L* represents the intensity of the color, a* indicates the green/red color axis and b* the blue/yellow color axis.

ΔE represents the variation in color between a lock of "pre-shampooed" hair and a lock of "post-shampooed" dyed hair, and is determined from the following formula:

$$\Delta E = \sqrt{(L^* - L_o^*)^2 + (a^* - a_o^*)^2 + (b^* - b_o^*)^2}$$

in which L*, a* and b* represent the values measured on the "pre-shampooed" lock and $L_o^*$, $a_o^*$ and $b_o^*$ represent the values measured on the "post-shampooed" lock.

The colorimetric results obtained are given in the table below.

|          | L*   | a*   | b*   | ΔE   |
|----------|------|------|------|------|
| Invention |      |      |      |      |
| Example 1: "pre-shampooing"  | 51.7 | 55.5 | 63.3 |      |
| Example 1: "post-shampooing" | 50.0 | 58.0 | 63.9 | 3.1  |
| Comparative |      |      |      |      |
| Example 2: "pre-shampooing"  | 55.0 | 59.9 | 70.5 |      |
| Example 2: "post-shampooing" | 65.1 | 43.5 | 71.3 | 19.3 |

These results show that the dyeing of the invention (Example 1) makes it possible to obtain improved dyeing in terms of shampoo fastness relative to the comparative composition (Example 2).

II) Comparative Disulfide Dye Vs. Invention 2-[(4-Formyl-Phenyl)(Methyl)Amino]-Ethyl Imidothiocarbamate with N-Methyl Picolinium Iodide II-1) Invention: The Following Solutions were Prepared Solution A

| 2-[(4-formylphenyl)(methyl)amino]ethyl imidothiocarbamate | 0.5 g |
|---|---|

[structure of 2-[(4-formylphenyl)(methyl)amino]ethyl imidothiocarbamate]

| Benzyl alcohol | 4 g |
| PEG 6OE | 6 g |
| Hydroxyethylcellulose | 0.7 g |
| Alkylpolyglucoside in water (65% active material) | 4.5 g |
| Water deionised | qsp 100 g |

Solution B

[structure of N-methyl picolinium iodide] 1 g

N-methyl picolinium iodide

| Benzyl alcohol | 4 g |
| PEG 6O | 6 g |
| Hydroxyethylcellulose | 0.7 g |
| Alkylpolyglucoside in water (65% active material) | 4.5 g |
| Water deionised | qsp 100 g |

Solution C

| Ethanol | 30 g |
| Pyrrolidine | 10 g |

Dyeing Method and Results for Invention

Solution A (5 g) was applied to 90% grey natural hair (0.5 g) for 30 minutes. The hair was rinsed with water. There is no change of color concerning the treated hair and the subsequent rinsed water is totally uncolored. Then solution B (5 g) was applied for 15 minutes. The hair was rinsed with water again. Coloration appears on hair treated and the rinsed subsequent water is totally uncolored. Solution C (10 g) was applied to the hair for 30 minutes. The hair was rinsed with water, the water still uncolored. Then hair are shampooed five times then dried. The mousse is uncolored.

The hair was colored bright orange and was resistance to shampooing (no visual colorless after 5 shampooings)

The dyeing was repeated with dark brown hair to give hair that was visibly lighter in color without noting any coloration of rinsed water. The hair remained visibly lighter even after 5 shampoos.

II-2) Comparative

Fluorescent dye according to prior art is the following:

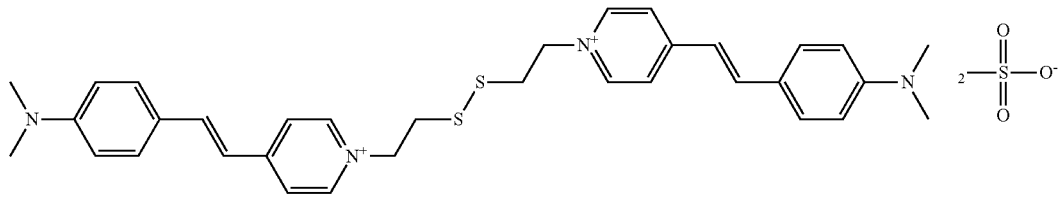

The following solutions were prepared as comparative
Solution A'

| | 0.38 g |
|---|---|
| [chemical structure: bis(dimethylamino-phenyl-vinyl-pyridinium-ethyl) disulfide with methylsulfonate counterion] | |

| | |
|---|---|
| Benzyl alcohol | 4 g |
| PEG 6OE | 6 g |
| Hydroxyethylcellulose | 0.7 g |
| Alkylpolyglucoside in water (65% active material) | 4.5 g |
| Water deionised | qsp 100 g |

Solution B'

| | 50 mg |
|---|---|
| [chemical structure: bis(dimethylamino-phenyl-vinyl-pyridinium-ethyl) disulfide with methylsulfonate counterion] | |

| | |
|---|---|
| methanol | 10 g |
| Lauryl ethyl sulfate solution (10% in water at pH 9.5) | 6 g |

Solution C' (Commercial)
Reducing agent (Dolce vital DV2®-ammonium thioglycolate)
Solution D'
Hydrogen peroxide (20 vol)
Dyeing Method and Results for Comparative
Method 1

Solution A' (5 g) of the comparative was applied to 90% grey natural hair (0.5 g) for 30 minutes. The hair was colored bright orange. During rinsing the water was colored orange. During 5 subsequent shampooings the mousse was colored orange becoming progressively less on each shampooing.

Solution B' (5 g) was applied to 90% grey natural hair (0.5 g) for 30 minutes. The hair was colored bright orange. During rinsing the water was significantly colored orange. During 5 subsequent shampooings the mousse was colored orange becoming progressively less on each shampooing.
Method 2

Solution C' (10 g) was applied to 90% grey natural hair (0.5 g) for 10 minutes. The hair was rinsed then solution A' (5 g) was applied for 20 minutes. The hair was rinsed (rinse water was colored) then solution D' (5 g) was added for 10 minutes. On rinsing the hair the rinse water was slightly colored. During subsequent shampooings the mousse became progressively less colored until after 4 shampoos the rinsed water was no longer colored.

The invention claimed is:
1. A process for dyeing keratin fibers, comprising applying to said fibers, which have optionally been pretreated with at least one reducing agent:
  i) a cosmetically acceptable composition comprising at least one colorless thiol/disulfide dye precursor of formula (I):

[Z-A-L-S]$_x$—(Y)$_y$  formula (I):

and
  ii) a cosmetically acceptable composition comprising at least one colorless dye precursor of formula (II):

B—X  formula (II):

wherein B of the at least one colorless dye precursor of formula (II) reacts chemically with A of the at least one colorless thiol/disulfide dye precursor of formula (I) to form a colored or a colored and fluorescent chromophore B—X'-A-;
wherein, in formula (I) and formula (II):
  x is 0 or 1;
  y is 1 or 2;
  L is chosen from optionally substituted divalent $C_1$-$C_{20}$ hydrocarbon-based chains, optionally interrupted and/or optionally terminated at one end with at least one group chosen from:
    i) divalent groups chosen from: —N($R_a$)—; —N$^+$($R_a$) ($R_b$)—An$^-$; —O—; —S—; —CO— and —SO$_2$—, with $R_a$ and $R_b$, independently of one another, each chosen from hydrogen, ($C_1$-$C_6$) alkyl groups, hydroxy ($C_1$-$C_6$) alkyl groups, and (di)($C_1$-$C_6$) (alkyl) amino ($C_1$-$C_6$) alkyl groups, and An$^-$ chosen from anionic counterions, and
    ii) cationic heterocyclic and heteroaryl Het$^+$An$^-$ groups, with An$^-$ chosen from anionic counterions and Het$^+$ chosen from saturated and unsaturated 5- to 10-membered heterocycles and saturated and unsaturated 5- to 10-membered heteroaryl groups;
A and B, independently of one another, are each chosen from colorless chromophores;

X and Z, independently of one another, are each chosen from chemical functional groups capable of reacting together to form a group X';

X' is chosen from chains that allow electron transfer between chromophore A and chromophore B;

Y is chosen from:
  i) hydrogen;
  ii) alkali metals;
  iii) alkaline-earth metals;
  iv) ammonium groups $N^+R^\alpha R^\beta R^\gamma R^\delta$ $An''^-$ and phosphonium groups $P^+R^\alpha R^\beta R^\gamma R^\delta$ $An''^-$, with $R^\alpha$, $R^\beta$, $R^\gamma$, and $R^\delta$, independently of one another, each chosen from hydrogen and $(C_1\text{-}C_4)$alkyl groups, and $An''^-$ chosen from anionic counterions; and
  v) protecting groups for a thiol function;

it being understood that when y is 2, then x is zero, and when x is 1, then y is 1.

2. The dyeing process according to claim 1, wherein X and Z are chosen from chemical functional groups capable of reacting together to form a group X' chosen from imine groups, (poly)methine groups, styryl groups, azomethine groups, and azo groups.

3. The dyeing process according to claim 1, wherein the at least one colorless thiol/disulfide precursor of formula (I) and the at least one colorless dye precursor of formula (II) are chosen from:

precursors (I) of formula $[H_2N\text{-}A\text{-}L\text{-}S]_x\text{—}(Y)_y$, and precursors (II) of formula B—C(G)—H to give a chromophore B—X'-A- of formula B—CH=N-A-, with G chosen from oxygen and sulfur;

precursors (I) of formula $[H\text{—}C(G)\text{-}A\text{-}LS]_x\text{—}(Y)_y$, and precursors (II) of formula B—NH$_2$ to give a chromophore B—X'-A- of formula B—N=CH-A-, with G chosen from oxygen and sulfur;

precursors (I) of formula $[H_3C\text{-}A\text{-}L\text{-}S]_x\text{—}(Y)_y$, and precursors (II) of formula BC(G')- to give chromophore B—X'-A- of formula B—CH=CH-A-, with G' chosen from oxygen, sulfur, and NH;

precursors (I) of formula $[H\text{—}C(G')\text{-}A\text{-}LS]_x\text{—}(Y)_y$, and precursors (II) of formula B—CH$_3$ to give a chromophore B—X'-A- of formula B—CH=CH-A-, with G' chosen from oxygen, sulfur, and NH;

precursors (I) of formula $[G''\text{-}A\text{-}L\text{-}S]_x(Y)_y$, and precursors (II) of formula B—NO to give a chromophore B—X'-A of formula B—N=A'-, with A' chosen from aryl and heteroaryl groups derived from A, comprising an oxo function if G" is a hydroxyl group or alternatively an imino group if G" is chosen from $(C_1\text{-}C_6)$(alkyl)amino groups;

precursors (I) of formula $[ON\text{-}A\text{-}L\text{-}S]_x\text{—}(Y)_y$, and precursors (II) of formula B-G" to give a chromophore B—X'-A- of formula B'=N-A-, with B' chosen from aryl and heteroaryl groups derived from B, comprising an oxo function if G" is a hydroxyl group or alternatively an imino group if G" is chosen from $(C_1\text{-}C_6)$(alkyl)amino groups;

precursors (I) of formula $[G''\text{-}A\text{-}L\text{-}S]_x\text{—}(Y)_y$, and precursors (II) of formula B—N$_2^+$ to give a chromophore B—X'-A- of formula B—N=N-A, with G" chosen from hydrogen;

precursors (I) of formula $[N_2^+\text{-}A\text{-}L\text{-}S]_x\text{—}(Y)_y$, and precursors (II) of formula B-G" to give a chromophore B—X'-A- of formula B—N=N-A, with G" chosen from hydrogen;

precursors (I) of formula $[H\text{—}C(G)\text{-}A\text{-}LS]_x\text{—}(Y)_y$, and precursors (II) of formula B—N(R)—NH$_2$ to give a chromophore B—X'-A- of formula B—N(R)—N=CH-A-, with G chosen from oxygen and sulfur and R chosen from hydrogen and (polyhydroxy)$(C_1\text{-}C_4)$alkyl groups;

precursors (I) of formula $[H_3C\text{-}A\text{-}L\text{-}S]_x\text{—}(Y)_y$, and precursors (II) of formula B—N$_2^+$ to give a chromophore B—X'-A- of formula B—N(R)—N=CH-A-, with G' chosen from oxygen, sulfur, and NH, and R is chosen from hydrogen and (polyhydroxy)$(C_1\text{-}C_4)$alkyl groups.

4. The dyeing process according to claim 3, wherein the precursors (I) comprise:

a group A chosen from aryl groups optionally substituted with at least one group chosen from $(C_1\text{-}C_6)$alkyl groups, $(C_1\text{-}C_6)$alkoxy groups, $(C_1\text{-}C_6)$alkylthio groups, (di)$(C_1\text{-}C_6)$(alkyl)amino groups, $(C_1\text{-}C_6)$ polyhaloalkyl groups, hydroxyl groups, $(C_1\text{-}C_6)$polyhydroxyalkyl groups, polyhydroxy$(C_1\text{-}C_6)$alkoxy groups, cyano groups, R-G-C(G')- groups, R—C(G')-G- groups, R'S(O)$_2$—N(R)— groups, and RR'N—S(O)$_2$— groups, with G or G', independently of one another, each chosen from oxygen, sulfur, and groups NR', and R and R', independently of one another, each chosen from hydrogen and $(C_1\text{-}C_6)$alkyl groups, and in this case the group B of the precursors (II) are chosen from cationic heteroaryl groups optionally substituted with at least one group chosen from $(C_1\text{-}C_6)$alkyl groups, $(C_1\text{-}C_6)$alkoxy groups, $(C_1\text{-}C_6)$alkylthio groups, (di)$(C_1\text{-}C_6)$(alkyl)amino groups, $(C_1\text{-}C_6)$ polyhaloalkyl groups, hydroxyl groups, $(C_1\text{-}C_6)$polyhydroxyalkyl groups, polyhydroxy$(C_1\text{-}C_6)$alkoxy groups, cyano groups, R-G-C(G')- groups, RC(G')-G- groups, R'S(O)$_2$—N(R)— groups, and RR'N—S(O)$_2$— groups, with G or G', independently of one another, each chosen from oxygen, sulfur, and groups NR', and R and R', independently of one another, each chosen from hydrogen and $(C_1\text{-}C_6)$alkyl groups; or a group A chosen from cationic heteroaryl groups optionally substituted with at least one group chosen from $(C_1\text{-}C_6)$alkyl groups, $(C_1\text{-}C_6)$alkoxy groups, $(C_1\text{-}C_6)$alkylthio groups, (di)$(C_1\text{-}C_6)$(alkyl)amino groups, $(C_1\text{-}C_6)$ polyhaloalkyl groups, hydroxyl, $(C_1\text{-}C_6)$polyhydroxyalkyl groups, polyhydroxy$(C_1\text{-}C_6)$alkoxy groups, cyano groups, R-G-C(G')- groups, R—C(G')-G- groups, R'S(O)$_2$—N(R)— groups, and RR'N—S(O)$_2$— groups, with G or G', independently of one another, each chosen from oxygen, sulfur, and groups NR', and R and R', independently of one another, each chosen from hydrogen and $(C_1\text{-}C_6)$alkyl groups, and in this case the group B of the precursors (II) are chosen from aryl groups optionally substituted with at least one group chosen from $(C_1\text{-}C_6)$alkyl groups, $(C_1\text{-}C_6)$alkoxy groups, $(C_1\text{-}C_6)$alkylthio groups, (di)$(C_1\text{-}C_6)$(alkyl)amino groups, $(C_1\text{-}C_6)$ polyhaloalkyl groups, hydroxyl groups, $(C_1\text{-}C_6)$polyhydroxyalkyl groups, polyhydroxy$(C_1\text{-}C_6)$alkoxy groups, cyano groups, R-G-C(G')- groups, R—C(G')-G- groups, R'S(O)$_2$—N(R)— groups, and RR'N—S(O)$_2$— groups, with G or G', independently of one another, each chosen from oxygen, sulfur, and groups NR', and R and R', independently of one another, each chosen from hydrogen and $(C_1\text{-}C_6)$alkyl groups.

5. The dyeing process according to claim 1, comprising applying to the keratin fibers:
  i) at least one colorless disulfide precursor comprising activated methylene of formula (I$_2$):

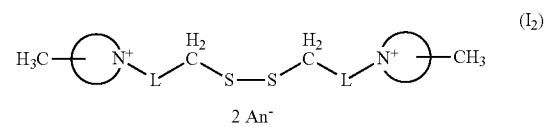

wherein, in formula (I₂):

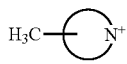

is chosen from 5- to 13-membered cationic heteroaryl groups, which may comprise, besides the cationic nitrogen, 1 to 3 heteroatoms chosen from nitrogen, oxygen, and sulfur, and which bears on a carbon atom a methyl group;

L is chosen from optionally substituted divalent $C_1$-$C_{20}$ hydrocarbon-based chains, optionally interrupted and/or optionally terminated at one end with at least one group chosen from:

i) divalent groups chosen from: —N($R_a$)—; —N⁺($R_a$)($R_b$)— An⁻; —O—; —S—; —CO— and —SO₂—, with $R_a$ and $R_b$, independently of one another, each chosen from hydrogen, ($C_1$-$C_6$)alkyl groups, hydroxy($C_1$-$C_6$)alkyl groups, and (di)($C_1$-$C_6$)(alkyl)amino($C_1$-$C_6$)alkyl groups, and An⁻ is chosen from anionic counterions, and ii) cationic heterocyclic and heteroaryl Het⁺An⁻ groups, with An⁻ chosen from anionic counterions, and Het⁺ chosen from saturated and unsaturated 5- to 10-membered heterocycles and saturated and unsaturated 5- to 10-membered heteroaryl groups; and ii) at least one colorless aldehyde-based precursor of formula (II₁):

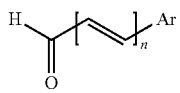

wherein, in formula (II₁):
n is 0 or 1;
Ar is chosen from aryl and heteroaryl groups optionally substituted with at least one group chosen from:
$C_1$-$C_4$ alkyl groups;
hydroxyl groups;
$C_1$-$C_4$ alkoxy groups;
$C_2$-$C_4$ (poly)hydroxyalkoxy groups;
alkoxycarbonyl groups ($R_a$O—C(O)—) in which $R_a$ is chosen from $C_1$-$C_4$ alkyl groups;
alkylcarbonyloxy groups ($R_a$C(O)—O—) in which $R_a$ is chosen from $C_1$-$C_4$ alkyl groups;
amino groups optionally substituted with at least one $C_1$-$C_4$ alkyl group, independently of one another, optionally bearing at least one hydroxyl group, the two alkyl groups possibly forming with the nitrogen atom to which they are attached a substituted or unsubstituted 5- or 6-membered heterocycle optionally bearing another heteroatom identical to or different from nitrogen;
alkylcarbonylamino groups ($R_a$C(O)—NR'$_a$—) in which $R_a$ is chosen from $C_1$-$C_4$ alkyl groups and R'$_a$ is chosen from hydrogen and $C_1$-$C_4$ alkyl groups;
(di)(alkyl)aminocarbonyl groups (($R_a$)₂N—C(O)) in which $R_a$, independently of each other, which may be identical or different, are chosen from hydrogen and $C_1$-$C_4$ alkyl groups;
ureido groups (($R_a$)₂N—C(O)—NR$_b$—) in which $R_a$ and $R_b$, independently of each other, are each chosen from hydrogen and $C_1$-$C_4$ alkyl groups; and
halogens.

6. The dyeing process according to claim 5, wherein the at least one colorless disulfide precursor comprising activated methylene of formula (I₂) comprises a group L chosen from $C_1$-$C_{10}$alkylene chains.

7. The dyeing process according to claim 1, comprising applying to the keratin fibers:
i) at least one colorless disulfide precursor comprising at least one aldehyde functional group of formula (I₁)

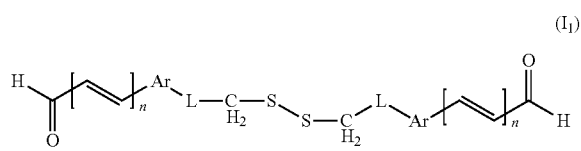

wherein, in formula (I₁):
Ar is chosen from optionally substituted arylene groups and optionally substituted heteroarylene groups;
L is chosen from optionally substituted divalent $C_1$-$C_{20}$ hydrocarbon-based chains, optionally interrupted and/or optionally terminated at one end with at least one group chosen from:

i) divalent groups chosen from: —N($R_a$)—; —N⁺($R_a$)($R_b$)— An⁻; —O—; —S—; —CO— and —SO₂—, with $R_a$ and $R_b$, independently of one another, each chosen from hydrogen, ($C_1$-$C_6$)alkyl groups, hydroxy($C_1$-$C_6$)alkyl groups, and (di)($C_1$-$C_6$)(alkyl)amino($C_1$-$C_6$)alkyl groups, and An⁻ chosen from anionic counterions, and ii) cationic heterocyclic and heteroaryl Het⁺An⁻ groups, with An⁻ chosen from anionic counterions and Het⁺ chosen from saturated and unsaturated 5- to 10-membered heterocycles and saturated and unsaturated 5- to 10-membered heteroaryl groups; and ii) at least one colorless precursor comprising an activated methyl of formula (II₂):

wherein, in formula (II₂):
R is chosen from hydrogen and ($C_1$-$C_6$)alkyl groups;

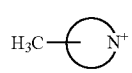

is chosen from 5- to 13-membered cationic heteroaryl groups, which may comprise, besides the cationic nitrogen, 1 to 3 heteroatoms chosen from nitrogen, oxygen, and sulfur, and which bears on a carbon atom a methyl group.

8. The dyeing process according to claim 1, wherein the at least one colorless precursor comprising an aldehyde functional group has formula (I₆):

(I₆)

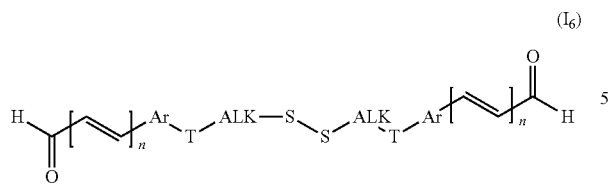

wherein, in formula (I₆):
Ar is chosen from phenylene groups;
T is chosen from amino groups NR, amido groups —NR—C(O)—, and amido groups —C(O)—NR—, with R chosen from hydrogen and $(C_1-C_6)$alkyl groups;
ALK is chosen from divalent $C_1-C_{10}$alkylene chains, optionally interrupted and/or optionally terminated at one with at least one group chosen from i) divalent groups chosen from: —N($R_a$)—; —N⁺($R_a$)($R_b$)— An⁻; and —C(O)—, with $R_a$ and $R_b$, independently of one another, each chosen from hydrogen and $(C_1-C_6)$ alkyl groups, and An⁻ chosen from anionic counterions, and ii) cationic heterocycle or cationic heteroaryl Het⁺An⁻ groups, with An⁻ chosen from anionic counterions and Het⁺ chosen from saturated and unsaturated 5- to 10-membered heterocycles and saturated and unsaturated 5- to 10-membered heteroaryls, and
n is 0.

9. The dyeing process according to claim 1, comprising:
i) in a first stage, applying a cosmetic composition comprising at least one aromatic dialdehyde disulfide compound having the following structure:

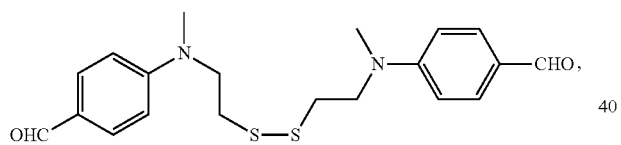

optionally adding a fixing agent; and then
ii) applying a composition comprising 1,4-dimethylpyridinium.

10. The dyeing process according to claim 1, wherein the keratin fibers have been pretreated with at least one reducing agent chosen from thiols, homocysteine, thiolactic acid, phosphines, bisulfate, sulfites, thioglycolic acid, borohydrides, salts, esters, and derivatives thereof.

11. The dyeing process according to claim 10, wherein the at least one reducing agent is catecholborane.

12. A compound chosen from disulfide compounds of formula (I₁), disulfide compounds of formula (I₂), thiol or thiol-protected compounds of formula (I₃), thiol or thiol-protected compounds of formula (I₄), thiol or thiol-protected compounds of formula (I₅):

(I₁)

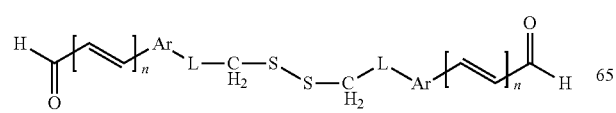

(I₂)
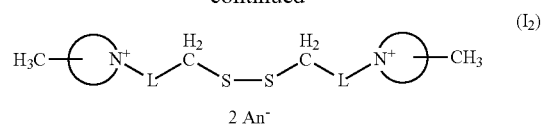
2 An⁻

(I₃)
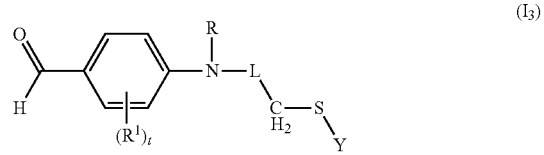

(I₄)
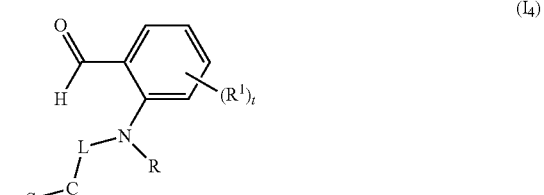

(I₅)

organic acid salts, mineral acid salts, optical isomers, geometrical isomers, and solvates thereof;
wherein, in formulae (I₁), (I₂), (I₃), (I₄) and (I₅):
Ar is chosen from optionally substituted arylene groups and optionally substituted heteroarylene groups;
R is chosen from hydrogen and $(C_1-C_6)$alkyl groups;
Y is chosen from:
i) hydrogen;
ii) alkali metals;
iii) alkaline-earth metals;
iv) ammonium groups $N^+R^\alpha R^\beta R^\gamma R^\delta An^-$ and phosphonium groups $P^+R^\alpha R^\beta R^\gamma R^\delta An^-$, with $R^\alpha$, $R^\beta$, $R^\gamma$, and $R^\delta$, independently of one another, each chosen from hydrogen and $(C_1-C_4)$alkyl groups, and An⁻ chosen from anionic counterions, and
v) protecting groups for a thiol function;
L is chosen from optionally substituted divalent $C_1-C_{20}$ hydrocarbon-based chains, optionally interrupted and/or optionally terminated at one end with at least one group chosen from:
i) divalent groups chosen from: —N($R_a$)—; —N⁺($R_a$)($R_b$)— An⁻; —O—; —S—; —C(O)—, and —S(O)₂—, with $R_a$ and $R_b$, independently of one another, each chosen from hydrogen, $(C_1-C_6)$alkyl groups, hydroxy $(C_1-C_6)$alkyl groups, and (di)($C_1$-$C_6$)(alkyl)amino($C_1$-$C_6$)alkyl groups, and An⁻ chosen from anionic counterions, and
ii) cationic heterocyclic and heteroaryl Het⁺An⁻ groups, with An⁻ chosen from anionic counterions and Het⁺ chosen from saturated and unsaturated 5- to 10-membered heterocycles and saturated and unsaturated 5- to 10-membered heteroaryl groups;
n is 0 or 1;

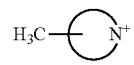

is chosen from 5- to 13-membered cationic heteroaryl groups which may comprise, besides the cationic nitrogen atom, 1 to 3 heteroatoms chosen from nitrogen, oxygen and sulfur, and which bear on a carbon atom a methyl group;

Het$^+$ is chosen from cationic heteroarylene groups bearing at least one methyl group chosen from (A), (B), (C), (D), and (E):

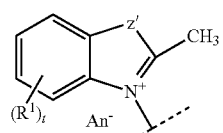
(A)

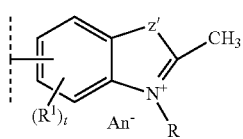
(B)

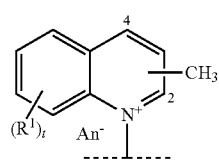
(C)

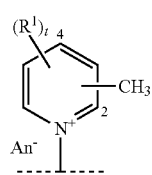
(D)

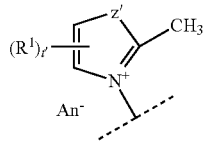
(E)

wherein, in (A), (B), (C), (D), and (E):
the methyl group of (C) and (D) is in position 2 or 4;
$R_1$, which may be identical or different, are each chosen from halogens, $(C_1-C_6)$alkyl groups, $(C_1-C_6)$alkoxy groups, $(C_1-C_6)$alkylthio groups, (di)$(C_1-C_6)$(alkyl)amino groups, $(C_1-C_6)$ polyhaloalkyl groups, hydroxyl groups, $(C_1-C_6)$ polyhydroxyalkyl groups, polyhydroxy$(C_1-C_6)$ alkoxy groups, cyano groups, R-G-C(G')- groups, RC(G')-G- groups, R'S(O)$_2$—N(R)— groups, and RR'N—S(O)$_2$— groups, with G or G', independently of one another, each chosen from oxygen, sulfur, and groups NR', and R and R', independently of one another, are each chosen from hydrogen and $(C_1-C_6)$alkyl groups;
R is chosen from hydrogen and (polyhydroxy)$(C_1-C_4)$alkyl groups;
or alternatively two contiguous groups $R_1$ form with the two carbon atoms that bear them an optionally substituted benzo group;
t is chosen from integers ranging from 0 to 4 inclusive;
t' is chosen from integers ranging from 0 to 2 inclusive;
Z' is chosen from oxygen, sulfur, and methylene groups —C(R$_2$)(R$_3$)—, with R$_2$ and R$_3$, independently of one another, each chosen from hydrogen and $(C_1-C_6)$alkyl groups;
An$^-$ is chosen from anionic counterions;
it being understood that the compounds of formula (I$_1$), (I$_2$), (I$_3$), (I$_4$) and (I$_5$) are not chosen from compounds (i) to (xxxiv):

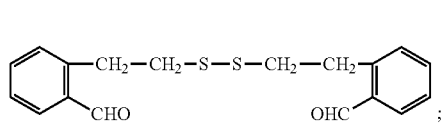
(i)

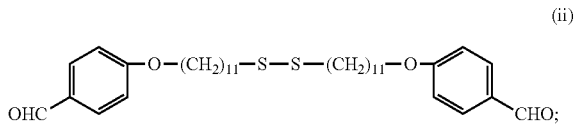
(ii)

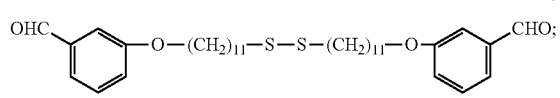
(iii)

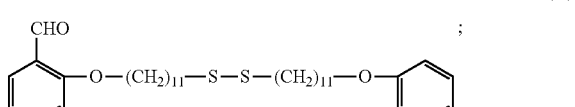
(iv)

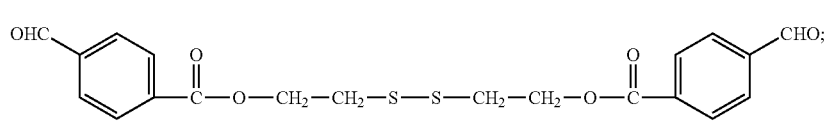
(v)

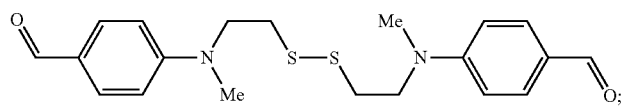
(vi)

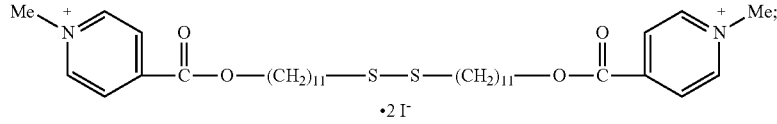
(vii)

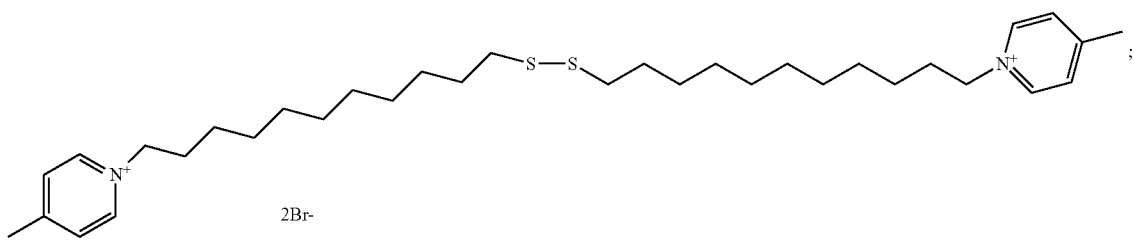
(viii)
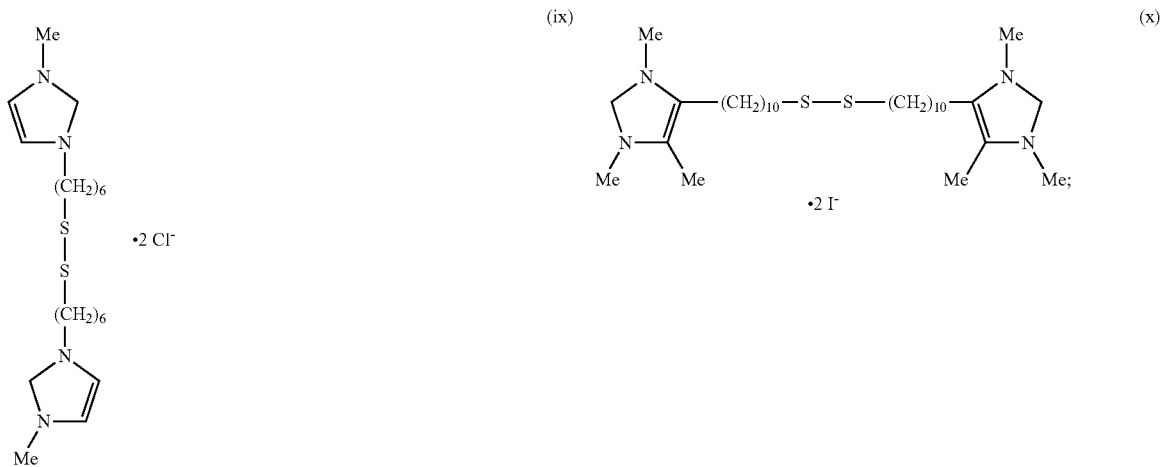
(ix) (x)
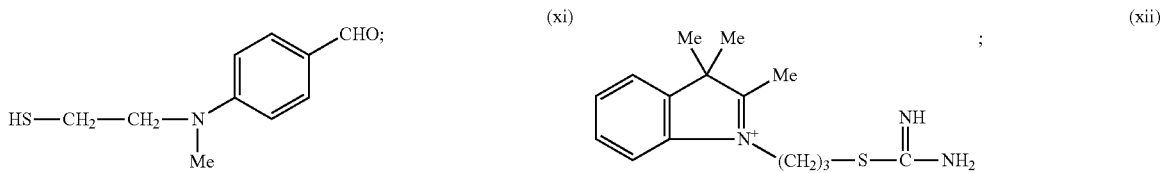
(xi) (xii)
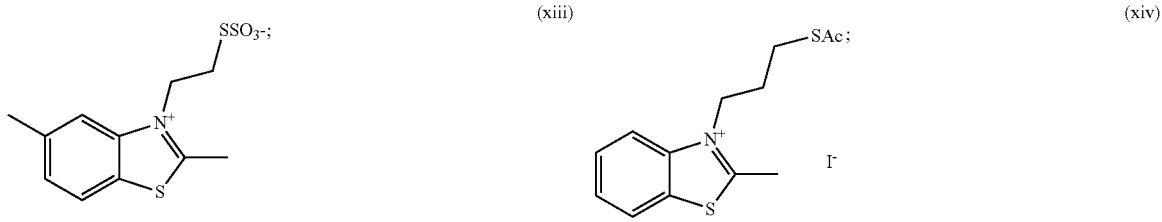
(xiii) (xiv)
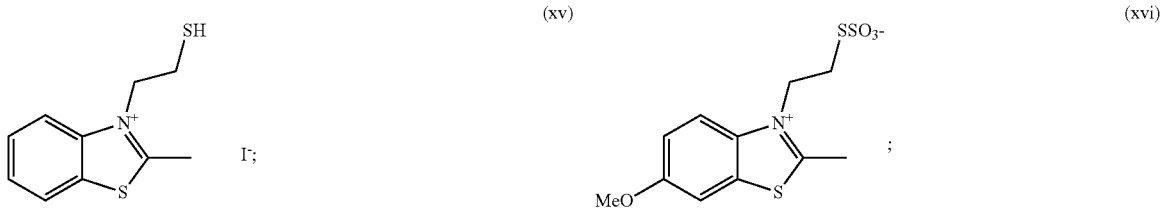
(xv) (xvi)
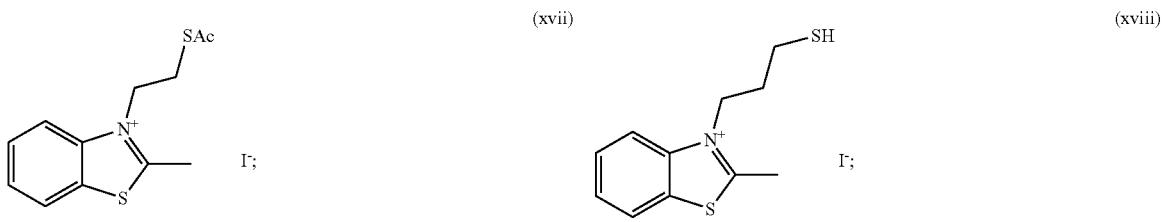
(xvii) (xviii)

(xix)
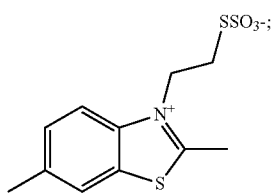
(xx)
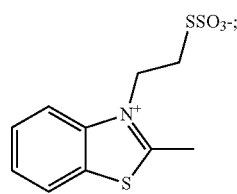
(xxi)
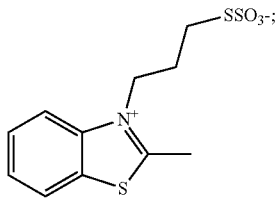
(xxii)
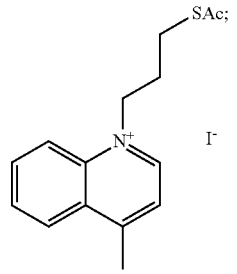
with Ac representing an acetyl group
(xxiii)
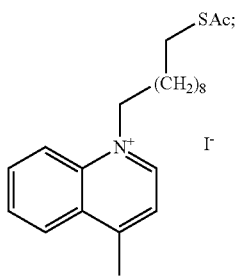
(xxiv)
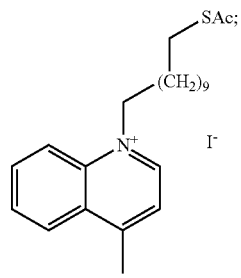
(xxv)
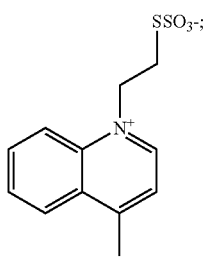
(xxvi)
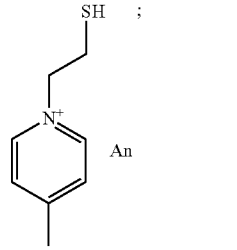
An = MeSO$_4^-$
or NO$_3^-$ or
pTSA$^-$
(xxvii)
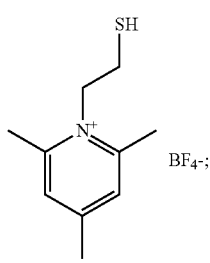
(xxviii)
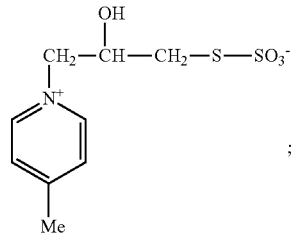
(xxix)
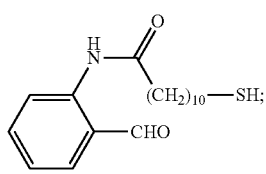
(xxx)

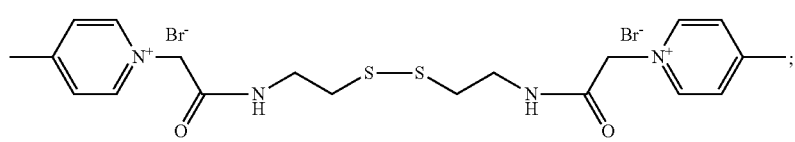

(xxxi)

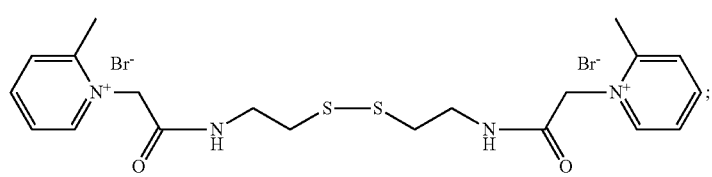

(xxxii)

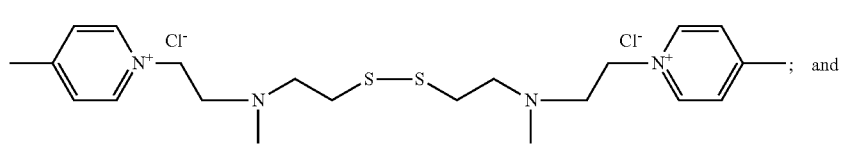

(xxxiii)

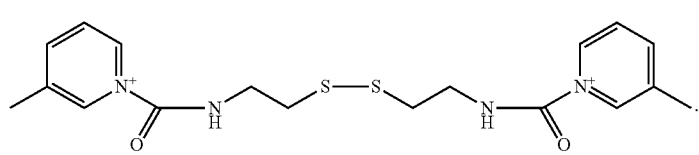

(xxxiv)

13. The compound according to claim 12, wherein said compound has formula ($I_6$):

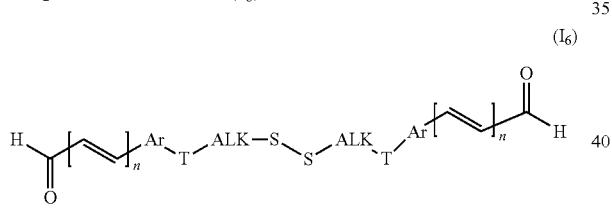

($I_6$)

wherein, in formula ($I_6$):

Ar is chosen from phenylene groups;

T is chosen from amino groups NR, amido groups —NR—C(O)—, and amido groups —C(O)—NR—, with R chosen from hydrogen and ($C_1$-$C_6$)alkyl groups;

ALK is chosen from divalent $C_1$-$C_{10}$alkylene chains, optionally interrupted with a cationic heteroaryl Het$^+$ An$^-$ group, with Het$^+$ chosen from saturated and unsaturated 5- to 10-membered heterocycles and saturated and unsaturated 5- to 10-membered heteroaryls, and An$^-$ chosen from counterions; and n is 0.

14. The compound according to claim 12, wherein said compound is chosen from:

1

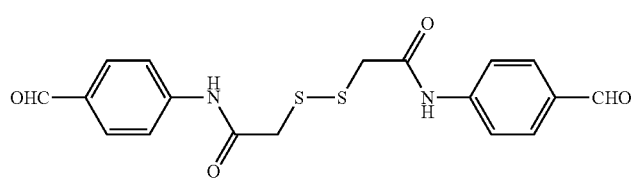

2

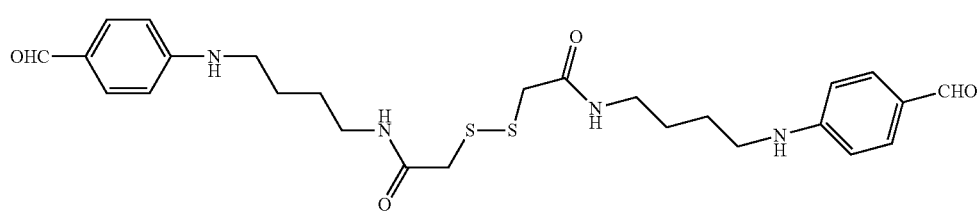

-continued
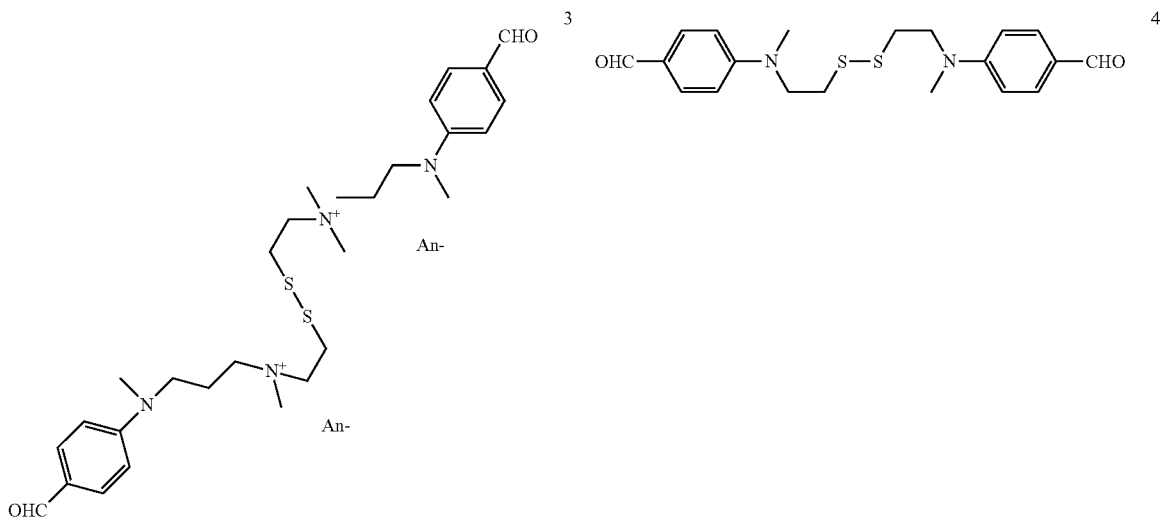
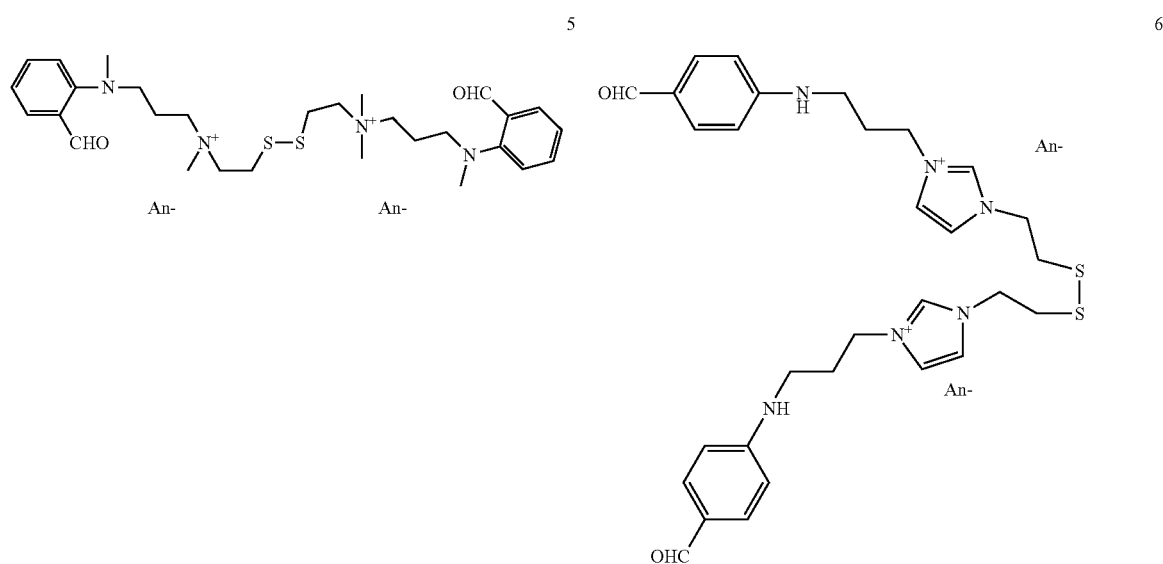
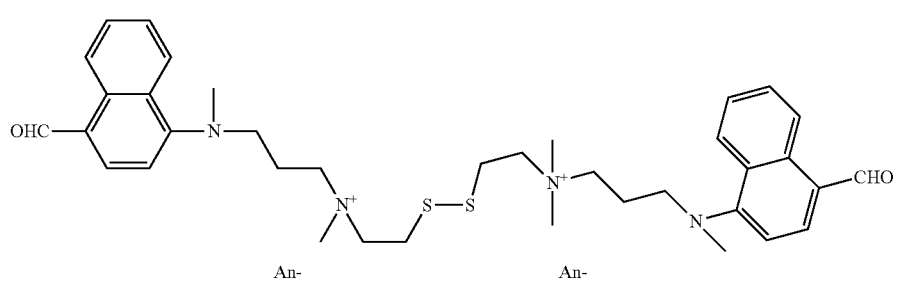

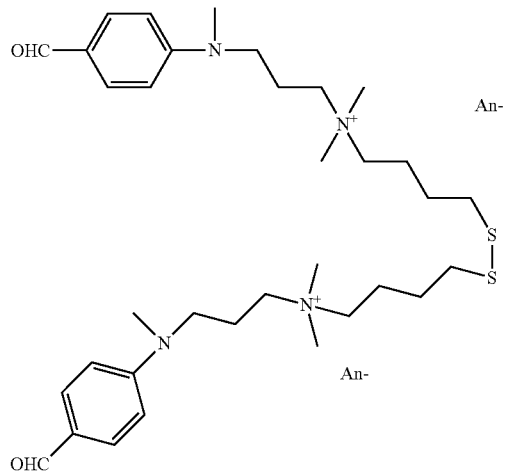
8
the precursors of formula (I) or (I₂) below:
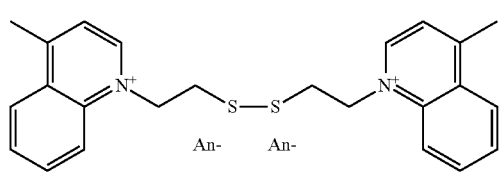
10
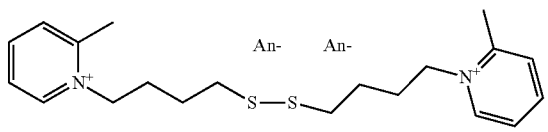
11
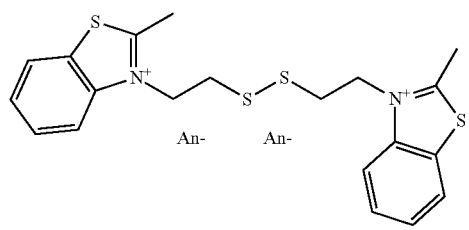
12
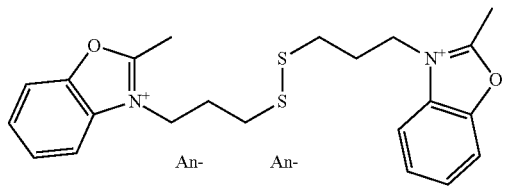
13
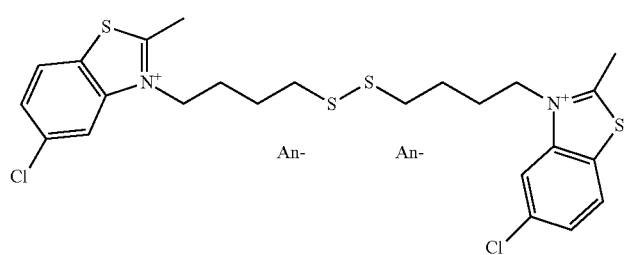
14

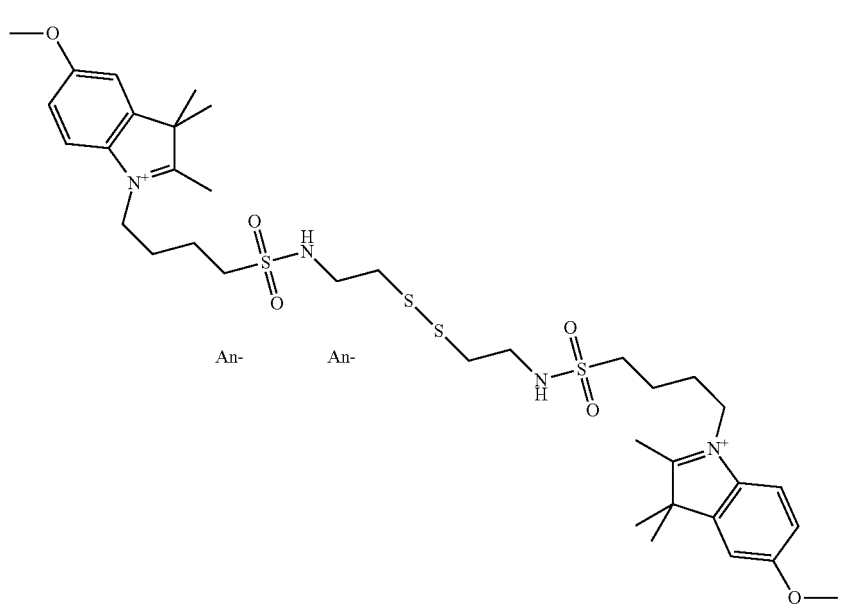
15
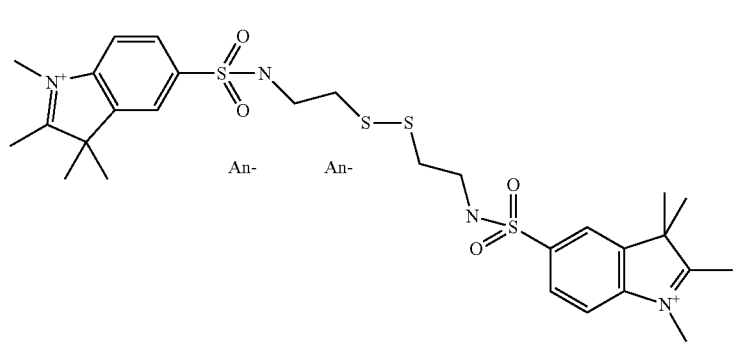
16
the precursors of formula (I₃) or (I₄) below:
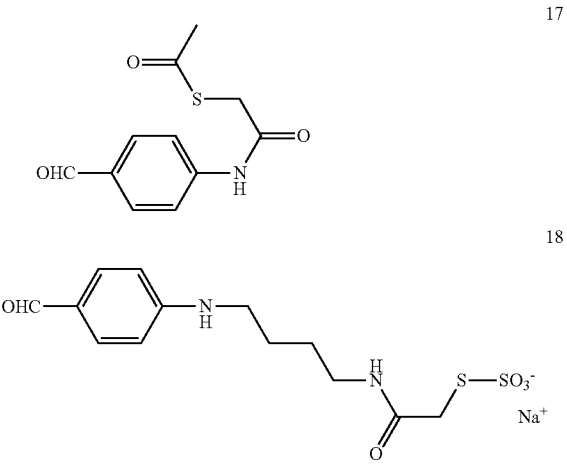
17
18
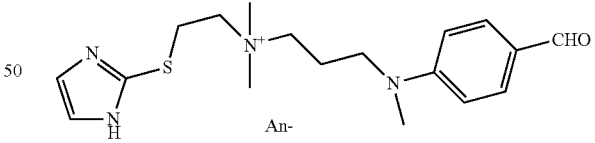
19
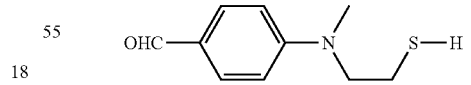
20
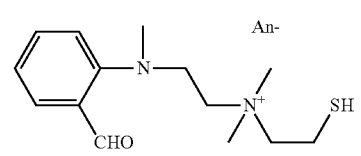
21

-continued

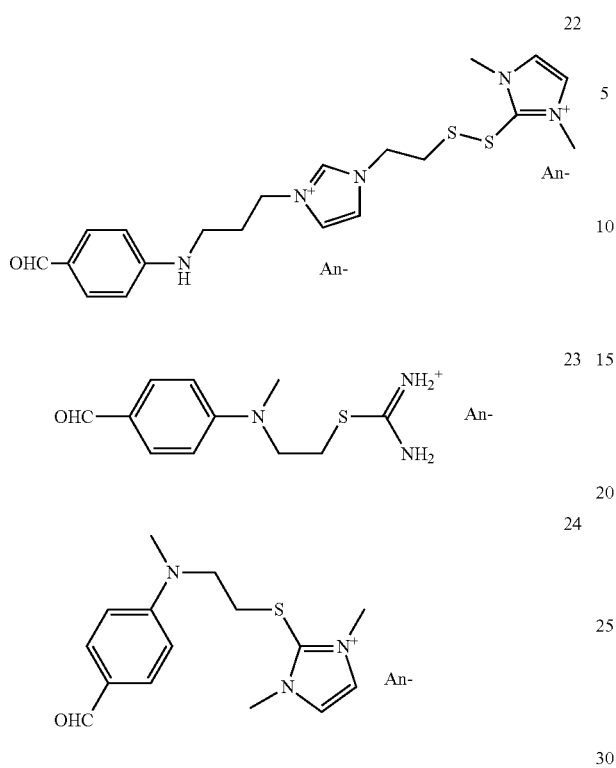

the precursors of formula (I₅) below:

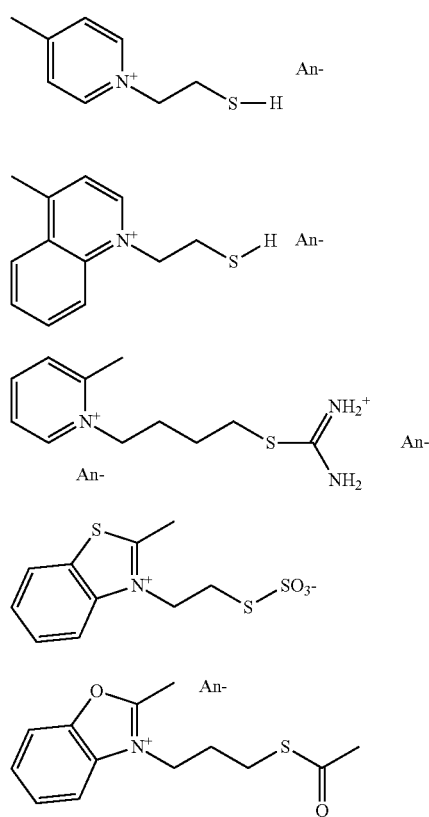

-continued

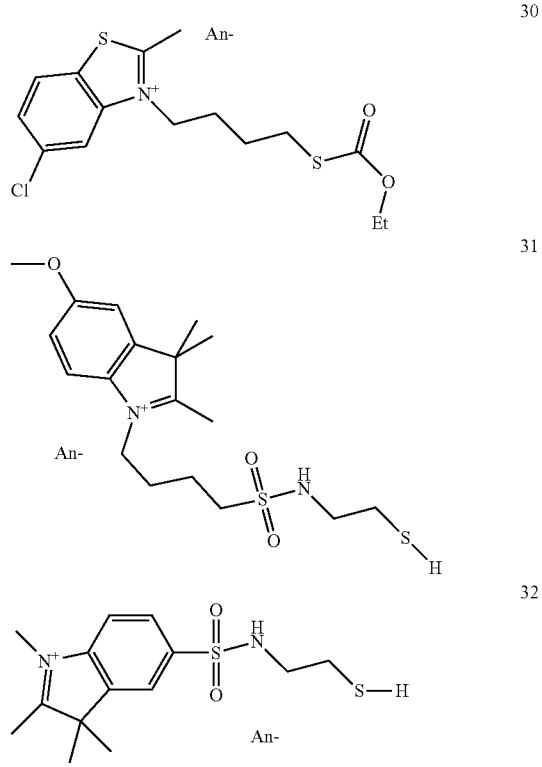

with An⁻ chosen from anionic counterions;
the following precursors of formula (II) containing an electrophilic group:
vanillin (4-hydroxy-3-methoxybenzaldehyde), isovanillin (3-hydroxy-4-methoxybenzaldehyde), 3,4-dihydroxybenzaldehyde, 4-hydroxybenzaldehyde, 3,5-dimethoxy-4-hydroxybenzaldehyde, 4-hydroxybenzaldehyde, 4-dimethylaminobenzaldehyde, 4-methyl-5-imidazolecarboxaldehyde, 4-dimethylaminocinnamaldehyde, 4-hydroxy-2-methoxybenzaldehyde, 3,5-dimethyl-4-hydroxybenzaldehyde, 4-dimethylamino-2-methoxybenzaldehyde, 2-hydroxybenzaldehyde, 4-hydroxy-1-naphthaldehyde, 4-methoxy-1-naphthaldehyde, 4-dimethylamino-1-naphthaldehyde, 4'-hydroxybiphenyl-1-carboxaldehyde, 2-hydroxy-3-methoxybenzaldehyde, 2,4-dihydroxybenzaldehyde, 3,4-dihydroxybenzaldehyde, 2,5-dihydroxybenzaldehyde, 2,3,4-trihydroxybenzaldehyde, 3,4,5-trihydroxybenzaldehyde, 2,4,6-trihydroxybenzaldehyde, 2,4-dimethoxybenzaldehyde, 2,3-dimethoxybenzaldehyde, 2,5-dimethoxybenzaldehyde, 3,5-dimethoxybenzaldehyde, 3,4-dimethoxybenzaldehyde, indole-3-carboxaldehyde, benzene-1,4-dicarboxaldehyde, 4-ethoxybenzaldehyde, 2-methyl-1,4-naphthoquinone, 4-carboxybenzaldehyde, 4-hydroxy-3-ethoxycinnamaldehyde, 3,5-dimethoxy-4-hydroxycinnamaldehyde, 3-methoxy-4-(1-pyrrolidinyl)benzaldehyde, 4-dimethyl-amino-3-methoxybenzaldehyde, 1,2,-phthalaldehyde, pyrrole-2-aldehyde, thiophene-2-aldehyde, thiophene-3-aldehyde, chromone-3-carboxaldehyde, 6-methyl-4-oxo-1(4H)-benzopyran-3-carboxaldehyde, N-methylpyrrole-2-aldehyde, 5-methylfurfural, 6-hydroxychromene-3-carboxyaldehyde, 6-methylindole-3- carboxaldehyde, 4-dibutylaminobenzaldehyde, N-ethylcarbazole-3-aldehyde, 4-diethylamino-2-hydroxybenzaldehyde, 3,4-dimethoxy-5-hydroxybenzaldehyde, 5-[4-(dimethylamino)phenyl]-2,4-pentadienal, 2,3-thiophenecarboxaldehyde, 2,5-thiophenedicarboxaldehyde, 2-methoxy-1-naphthaldehyde, 3-ethoxy-4-hydroxybenzaldehyde;

the following precursors of formula (II), containing a nucleophilic group:

1,4-dimethylquinolinium, 1,2-dimethylquinolinium, 1,4-dimethylpyridinium, 1,2-dimethylpyridinium, 2,4,6-trimethylpyrilium, 2-methyl-1-ethylquinolinium, 2,3-dimethylisoquinolinium, 1,2,3,3-tetramethyl-3H-indolium, 2,3-dimethylbenzothiazolium, 3-benzyl-2-benzothiazolium, 2-methyl-3-propylbenzothiazolium, 2,4-dimethyl-3-ethylthiazolium, 3-(2-carboxyethyl)-2,5-dimethylbenzothiazolium, 1,2,3-trimethylbenzimidazolium, 5,6-dichloro-1,3-diethyl-2-methylbenzimidazolium, 3-ethyl-2-methylbenzothiazolium, 5-chloro-3-ethyl-2-methylbenzothiazolium, 3-ethyl-2-methylbenzoxazolium salts, rhodanine; 2-methyl-3-(3-sulfopropyl)benzothiazolium hydroxide (inner salt), 4-methyl-1-(3-sulfopropyl)pyridinium hydroxide (inner salt), 4-methyl-1-(3-sulfopropyl)quinolinium hydroxide (inner salt), 5-methoxy-2-methyl-3-(3-sulfopropyl)benzothiazolium hydroxide (inner salt).

15. A cosmetic composition comprising at least one colorless thiol or thiol-protected disulfide dye precursor of formula $(I_1)$, $(I_2)$, $(I_3)$, $(I_4)$ and/or $(I_5)$:

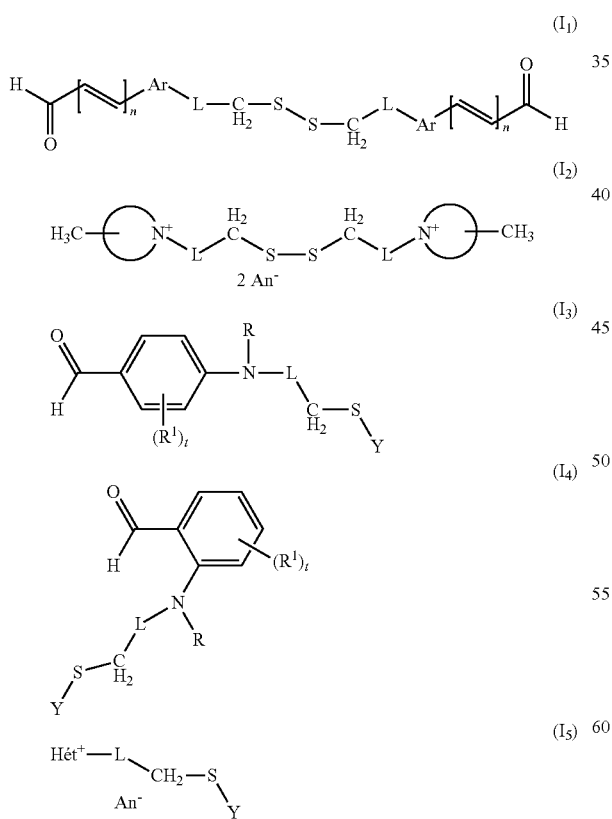

organic acid salts, mineral acid salts, optical isomers, geometrical isomers, and solvates thereof;

wherein, in formula $(I_1)$, formula $(I_2)$, formula $(I_3)$, formula $(I_4)$ and formula $(I_5)$:

Ar is chosen from optionally substituted arylene groups and optionally substituted heteroarylene groups;

R is chosen from hydrogen and $(C_1$-$C_6)$alkyl groups;

Y is chosen from:
  i) hydrogen;
  ii) alkali metals;
  iii) alkaline-earth metals;
  iv) ammonium groups $N^+R^\alpha R^\beta R^\gamma R^\delta An^-$ and phosphonium groups $P^+R^\alpha R^\beta R^\gamma R^\delta An^-$, with $R^\alpha$, $R^\beta$, $R^\gamma$, and $R^\delta$, independently of one another, each chosen from hydrogen and $(C_1$-$C_4)$alkyl groups, and $An^-$ chosen from anionic counterions, and
  v) protecting groups for a thiol function;

L is chosen from optionally substituted divalent $C_1$-$C_{20}$ hydrocarbon-based chains, optionally interrupted and/or optionally terminated at one end with at least one group chosen from:
  i) divalent groups chosen from: —N($R_a$)—; —N$^+$($R_a$)($R_b$)— An$^-$; —O—; —S—; —CO— and —SO$_2$—, with $R_a$ and $R_b$, independently of one another, each chosen from hydrogen, $(C_1$-$C_6)$alkyl groups, hydroxy $(C_1$-$C_6)$alkyl groups, and (di)($C_1$-$C_6$)(alkyl)amino($C_1$-$C_6$)alkyl groups, and An$^-$ chosen from anionic counterions, and
  ii) cationic heterocyclic and heteroaryl Het$^+$An$^-$ groups, with An$^-$ chosen from anionic counterions and Het$^+$ chosen from saturated and unsaturated 5- to 10-membered heterocycles and saturated and unsaturated 5- to 10-membered heteroaryl groups;

n is 0 or 1;

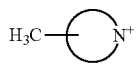

is chosen from 5- to 13-membered cationic heteroaryl groups which may comprise, besides the cationic nitrogen atom, 1 to 3 heteroatoms chosen from nitrogen, oxygen and sulfur, and which bear on a carbon atom a methyl group;

Het$^+$ is chosen from cationic heteroarylene groups bearing at least one methyl group chosen from (A), (B), (C), (D), and (E):

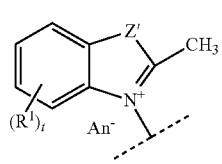

(A)

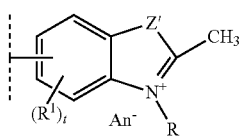

(B)

-continued

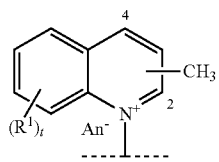
(C)

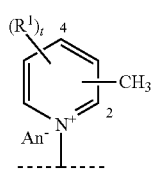
(D)

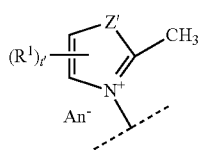
(E)

wherein, in (A), (B), (C), (D), and (E):
the methyl group of (C) and (D) is in position 2 or 4;
$R_1$ is chosen from halogens, $(C_1\text{-}C_6)$alkyl groups, $(C_1\text{-}C_6)$alkoxy groups, $(C_1\text{-}C_6)$alkylthio groups, (di)$(C_1\text{-}C_6)$(alkyl)amino groups, $(C_1\text{-}C_6)$ polyhaloalkyl groups, hydroxyl groups, $(C_1\text{-}C_6)$ polyhydroxyalkyl groups, polyhydroxy$(C_1\text{-}C_6)$alkoxy groups, cyano groups, R-G-C(G')- groups, RC(G')-G- groups, R'S(O)$_2$—N(R)— groups, and RR'N—S(O)$_2$— groups, with G or G', independently of one another, each chosen from oxygen, sulfur, and groups NR', and R and R', independently of one another, each chosen from hydrogen and $(C_1\text{-}C_6)$ alkyl groups;

R is chosen from hydrogen and (polyhydroxy)$(C_1\text{-}C_4)$alkyl groups;

or alternatively two contiguous groups $R_1$ form with the two carbon atoms that bear them an optionally substituted benzo group;

t is chosen from integers ranging from 0 to 4 inclusive;

t' is chosen from integers ranging from 0 to 2 inclusive;

Z' is chosen from oxygen, sulfur, and methylene groups —C($R_2$)($R_3$)—, with $R_2$ and $R_3$, independently of one another, each chosen from hydrogen and $(C_1\text{-}C_6)$alkyl groups;

An$^-$ is chosen from anionic counterions;

it being understood that the compounds of formulae ($I_1$), ($I_2$), ($I_3$), ($I_4$) and ($I_5$) are not compounds (i) to (xxxiv):

(i)
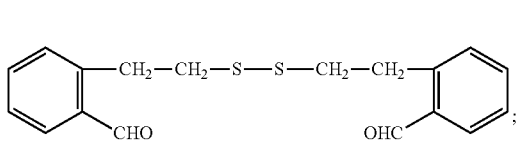

(ii)
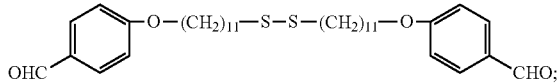

(iii)
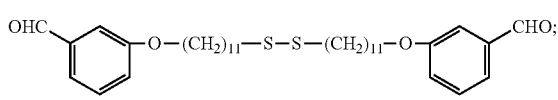

(iv)
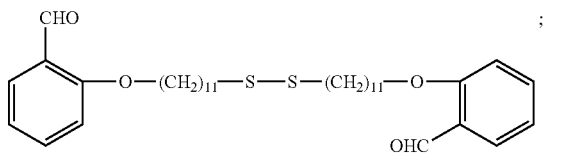

(v)
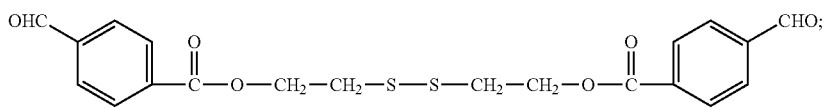

(vi)
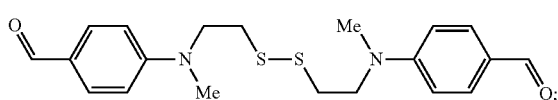

(vii)
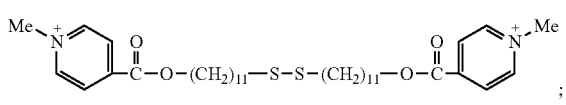

(viii)
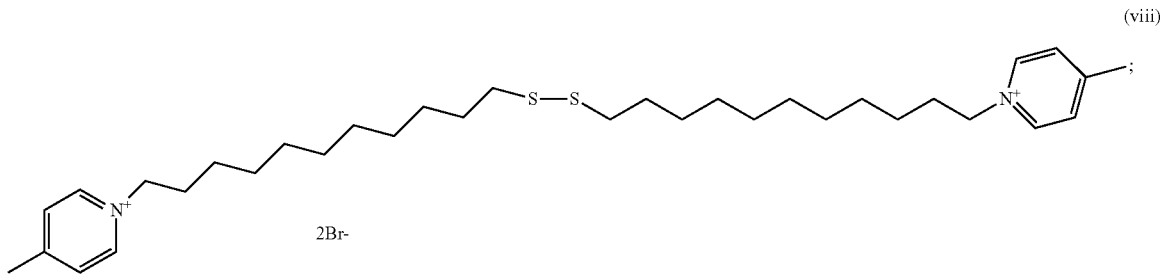

-continued
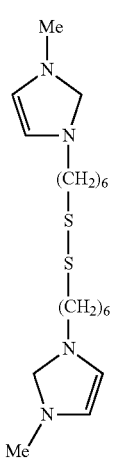
(ix)
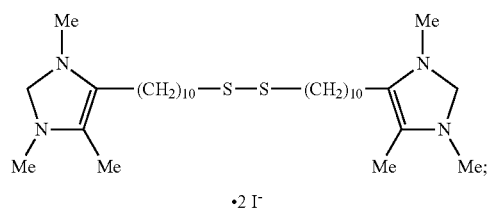
(x)
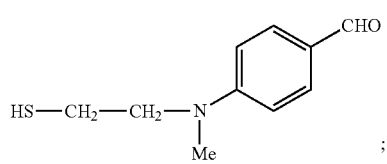
(xi)
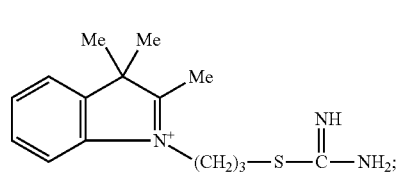
(xii)
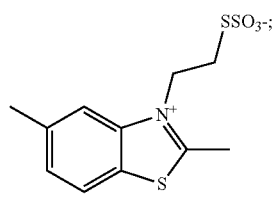
(xiii)
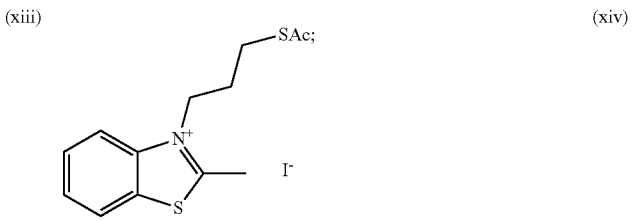
(xiv)
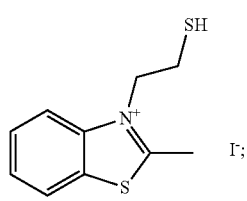
(xv)
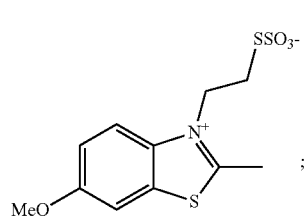
(xvi)
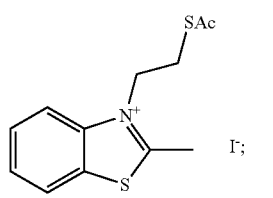
(xvii)
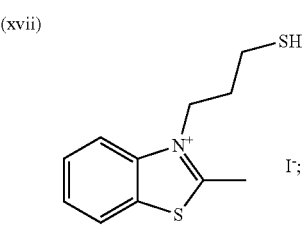
(xviii)
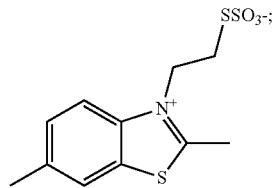
(xix)
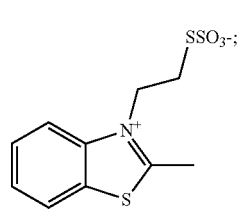
(xx)

-continued
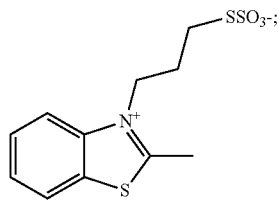 (xxi)
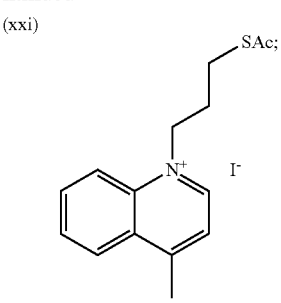 (xxii)
with Ac representing an acetyl group
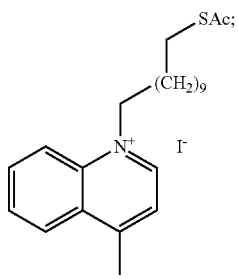 (xxiii)
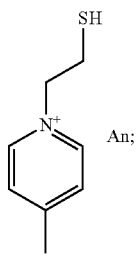 (xxiv)
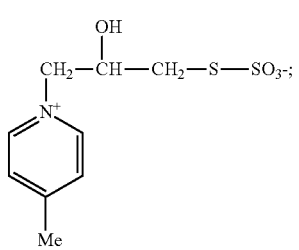 (xxv)
(xxvi)
An = MeSO₄⁻ or NO₃⁻ or pTSA⁻
(xxvii)
(xxviii)
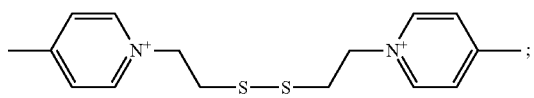
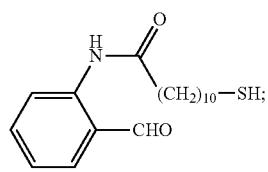 (xxix)
(xxx)
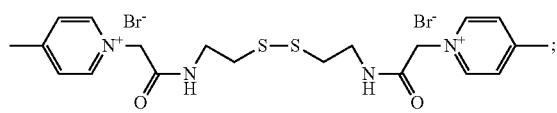 (xxxi)
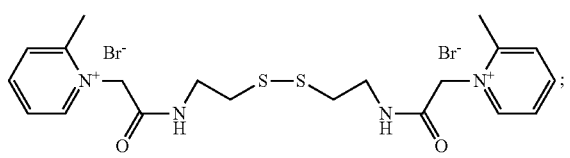 (xxxii)

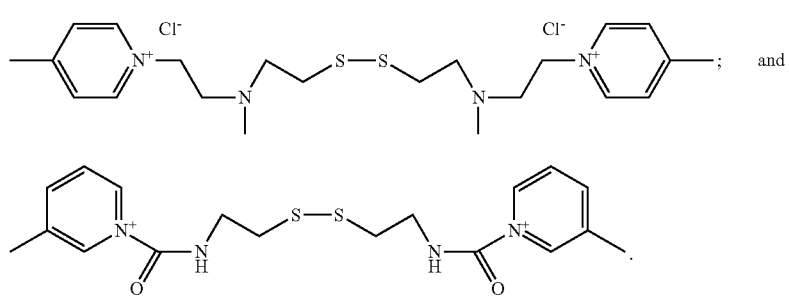

(xxxiii)

(xxxiv)

16. The cosmetic composition according to claim 15, wherein the at least one colorless thiol or thiol-protected disulfide dye precursor of formula $(I_1)$, $(I_2)$, $(I_3)$, $(I_4)$ and/or $(I_5)$ is present in an amount ranging from 0.001% to 50% by weight relative to the total weight of the composition.

17. A multi-compartment device comprising:
a first compartment comprising a cosmetic composition comprising at least one colorless thiol/disulfide precursor of formula (I)

[Z-A-L-S]$_x$—(Y)$_y$     formula (I):

a second compartment comprising a cosmetic composition comprising at least one colorless precursor of formula (II)

B—X     formula (II):

wherein B of the at least one colorless dye precursor of formula (II) reacts chemically with A of the at least one colorless thiol/disulfide dye precursor of formula (I) to form a colored or a colored and fluorescent chromophore B—X'-A-;
wherein, in formula (I) and formula (II):
x is 0 or 1;
y is 1 or 2;
L is chosen from optionally substituted divalent $C_1$-$C_{20}$ hydrocarbon-based chains, optionally interrupted and/or optionally terminated at one end with at least one group chosen from:
i) divalent groups chosen from: —N($R_a$)—; —N$^+$($R_a$)($R_b$)— An$^-$; —O—; —S—; —C(O)— and —S(O)$_2$—, with $R_a$ and $R_b$, independently of one another, each chosen from hydrogen, ($C_1$-$C_6$)alkyl groups, hydroxy ($C_1$-$C_6$)alkyl groups, and (di)($C_1$-$C_6$)(alkyl)amino($C_1$-$C_6$)alkyl groups, and An$^-$ chosen from anionic counterions, and
ii) cationic heterocyclic and heteroaryl Het$^+$An$^-$ groups, with An$^-$ chosen from anionic counterions and Het$^+$ chosen from saturated and unsaturated 5- to 10-membered heterocycles and saturated and unsaturated 5- to 10-membered heteroaryl groups;
A and B, independently of one another, are each chosen from colorless chromophores;
X and Z, independently of one another, are each chosen from chemical functional groups capable of reacting together to form a group X';
X' is chosen from chains that allow electron transfer between chromophore A and chromophore B;
Y is chosen from:
i) hydrogen;
ii) alkali metals;
iii) alkaline-earth metals;
iv) ammonium groups N$^+$R$^\alpha$R$^\beta$R$^\gamma$R$^\delta$An$''^-$ and phosphonium groups P$^+$R$^\alpha$R$^\beta$R$^\gamma$R$^\delta$An$''^-$, with R$^\alpha$, R$^\beta$, R$^\gamma$, and R$^\delta$, independently of one another, each chosen from hydrogen and ($C_1$-$C_4$)alkyl groups, and An$''^-$ chosen from anionic counterions; and
v) protecting groups for a thiol function;
it being understood that when y is 2, then x is zero, and when x is 1, then y is 1,
optionally, another compartment comprising at least one reducing agent capable of reducing keratin fibers and/or the at least one colorless thiol/disulfide precursor of formula (I);
and/or optionally another compartment containing at least one oxidizing agent capable of fixing the at least one colorless thiol/disulfide precursor of formula (I) to the keratin fibers.

\* \* \* \* \*